(12) United States Patent
Sletten et al.

(10) Patent No.: US 12,043,619 B2
(45) Date of Patent: Jul. 23, 2024

(54) NEAR AND SHORTWAVE INFRARED POLYMETHINE DYES

(71) Applicant: MASSACHUSETTS INSTITUTE OF TECHNOLOGY, Cambridge, MA (US)

(72) Inventors: Ellen M. Sletten, Los Angeles, CA (US); Timothy M. Swager, Los Angeles, CA (US); Justin Caram, Los Angeles, CA (US)

(73) Assignee: Massachusetts Institute of Technology, Cambridge, MA (US)

( * ) Notice: Subject to any disclaimer, the term of this patent is extended or adjusted under 35 U.S.C. 154(b) by 954 days.

(21) Appl. No.: 16/499,700

(22) PCT Filed: Apr. 3, 2018

(86) PCT No.: PCT/US2018/025842
§ 371 (c)(1),
(2) Date: Sep. 30, 2019

(87) PCT Pub. No.: WO2018/187295
PCT Pub. Date: Oct. 11, 2018

(65) Prior Publication Data
US 2023/0192675 A1 Jun. 22, 2023

Related U.S. Application Data

(60) Provisional application No. 62/481,061, filed on Apr. 3, 2017.

(51) Int. Cl.
| | | |
|---|---|---|
| C07D 411/10 | (2006.01) | |
| C07D 311/62 | (2006.01) | |
| C07D 311/68 | (2006.01) | |
| C07D 405/06 | (2006.01) | |
| C07D 405/10 | (2006.01) | |
| C07D 407/06 | (2006.01) | |
| C07D 407/10 | (2006.01) | |
| C09B 23/01 | (2006.01) | |
| C09B 23/04 | (2006.01) | |
| C09B 23/06 | (2006.01) | |
| C09B 23/08 | (2006.01) | |

(52) U.S. Cl.
CPC .......... C07D 411/10 (2013.01); C07D 311/62 (2013.01); C07D 311/68 (2013.01); C07D 405/06 (2013.01); C07D 405/10 (2013.01); C07D 407/06 (2013.01); C07D 407/10 (2013.01); C09B 23/0016 (2013.01); C09B 23/0058 (2013.01); C09B 23/0066 (2013.01); C09B 23/04 (2013.01); C09B 23/06 (2013.01); C09B 23/083 (2013.01)

(58) Field of Classification Search
CPC ............... C07D 411/10; C07D 311/62; C07D 311/68; C07D 405/06; C07D 405/10; C07D 407/06; C07D 407/10; C09B 23/0016; C09B 23/0058; C09B 23/0066; C09B 23/04; C09B 23/06; C09B 23/083
See application file for complete search history.

(56) References Cited

U.S. PATENT DOCUMENTS

| | | |
|---|---|---|
| 4,714,667 A | 12/1987 | Sato et al. |
| 5,166,041 A | 11/1992 | Murofushi et al. |
| 5,214,164 A | 5/1993 | Drexhage et al. |
| 5,262,549 A | 11/1993 | Telfer et al. |
| 6,221,574 B1 | 4/2001 | Missfeldt |
| 9,862,682 B2 | 1/2018 | Zhang et al. |
| 11,292,778 B2 | 4/2022 | Sletten et al. |
| 2002/0115862 A1 | 8/2002 | Czerney et al. |
| 2004/0162423 A1 | 8/2004 | Czerney et al. |
| 2009/0200167 A1 | 8/2009 | Kratzmeier et al. |
| 2009/0252687 A1 | 10/2009 | Cooper |
| 2011/0054188 A1 | 3/2011 | Koori et al. |
| 2012/0119171 A1 | 5/2012 | Ohashi et al. |
| 2013/0039858 A1 | 2/2013 | Brown et al. |
| 2015/0080721 A1 | 3/2015 | Novak et al. |
| 2015/0322078 A1 | 11/2015 | Hermanson et al. |
| 2020/0140404 A1 | 5/2020 | Sletten et al. |
| 2020/0363576 A1 | 11/2020 | Yamada et al. |
| 2021/0363124 A1 | 11/2021 | Sletten et al. |

FOREIGN PATENT DOCUMENTS

| | | |
|---|---|---|
| EP | 0362387 A1 | 4/1990 |
| EP | 0438123 A2 | 7/1991 |
| EP | 0841189 A1 | 5/1998 |
| EP | 3118201 A1 | 1/2017 |
| JP | S60 252346 A | 12/1985 |
| JP | 3341141 B2 | 11/2002 |
| JP | 2003176270 A | 6/2003 |
| JP | 2004/083799 A | 3/2004 |
| JP | 2007298642 A | 11/2007 |
| JP | 2016113503 A | 6/2016 |
| WO | WO-2014/035712 A1 | 3/2014 |
| WO | WO-2014/081419 A2 | 5/2014 |
| WO | WO-2015042202 A1 | 3/2015 |

(Continued)

OTHER PUBLICATIONS

Extended European Search Report for EP Application No. 18813396.1 dated Feb. 16, 2021.
Extended European Search Report for EP Application No. EP 18781895 mailed Feb. 16, 2021.
Ischenko, "Structure and Spectral-Luminescent Properties of Ploymethine Dyes," Russian Chemical Reviews, 60(8):865-880 (1991).
Viniychuk et al., "Electronic Transitions in Polymethine Dyes Involving Local and Delocalized Levels," Journal of Molecular Structure. 1060:30-37 (2013).
Extended European Search Report for EP Application No. 19892945.7 dated Dec. 16, 2022.

(Continued)

Primary Examiner — Alicia L Otton
(74) Attorney, Agent, or Firm — Foley Hoag LLP; David P. Halstead; Alexander J. Chatterley

(57) ABSTRACT

Near infrared and shortwave infrared dyes can have polymethine structures.

9 Claims, 37 Drawing Sheets

(56) References Cited

FOREIGN PATENT DOCUMENTS

| WO | WO-2015/066290 A1 | 5/2015 |
|---|---|---|
| WO | WO-2016/081813 A1 | 5/2016 |
| WO | WO-2017/025968 A1 | 2/2017 |
| WO | WO-2017027721 A1 | 2/2017 |
| WO | WO-2018/187295 A1 | 10/2018 |
| WO | WO-2018/226720 | 12/2018 |
| WO | WO-2020/118116 A1 | 6/2020 |
| WO | WO-2020/245446 A1 | 12/2020 |
| WO | WO-2020/245447 A1 | 12/2020 |
| WO | WO-2023/150776 A1 | 8/2023 |

OTHER PUBLICATIONS

International Search Report and Written Opinion for International Application No. PCT/US18/25842 dated May 29, 2018.
Katritzsky et al., "Comprehensive Heterocyclic Chemistry," Elsevier Science, Par 2.02 titled "Reactivity of Six-membered Rings", scheme 19, compound 77; Par. 2.23 titled "Pyrans and Fused Pyrans: (ii) Reactivity", compound 119 (1984).
CAS Registry No. 101468-00-2.
CAS Registry No. 2377085-42-0.
CAS Registry No. 2377085-47-5.
Cosco ED, et al. Flavylium polymethine fluorophores for near- and shortwave infrared imaging. Angewandte Chemie International Edition. Oct. 9, 2017; 56(42):13126-9.
International Search Report and Written Opinion for Application No. PCT/US2023/062095 dated May 18, 2023.
Kudinova et al., "Pyrylocyanines. 31. Benzopyrylocarbocyanine dyes containing hydrocarbon bridges in chromophore," Khimiya Geterotsiklicheskikh Soedinenii, 10: 1319-23 (1993).
Atchison et al., "Iodinated Cyanine Dyes: A New Class of Sensitisers for; use in NIR Activated Photodynamic Therapy (PDT), " Chemical Communications, 53(12): 2009-2012 (2017).
Blackburn et al., "302. Reactions of flavylium salts with dimethylaniline and malonic acid," Journal of the Chemical Society (Resumed), 1957: 1573-1576 (1957).
CAS Registry No. 169336-73-6 (Oct. 27, 1995).
CAS Registry No. 219991-09-0 (Feb. 25, 1999).
Chen et al., "Development of Unique Xanthene-Cyanine Fused Near-Infrared Fluorescent Fluorophores with Superior Chemical Stability for Biological Fluorescence Imaging," Chemistry—A European Journal, 21(2): 733-745 (2015).
Detty et al,. "Heavy Atom Effects in Tellurapyrylium Dyes Useful in Photodynamic Therapy and Catalytic Generation of H2O2," Phosphorus, Sulfur, and Silicon and the Related Elements, 67(1-4): 383-404 (1992).
Gadjev et al., "Near-infrared absorbing asymmetric trimethinecyanine dyes containing benz[c,d]indolium and pyrylium end groups," Dyes and Pigments, 17(2): 153-162 (1991).
Gandioso et al., "High Photostability in Nonconventional Coumarins with Far-Red/NIR Emission through Azetidinyl Substitution," The Journal Of Organic Chemistry, 83(19): 11519-11531 (2018).
Gavrilyuk et al., "Pyrolocyanines. 17. Symmetrical flavylocyanines based on methoxy-substituted 4-methylflavylium salts," Chemistry of Heterocyclic Compounds, 19(3): 243-247 (1983).
Gavrilyuk et al., "Pyrylocyanines. 18. Unsymmetrical flavylocyanines on the basis of methoxysubstituted 4-methylflavylium salts," Chemistry of Heterocyclic Compounds, 19(9): 948-950 (1983).
Guo et al., "Preliminary structure-activity relationship study of heptamethine indocyanine dyes for tumor-targeted imaging," Journal of Innovative Optical Health Sciences, 6(01): 1350003 (2013).
Henary et al., "Synthesis and applications of benzothiazole containing cyanine dyes," Heterocyclic Communications, 19(1): 1-11 (2013).
International Search Report and Written Opinion for International Patent Application No. PCT/US2019/064790 mailed Mar. 17, 2020.
Kamel et al., "Dibenzoxanthylium salts-III : Studies on 9-methylene-3,4,5,6-dibenzoxanthene and 3,4,5,6-dibenzoxanthylomethines," Tetrahedron, 20(3): 483-489 (1964).
Kovalska et al., "6,6'-Disubstituted benzothiazole trimethine cyanines—new fluorescent dyes for DNA detection," Spectrochimica Acta Part A: Molecular and Biomolecular Spectroscopy, 65(2): 271-277 (2006).
Li et al., "An Efficient 1064 nm NIR-II Excitation Fluorescent Molecular Dye for Deep-Tissue High-Resolution Dynamic Bioimaging," Angewandte Chemie International Edition, 57(25): 7483-7487 (2018).
Li et al., "Small Molecule Near-Infrared Boron Dipyrromethene Donors for Organic Tandem Solar Cells," Journal Of The American Chemical Society, 139(39): 13636-13639 (2017).
Mikubayeva et al., "Combined Sensitisation of Benzaldehyde Diphenylhydrazones: Effect of Hydrazone Structure on Sensitization Efficiency," Eurasian ChemTech Journal, 6(2): 133-138 (2004).
Mishra et al., "Cyanines during the 1990s: A Review," Chemical Reviews, 100(6): 1973-2012 (2000).
Shandura et al., "Substituted xanthylocyanines. II. Pyroninocyanines," Dyes and Pigments, 66(3): 171-177 (2005).
Shi et al., "Review on near-infrared heptamethine cyanine dyes as theranostic agents for tumor imaging, targeting, and photodynamic therapy," Journal of Biomedical Optics, 21(5): 050901 (2016).
Shindy et al., "Fundamentals in the chemistry of cyanine dyes: A review," Dyes and Pigments, 145: 505-513 (2017).
Thimsen et al., "Shortwave-infrared (SWIR) emitters for biological; imaging: a review of challenges and opportunities," Nanophotonics, 6(5): 1043-1054 (2017).
Usama et al., "Optimized Heptamethine Cyanines for Photodynamic Therapy," ACS Applied Bio Materials, 1(4): 1195-1205 (2018).
Vasyluk et al., "Breaking of symmetrical charge distribution in xanthylocyanine chromophores detecting by their absorption spectra," Journal of Molecular Structure, 990(1-3): 6-13 (2011).
Wei et al., "Design of NIR Chromenylium-Cyanine Fluorophore Library for "Switch-ON" and Ratiometric Detection of Bio-Active Species In Vivo," Analytical Chemistry, 88(3): 1842-1849 (2016).
Yarmoluk et al., "Optimized Dyes for Protein and Nucleic Acid Detection," Advanced Fluorescence Reporters in Chemistry and Biology III, 113: 161-199 (2011).
Zhang et al., "Recent Advances in Near-Infrared Absorption Nanomaterials as Photoacoustic Contrast Agents for Biomedical Imaging," Chinese Journal of Chemistry, 33(1): 35-52 (2014).
Cosco et al., "Flavylium Polymethine Fluorophores for Near- and Shortwave Infrared Imaging," Angewandte Chemie—International Edition, 56(42):13126-13129 (2009).
Gorka et al., "A near-IR uncaging strategy based on cyanine photochemistry," J Am Chem Soc., 136(40): 14153-14159 (2014).
Hong et al., "Multifunctional in Vivo Vascular Imaging Using Near-Infrared II Fluorescence," Nature Medicine, 18:1841-1846 (2012).
International Search Report and Written Opinion for International Application No. PCT/US2018/025842 dated May 29, 2018.
International Search Report and Written Opinion for International Application No. PCT/US2018/036099 mailed Aug. 26, 2018.
Nani et al., "Cyanine Photocages Enable the Near-IR Light Activation of Antibody-Drug Conjugates," Angew Chem Int Ed Engl., 54(46):13635-13638 (2015).
Calzaferri et al., "Light-harvesting host-guest antenna materials for photonic devices" Organic Optoelectronics and Photonics II, vol. 6192 (2006).

Scheme 1

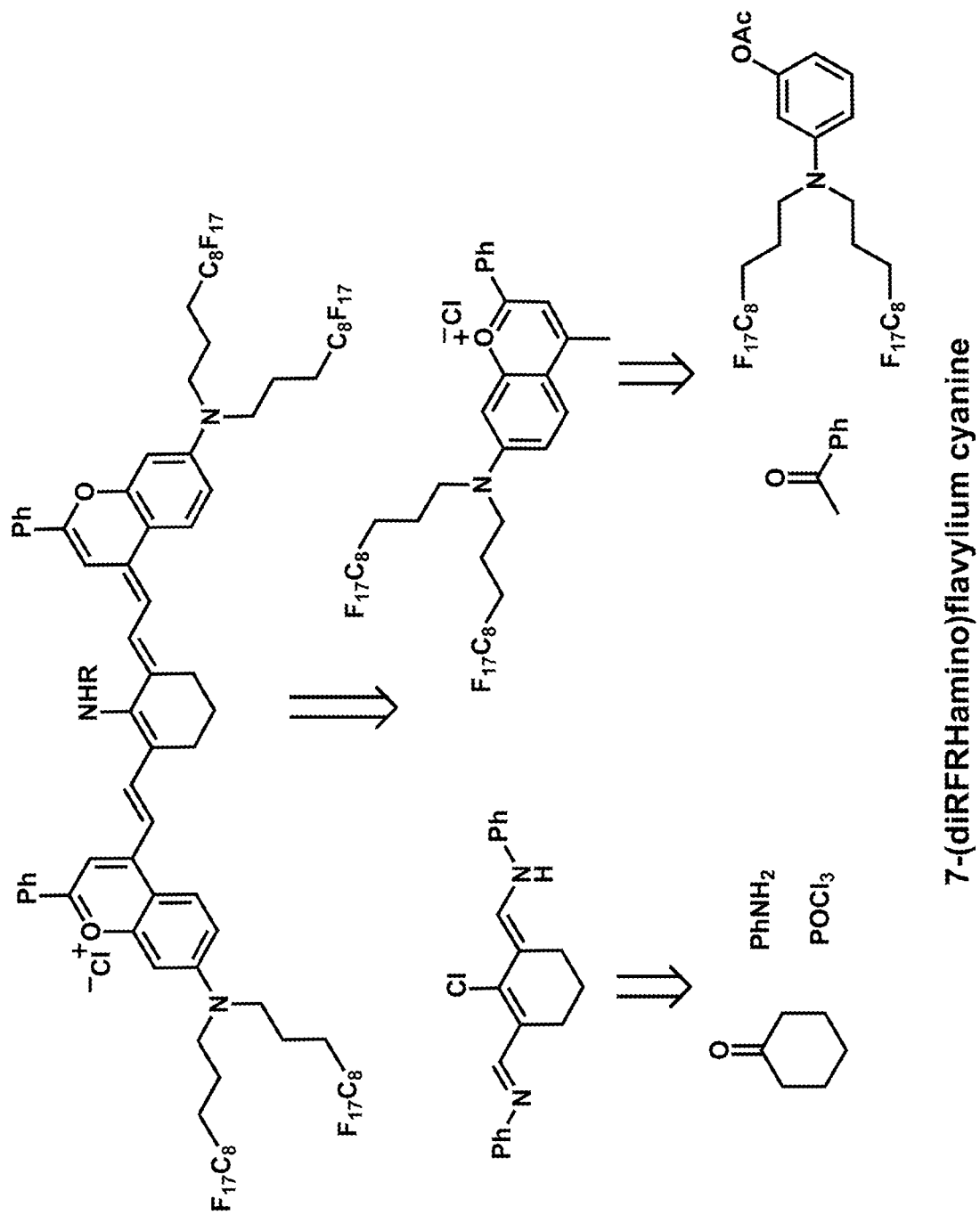
FIG. 1D 7-(diRFRHamino)flavylium cyanine

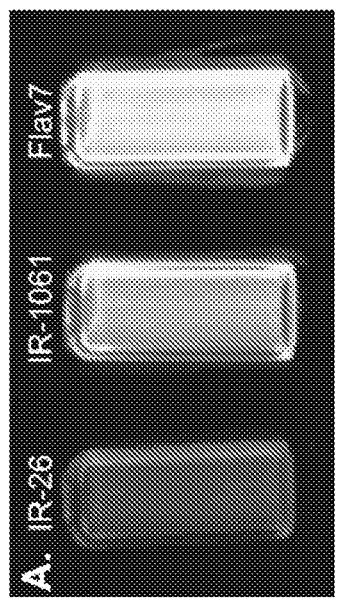
FIG. 3A
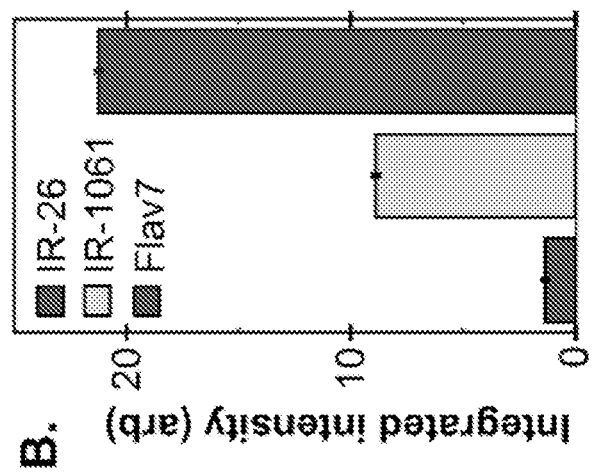
FIG. 3C
FIG. 3B

NEAR AND SHORTWAVE INFRARED POLYMETHINE DYES

PRIORITY CLAIM

This application is the 371 U.S. National-Stage application of PCT/US2018/025842, filed Apr. 3, 2018, which claims priority to U.S. Provisional Patent Application No. 62/481,061, filed Apr. 3, 2017, the contents of each of which are incorporated by reference in their entirety.

STATEMENT REGARDING FEDERALLY SPONSORED RESEARCH OR DEVELOPMENT

This invention was made with government support under DE-SC0001088 awarded by the U.S. Department of Energy. The government has certain rights in the invention.

TECHNICAL FIELD

This invention relates to dyes that emit near and shortwave infrared light.

BACKGROUND

Optical imaging has become an invaluable technique throughout the chemical sciences to obtain information on complex, dynamic systems. The toolbox of fluorophores emitting between 250 and 800 nm is extensive and provides many options for multiplexed imaging and turn on reagents. However, the region above 800 nm is often more desirable as a result of decreased scattering of light and minimal background absorption and emission from naturally occurring chromophores. This phenomenon has been exquisitely demonstrated by Hongjie Dai and coworkers, who have shown that the depth and resolution of in vivo imaging is superior in the near infrared II region (1000-1700 nm), a specific portion of the shortwave infrared (SWIR, 1000-2000 nm). This was originally demonstrated with carbon nanotubes, quantum dots, and rare earth materials. More recently, thio-containing dyes have been employed for imaging in the SWIR.

SUMMARY

The SWIR represents an underutilized region of the electromagnetic spectrum with significant room for technological advances if appropriate molecules and materials are developed for this region. The specific invention is the brightest polymethine dye for the SWIR. Polymethine dyes are superior to existing fluorophores (such as the thio-based dyes developed by Dai and coworkers) for the SWIR due to their high extinction coefficients, narrow absorption and emission bands. Current promising applications for the SWIR dyes can include night vision, moisture and blood detection, quality control, optical taggant technologies turn on probes for sensor development and drug delivery.

In one aspect, a compound can be a flavylium polymethine dye wherein the polymethine includes a methine chain from 1 to 7 carbons and having a fluorescence emission from 680 to 1045 nm.

In certain embodiments, the flavylium polymethine dye can include a dialkylamino flavylium moiety.

In certain embodiments, the dialkylamino flavylium moiety can be a dimethylamino flavylium moiety or a diethylamino flavylium moiety.

In certain embodiments, the polymethine can be a monomethine dye, a tri-methine dye, a penta-methine dye or a hepta-methine dye.

In another aspect, the compound can be of formula (I):

(I)

wherein n is 1, 2, or 3,

X⁻ is Cl⁻, ClO₄⁻, BF₄⁻, Br⁻, I⁻, tosylate, triflate, trifluoroacetate, acetate, bromide, or tetraalkylborate, at least one Het is a flavylium heteroaryl and the other Het is heteroaryl, and and the methine is substituted or unsubstituted.

In certain embodiments, the at least one Het can be amino flavylium and the other Het can be flavyl, flavylium, indolyl, or cyanyl.

In certain embodiments, the compound can be a flavylium polymethine.

In certain embodiments, the compound can be

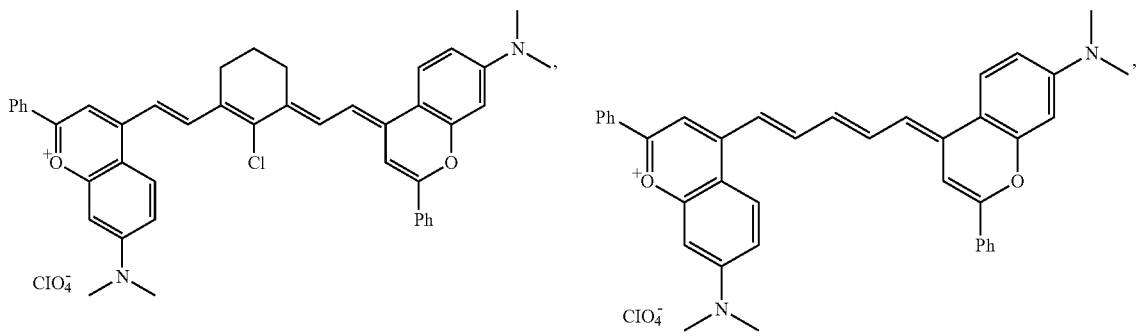

-continued

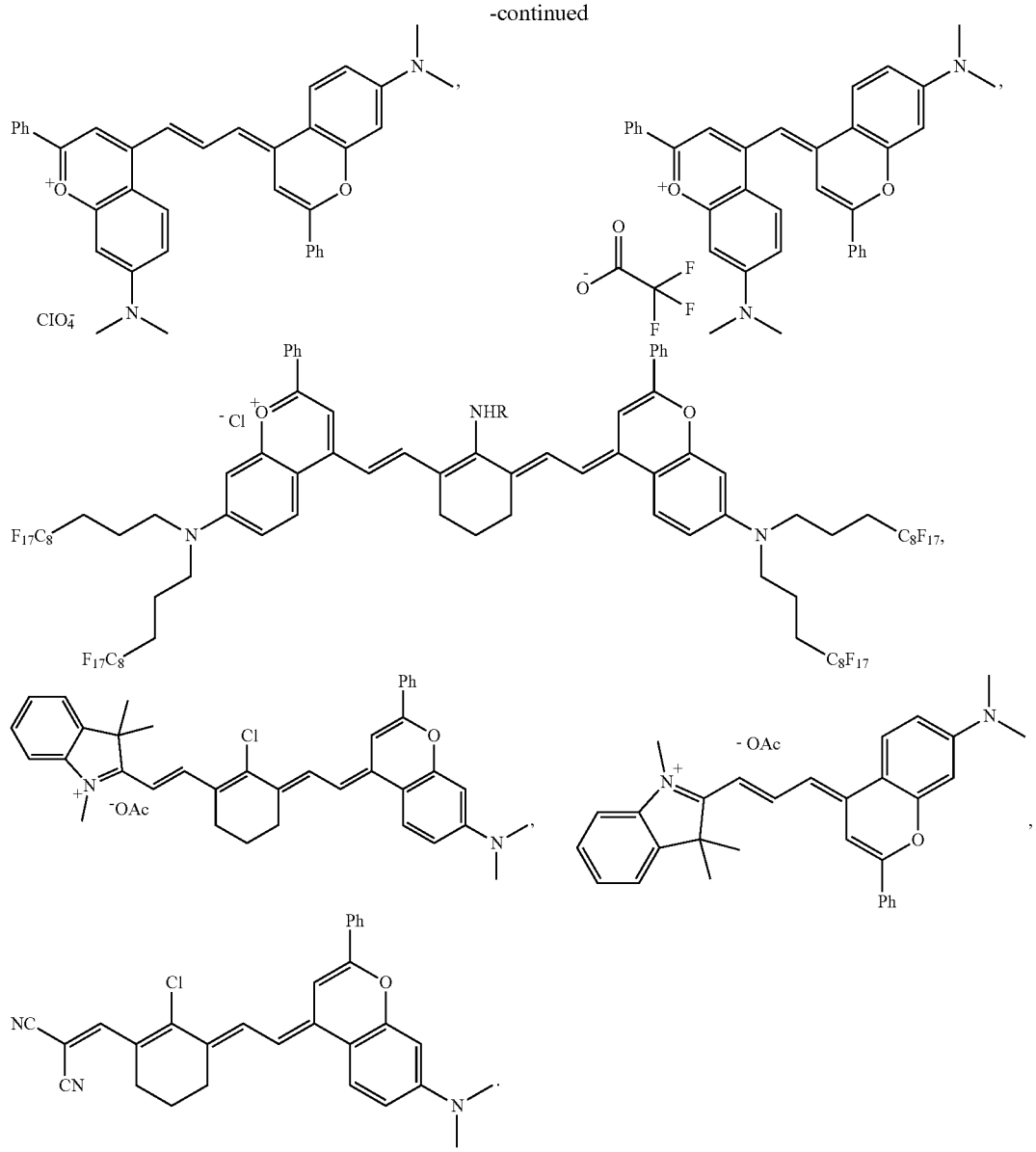

Other aspects, embodiments, and features will be apparent from the following description, the drawings, and the claims.

BRIEF DESCRIPTION OF THE DRAWINGS

FIGS. 1D-1F are schemes and data showing other embodiments of the flavylium polymethine dyes.

FIG. 3A shows an image of vials of IR-26, IR-1061 and Flav7 with matched optical density at 808 nm in dichloromethane, excited at 808 nm, collected using an InGaAs camera (1000-1500 nm). FIG. 3B shows average background subtracted camera intensity for ten frames normalized to exposure. FIG. 3C shows the absolute $\Phi_F$ of the 3 dyes.

DETAILED DESCRIPTION

Bright fluorophores in the near infrared and shortwave infrared (SWIR) are essential for imaging in complex environments. Herein, a panel of dimethylamino flavylium polymethine dyes are presented, which display significantly red-shifted spectra. Varying the methine chain from 1 to 7 carbons yields fluorophores with emission from 680 to 1045 nm. Further photophysical characterization reveals that mono- and tri-methine dyes display enhanced photostabilities and the penta- and hepta-methine dyes exhibit exceptional brightness for their respective spectral regions. A direct comparative imaging experiment in the SWIR is used to determine that the flavylium heptamethine dye is brighter than current polymethine dye standards for this region.

Exploiting the breadth of the electromagnetic (EM) spectrum has been critical in the development of an array of pervasive technologies that can be used simultaneously. This success is linked to the ability to control atoms and molecules through treatment with different energies of light. The utility of molecules that absorb at orthogonal wavelengths is overwhelmingly apparent by the impact of multiplexed optical microscopy.[1] These results have led to the development of a plethora of new fluorophores throughout the visible and near-infrared (NIR) regions of the EM spectrum.[2]

Figure 1A:
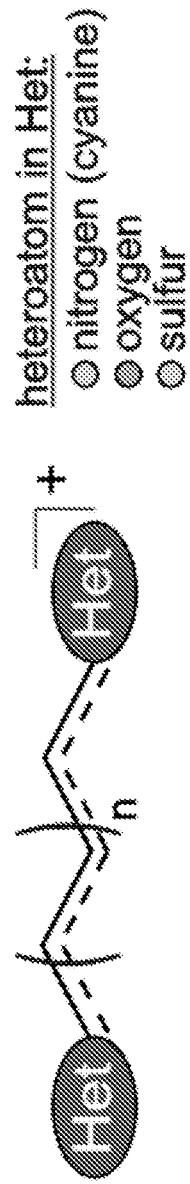
FIG. 1A shows a polymethine dye scaffold.
Figure 1B:
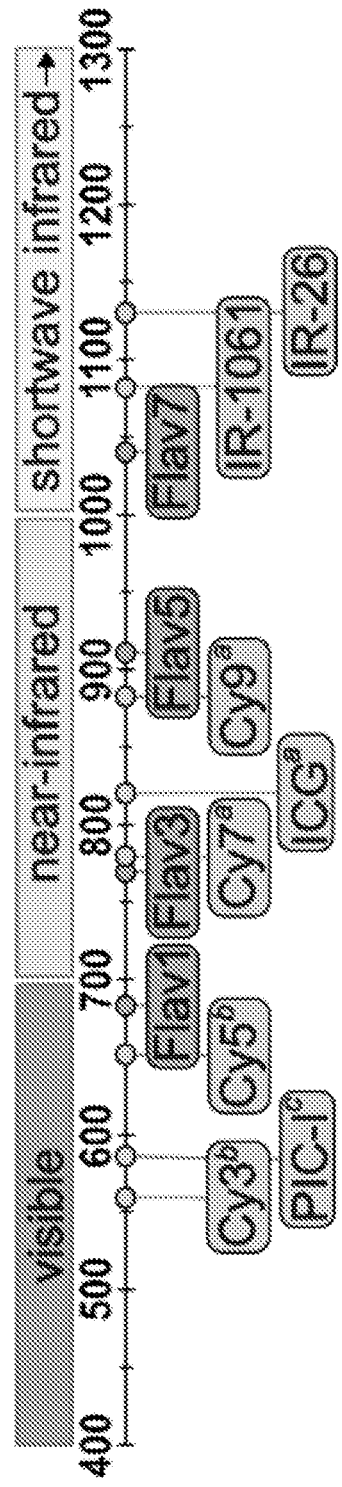
FIG. 1B shows $\lambda_{max,em}$ for selected polymethine dyes (see FIG. 4 for structures and citations) and the flavylium polymethine dyes in this work.

Polymethine dyes, one of the most broadly utilized fluorophore classes, are charged molecules composed of heterocycles linked by a methine chain (FIG. 1A). Those containing nitrogen heterocycles are deemed cyanine dyes. 1-, 3-, and 5-cyanines, where the number indicates the length of the methine chain, span the visible region, while 7-cyanines reach the NIR (700-900 nm)[3] (FIG. 1B). Polymethine dyes have found utility in many technologies including optical data storage, dye-sensitized solar cells, optical switching, microarrays, live cell microscopy, and clinical imaging.[2,4] Further engineering has led to uncaging strategies for drug delivery and sensing.[3,5]

Significant interest has centered on developing red-shifted fluorophores due to decreased light scattering and low absorbance and emission of naturally occurring substances in the NIR. Recently, Dai and coworkers have shown that moving beyond the traditional NIR (classified as NIR-I) to the shortwave IR (SWIR, 1000-2000 nm), also referred to as NIR-II, is superior for optical imaging in animals and tissue.[6] The SWIR has also been recognized as a valuable region for night vision, optical coherence tomography, moisture detection, quality control, and optical communication as these wavelengths traverse readily through the environment.[4c,7] Collectively, these applications indicate that the currently underutilized NIR-II/SWIR is poised to become a prominent area of the EM spectrum for technological advances. However, for this potential to be realized, molecules and materials that orthogonally absorb and emit shortwave infrared light are necessary.

While cyanines have been the premier polymethine dyes for applications in the visible and NIR, their extension into the SWIR has been limited. Lengthening the polymethine chain, a reliable strategy for bathochromically-shifting cyanine dyes, can compromise the fluorescence quantum yield ($\Phi_F$), decrease fluorophore stability, and lead to loss of electron delocalization over the entire conjugated system.[8] Thus, heterocycle modification is vital for the creation of bright, stable polymethine dyes in the SWIR. See FIG. 1C, which exemplifies synthesis of dimethylamino flavylium polymethine dyes 3-6 (Flav1, Flav3, Flav5, Flav7).

The photophysical changes that result from heterocycle modification are less straightforward than polymethine extension, yet trends have been inferred. Extending heterocycle conjugation or adding electron-donating groups have been shown to bathochromically-shift polymethine dyes.[8a,b,9] Alternately, varying the heteroatom from oxygen down the chalcogens results in red-shifted absorption of ~30-100 nm for each step, although the emission is compromised by increased intersystem crossing due to spin-orbit coupling.[10] Here, a heterocycle for polymethine dyes is presented, which imparts significant bathochromic shifts while retaining emissive properties. Drexhage and coworkers' reports regarding oxygen and sulfur-containing heptamethine dyes with excellent photostabilities and absorbances in the NIR and SWIR.[11] This work yielded thiaflavylium dye IR-26, the benchmark fluorophore for this region. IR-26 has a $\lambda_{max,abs}$ at 1080 nm and a weak emission at 1190 nm. Given the low $\Phi_F$ of IR-26, heterocycles are employed that contain only first and second row elements, yet furnish NIR and SWIR emitters. Reported alongside IR-26 was the oxygen analog IR-27, which has a $\lambda_{max,abs}$ at 985 nm.[11] IR-27 was hypothesized, without heavy atoms, would have a higher $\Phi_F$ and that its emission could be further red-shifted with electron donating functionality. Thus, attention was directed to the synthesis of dimethylamino flavylium polymethine dyes.

Figure 1C:
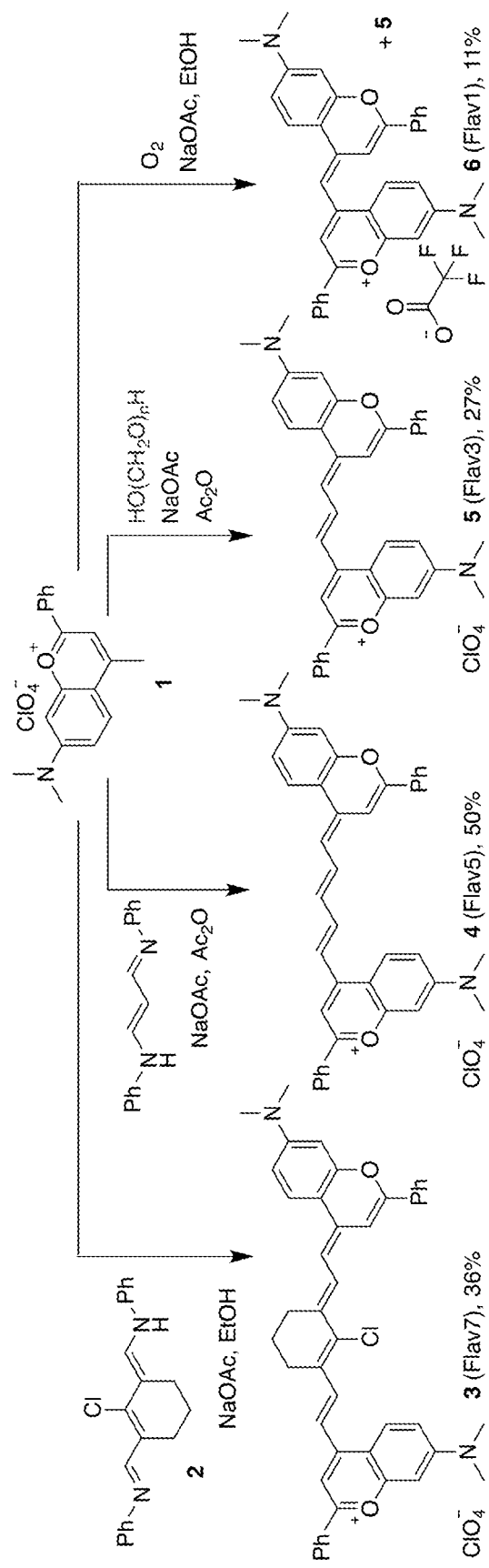
FIG. 1C is a scheme showing flavylium polymethine dyes.
Figure 1E:
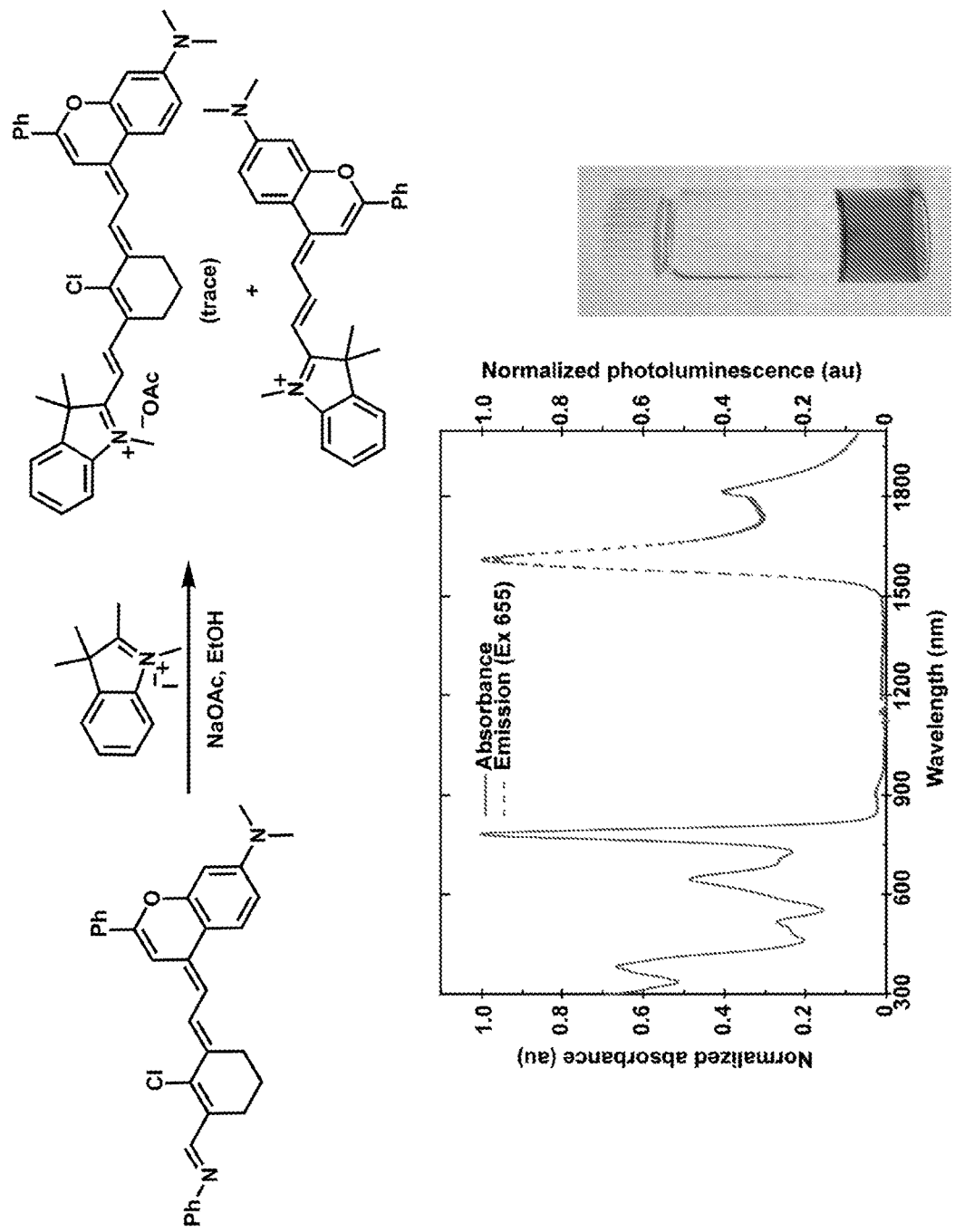
Figure 1F:
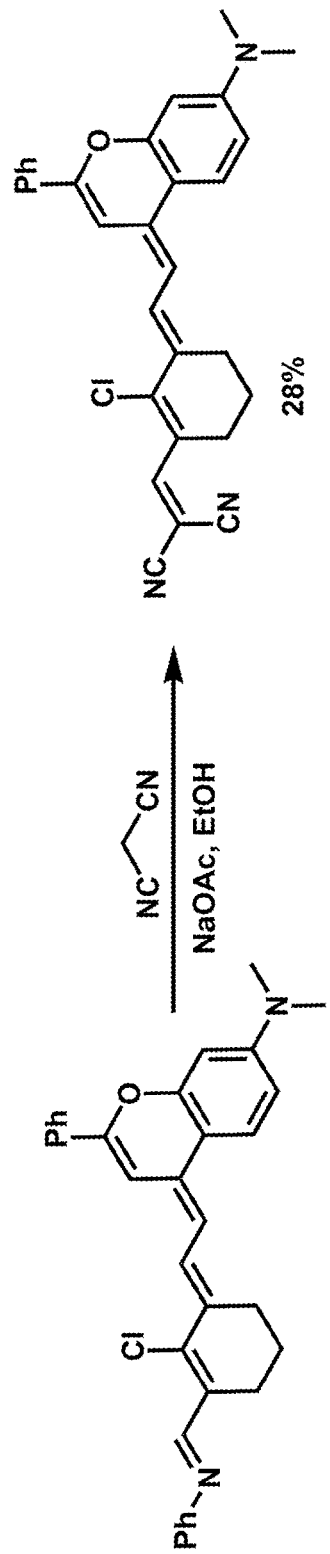
Figure 1F:
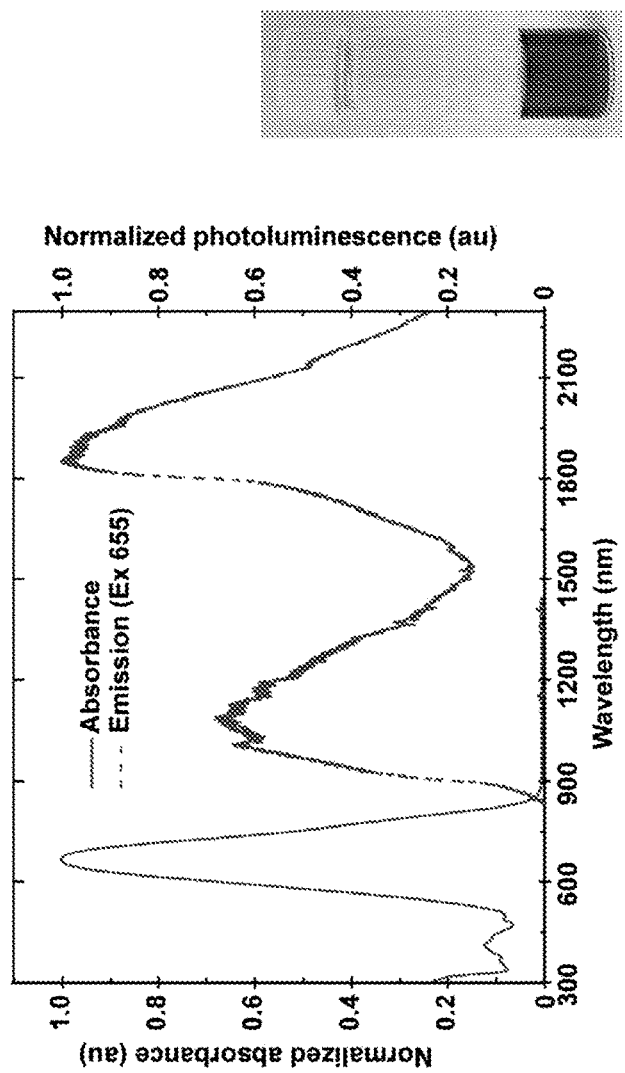
Figures 5A, 5B:
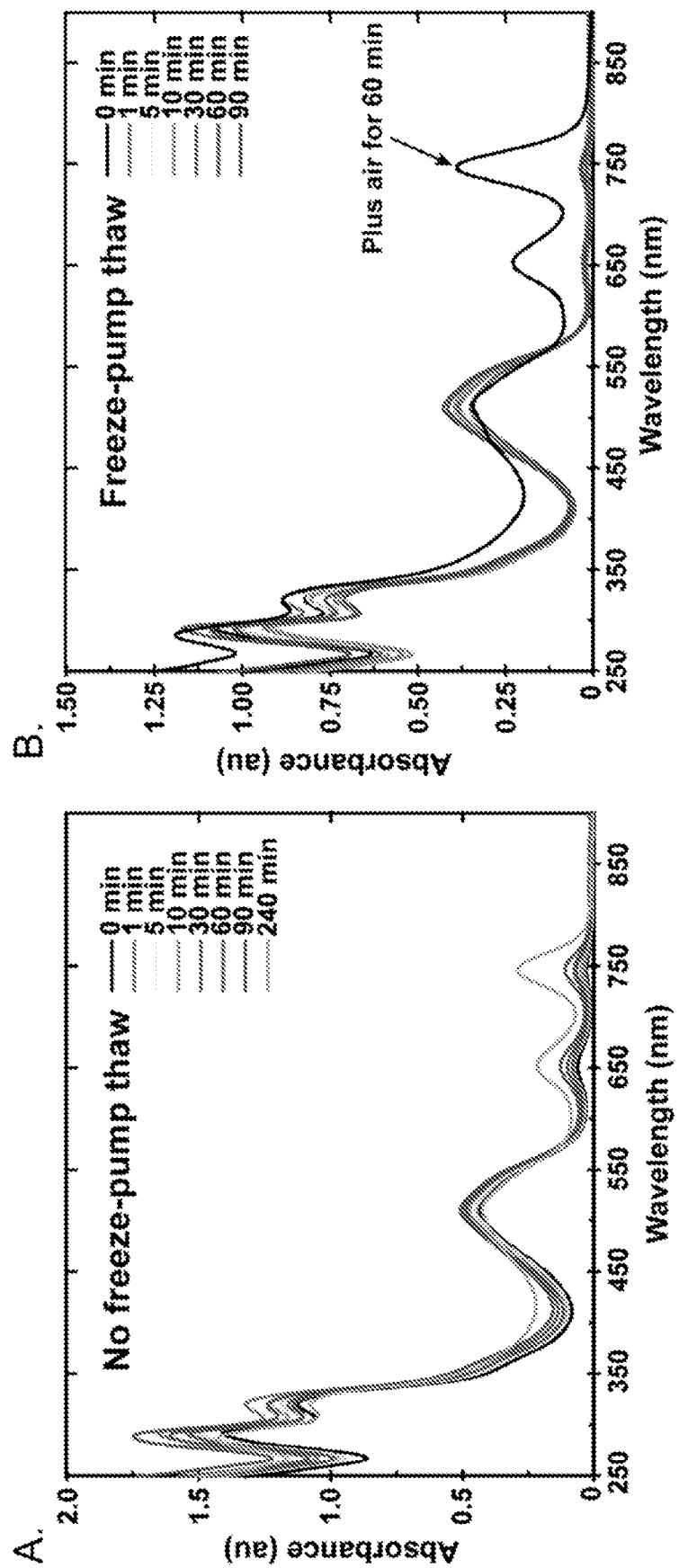
FIGS. 5A-5B show absorbance traces (in DCM) monitoring the reaction of flavylium (1) with excess sodium acetate in ethanol with (B) and without (A) freeze-pump thawing. The absorbance peaks at 650 nm and 740 nm indicate that Flav1 (6) and Flav3 (5) are produced in (A) when oxygen is present, but minimal reaction is observed in (B), until the addition of air, at which point both dye species are observed.
Figure 6:
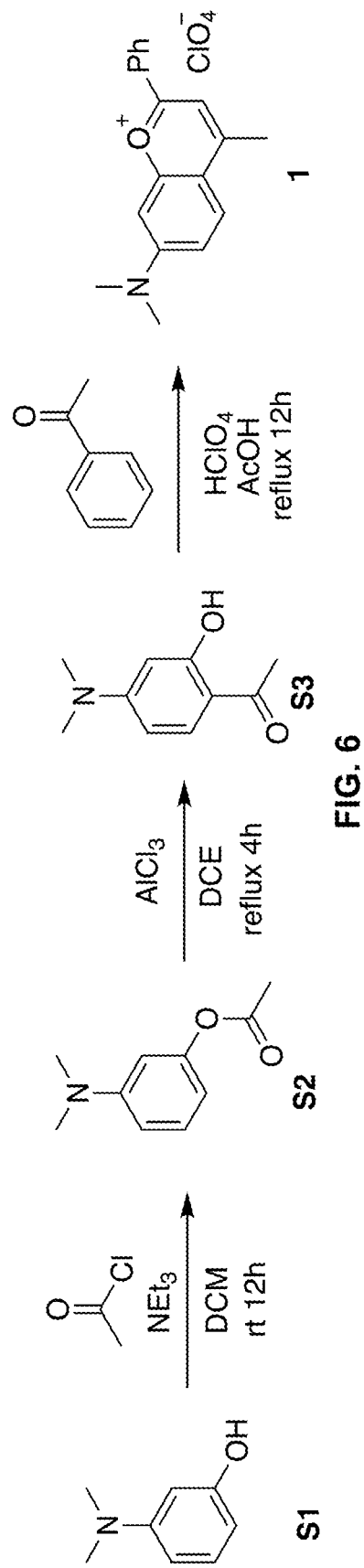
FIGS. 6 and 7 are schemes showing synthetic details for the compounds described herein.
Figure 7:
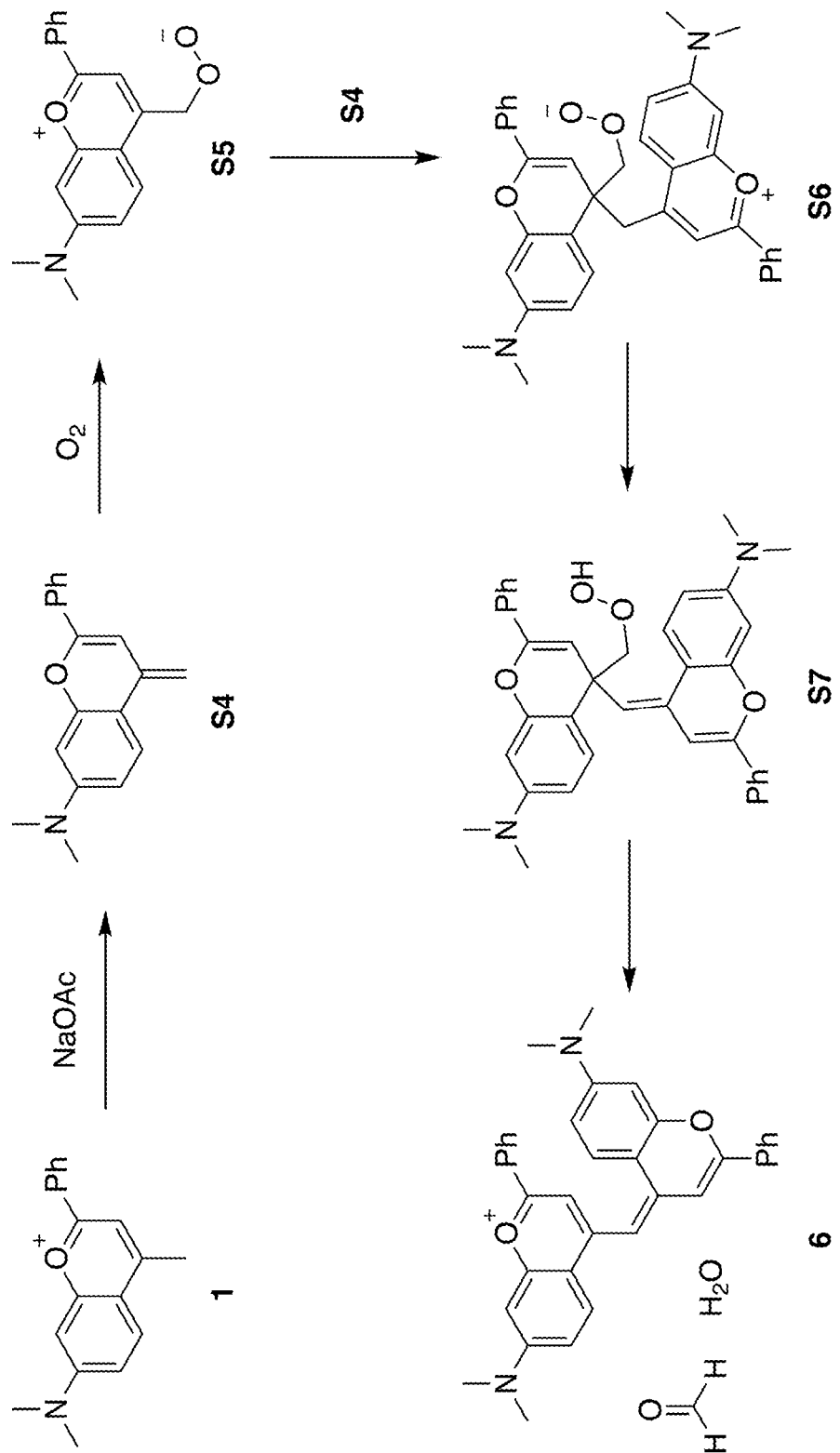
Figure 8:
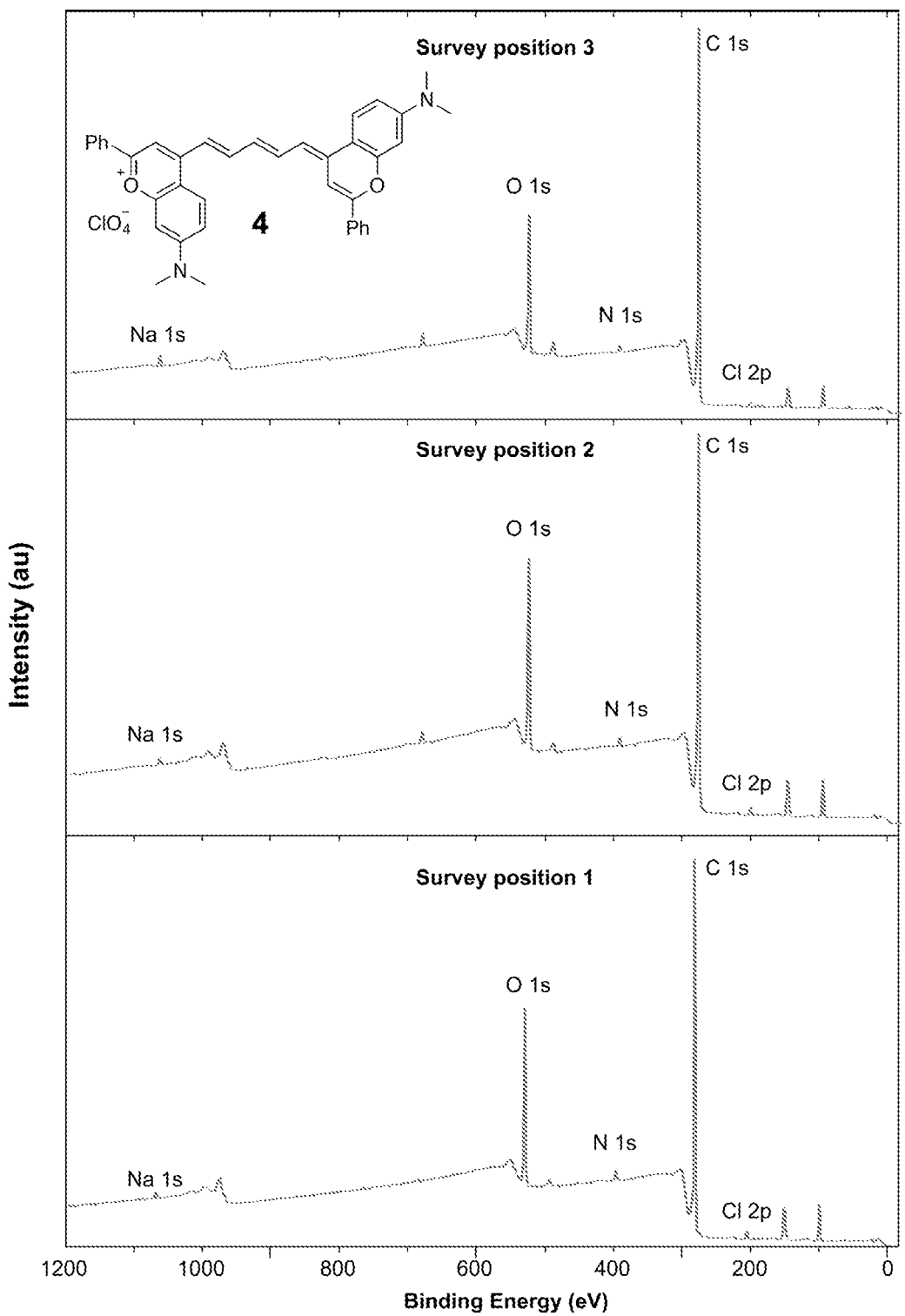
FIGS. 8-33 represent supporting data and spectral information relating to the compounds and experiments described herein.
Figure 9:
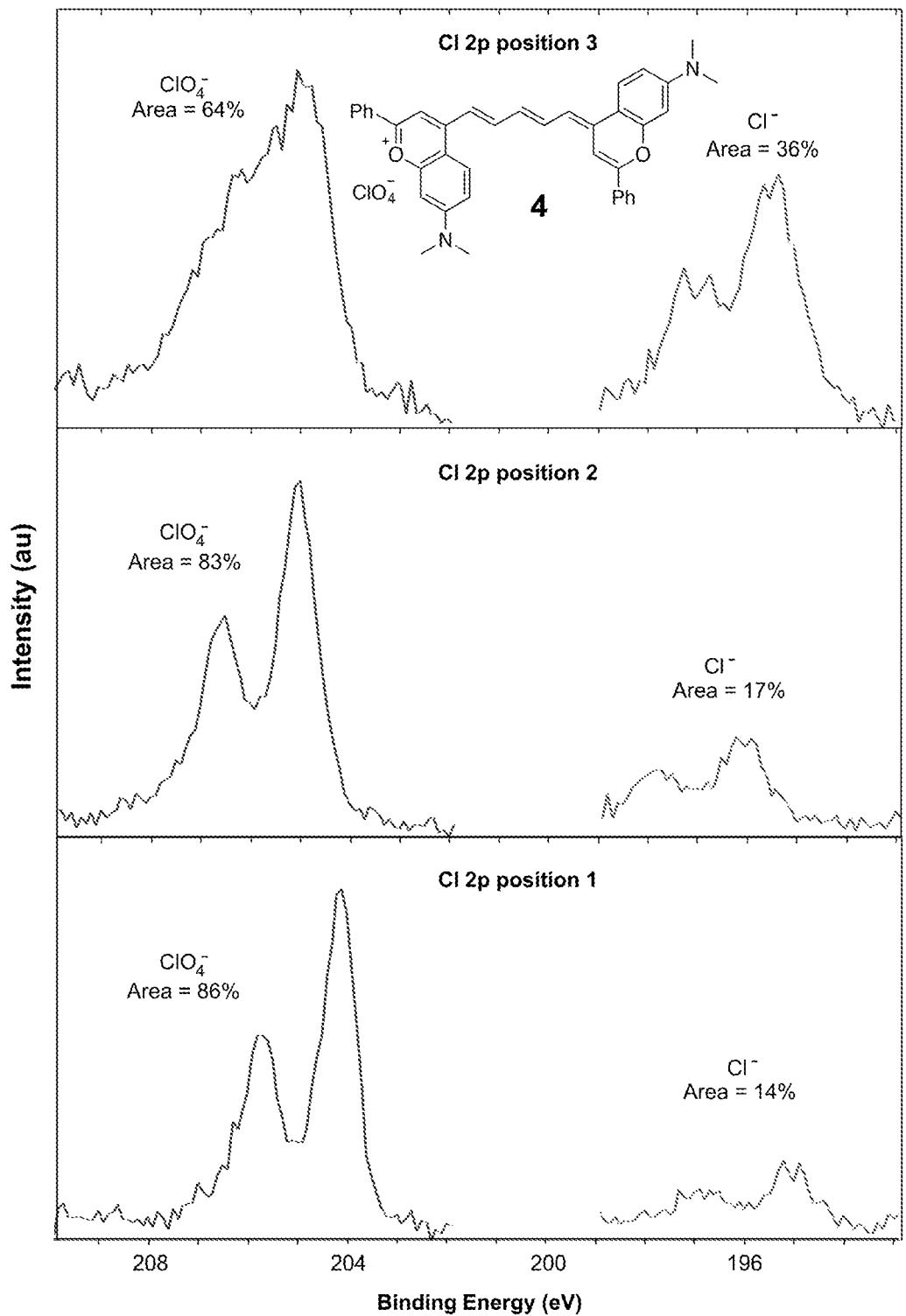

Polymethine dyes are prepared through the introduction of an activated heterocycle to an aldehyde or bis-aldehyde equivalent. The requisite 7-N,N-dimethylamino-4-methyl-flavylium heterocycle (1) was prepared in three steps from dimethylaminophenol as previously reported (FIG. 6, depicting Synthesis of 7-N,N-dimethylamino-4-methyl-flavylium perchlorate 1). See, Chen, J.-R.; Wong, J.-B.; Kuo, P.-Y; Yang, D.-Y. Org. Lett. 2008, 10, 4823-4826, which is incorporated by reference in its entirety. Combining 1 with N-[(3-(anilinomethylene)-2-chloro-1-cyclohexen-1-yl) methylene] aniline 2, malonaldehyde bis(phenylimine), and paraformaldehyde under basic conditions yielded dimethylamino flavylium dyes 3, (Flav7), 4 (Flav5), and 5 (Flav3), respectively (FIG. 1C, Scheme 1). The formation of 3 proceeded in anhydrous ethanol with sodium acetate and 2. Under these conditions, a mixture of highly colored products was obtained which included Flav7 and surprisingly Flav3 and 6 (Flav1). Treatment of 1 with base in ethanol, without an electrophile, allowed access to a mixture of 6 and 5. This was determined to be an oxygen dependent transformation (FIGS. 5A-5B) and hypothesize that the oxygen undergoes radical addition to the flavylium to generate a peroxyflavylium which combines with deprotonated 1 to yield Flav1 and an equivalent of formaldehyde (FIG. 7, showing mechanistic hypothesis for the formation of Flav1 6). The Flav3 can then be formed via the combination of formaldehyde and 1. With this knowledge, the syntheses of 4-5 was optimized to proceed in deoxygenated acetic anhydride. The perchlorate counterions in 3-5 were confirmed by X-ray photoelectron spectroscopy (FIGS. 8-9, depicting X-ray photoelectron spectra survey scan of three locations of Flav5 (4) sample and high-resolution X-ray photoelectron scan of the binding energies from 193-210 eV, showing distinct peaks for $ClO_4^-$ and $Cl^-$ at three locations on the sample of 4, respectively.

The presence of Cl⁻ is rationalized by the coexistence of Na+. The relative increase in area % of Cl– in position 3 is accompanied by an increase in Na+ content at position 3 (FIG. 8, 0.37 atomic % Na in position 3 vs 0.23 atomic % Na in positions 1 and 2). These data support that $ClO_4^-$ is retained as the counterion throughout the synthesis).

Figure 2:
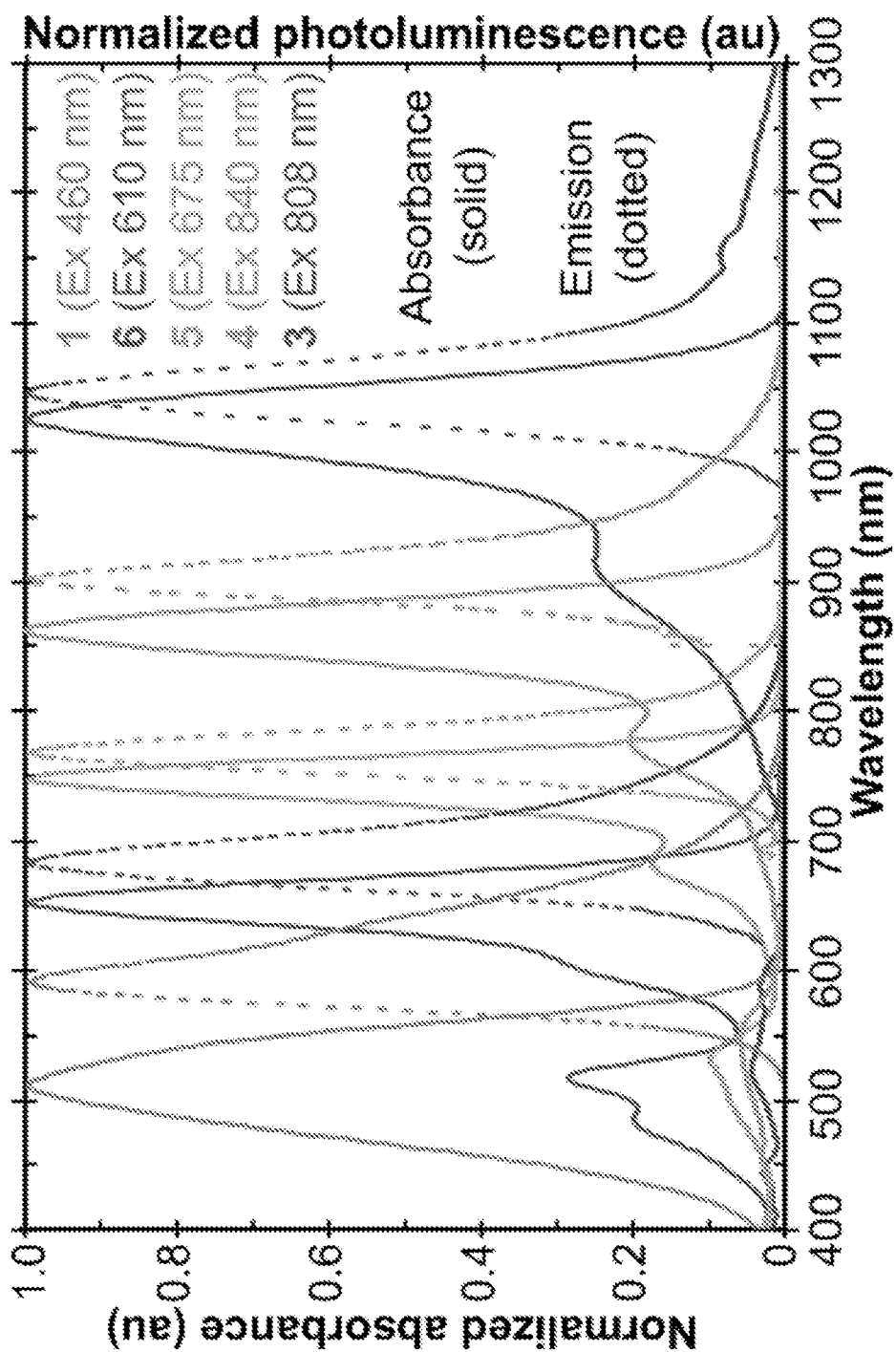
FIG. 2 shows normalized absorbance (solid) and photoluminescence (dotted) of 5, 7-10 in dichloromethane.
Figure 4:
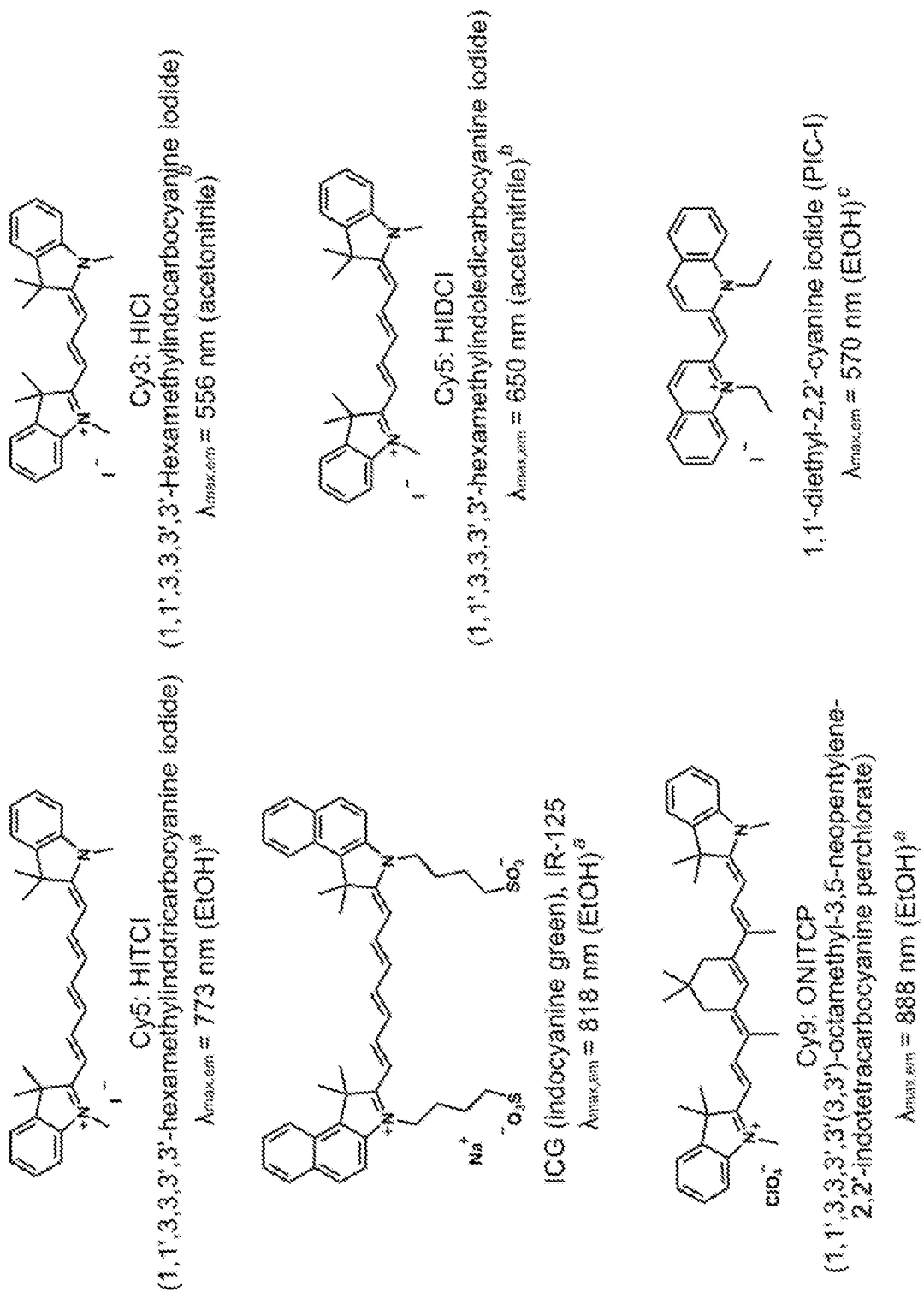
FIG. 4 shows dye structures and emission maxima for FIGS. 1A-1C. See, for example, [a]Rurack, K.; Spieles, M. Anal. Chem. 2011, 83, 1232-1242; [b]Sato, S.; Tsunoda, M.; Suzuki, M.; Kutsuna, M.; Takido-uchi, K.; Shindo, M.; Mizuguchi, H.; Obara, H.; Ohya, H. Spectrochim. Acta— Part A Mol. Biomol. Spectrosc. 2009, 71, 2030-2039; [c]Guarin, C. A.; Villabona-Monsalve, J. P.; López-Arteaga, R.; Peon, J. J. Phys. Chem. B 2013, 117, 7352-7362, each of which is incorporated by reference in its entirety.
Figure 10:
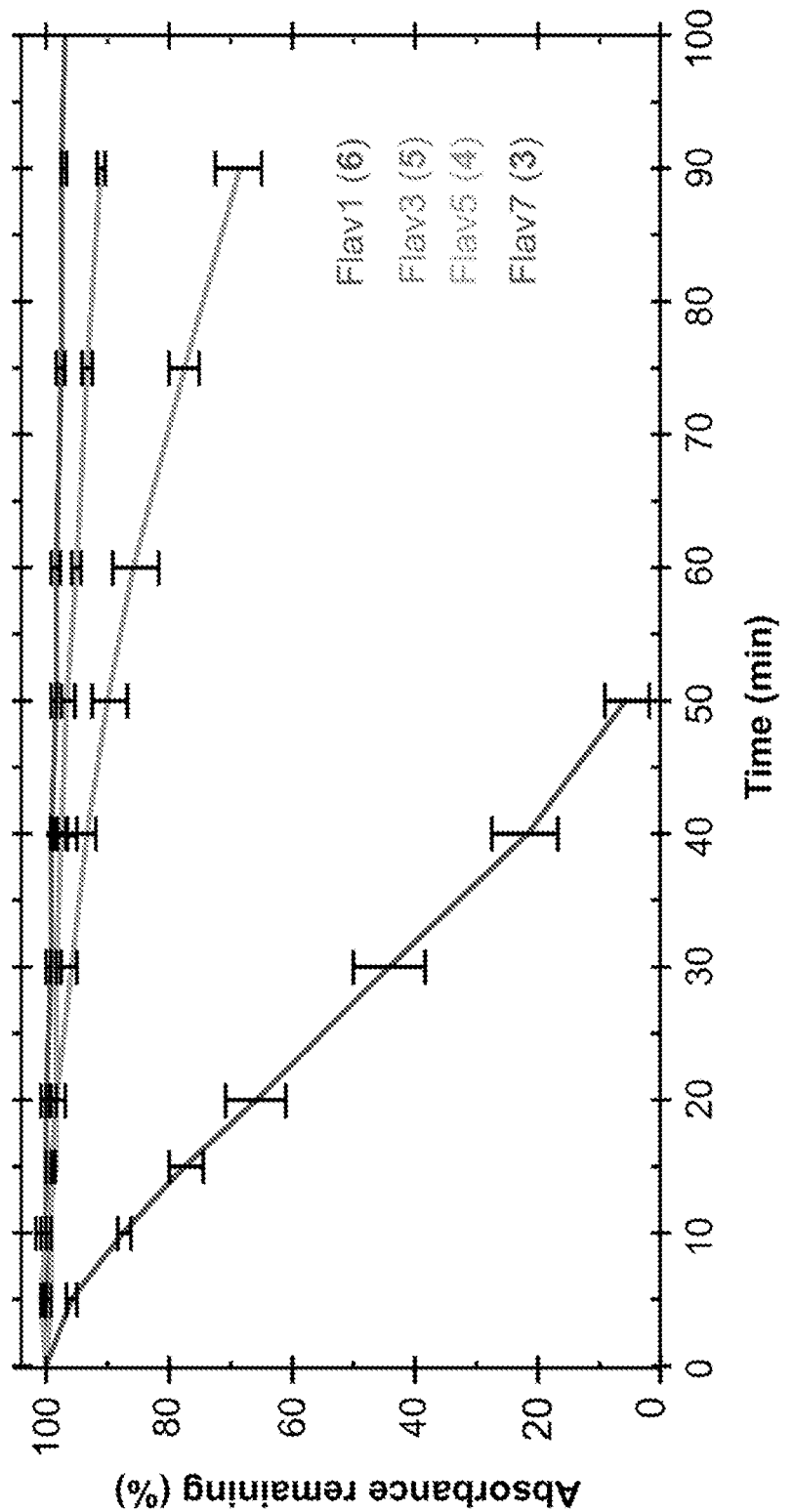
Figure 11:
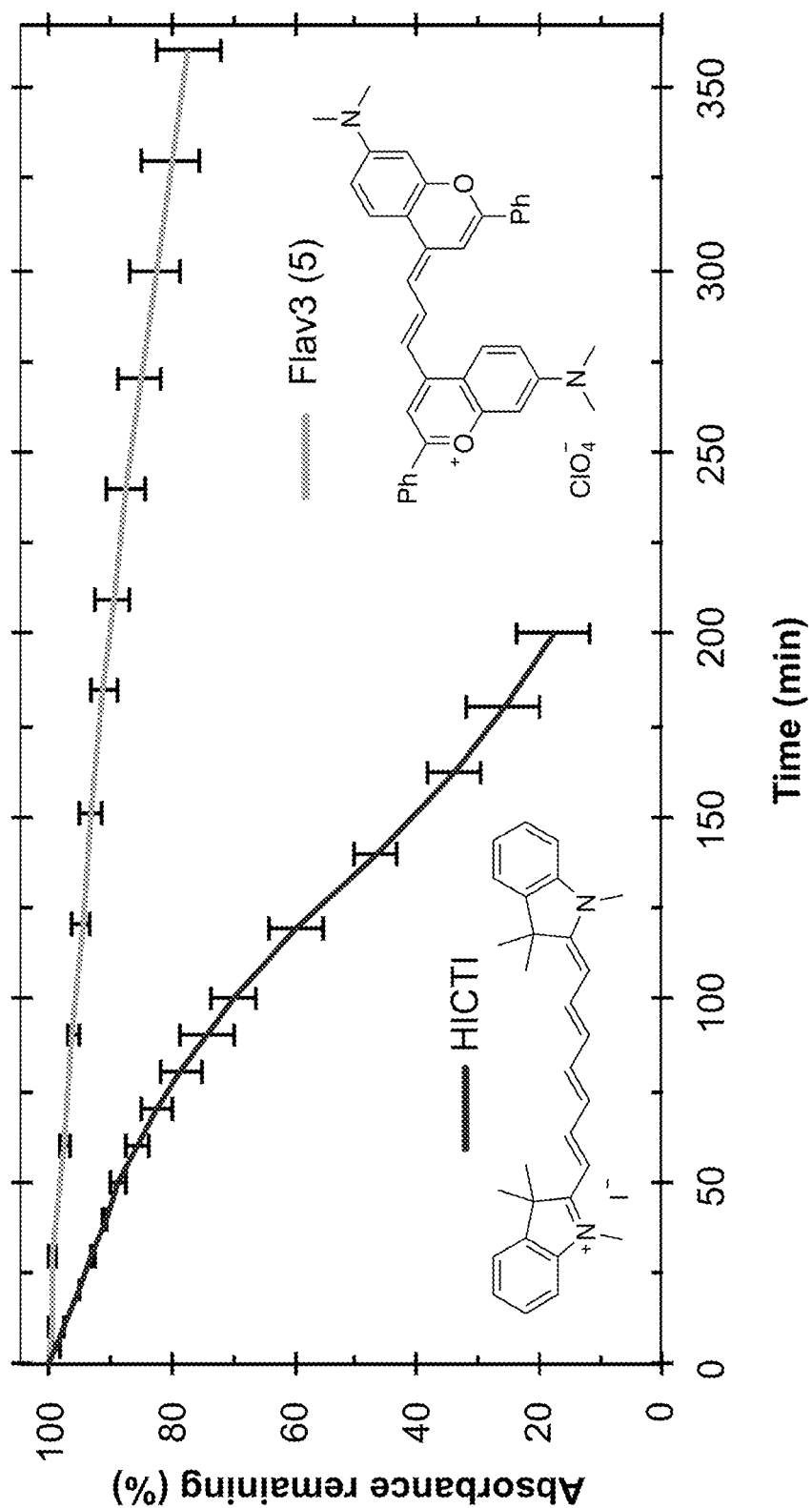

With flavylium dyes 3-6 in hand, their absorption, emission, and photostability properties were measured. As seen in FIG. 2 and Table 1, the flavylium dyes span the long wavelength end of the visible, the NIR and enter the SWIR. The dimethylamino flavylium dyes are significantly red-shifted from classic cyanine dyes by approximately 200 nm (FIG. 1B) and the Flav7 absorbs ~40 nm past IR-27. Photostabilities of the Flav series were measured under continuous-wave irradiation (532 nm, 0.53 fluence). Flav1, Flav3 and Flav5 all show excellent photostabilities in dichloromethane, with Flav7 displaying reasonable stability (Table 2, FIG. 10m, depicting photobleaching of 3-6. Dyes in dichloromethane were irradiated with a 532 nm laser, at 0.53±0.05 Wcm⁻² fluence and monitored by decreasing absorbance at $\lambda_{max,abs}$). The Flav1 dye absorbs at 650 nm, similar to a 5-cyanine, but has a lower extinction coefficient (ε) and $\Phi_F$, resulting in a low quantum efficiency (QE, defined as $\varepsilon\Phi_F$), consistent with the short polymethine chain. See, Ishchenko, A. A. *Russ. Chem. Rev.* 1991, 60, 1708-1743, which is incorporated by reference in its entirety. The Flav3 dye has similar absorption properties to the standard heptamethine indocyanine dye 1,1',3,3,3',3'-hexamethylindotricarbocyanine iodide (HITCI, Cy7) with $\lambda_{max,abs}$~745 nm and ε~220,000 M⁻¹ cm⁻¹. While HITCI has ~10-fold higher $\Phi_F$ than Flav3, Flav3 is 4-fold more photostable (Table 4, FIG. 10 depicting photobleaching of Flav3 (5) and 1,1',3,3,3',3'-hexamethyl-indotricarbocyanine iodide (HITCI) (Sigma Aldrich). Dye solutions in dichloromethane were irradiated with a 1050 nm LED with 4.6 mWcm⁻² fluence). See, for example, Hatami, S.; Würth, C.; Kaiser, M.; Leubner, S.; Gabriel, S.; Bahrig, L.; Lesnyak, V.; Pauli, J.; Gaponik, N.; Eychmüller, A.; Resch-Genger, U. *Nanoscale* 2015, 7, 133-143, which is incorporated by reference in its entirety. The Flav5 and Flav7 dyes are more red-shifted than indoline-containing cyanine dyes, absorbing at 862 nm and 1026 nm, respectively. The Flav5 emits at 908 nm, a relatively unique wavelength for polymethine dyes, with extremely high QE (10³ M⁻¹ cm⁻¹), desirable photostability, and the largest Stoke's shift of the series at 46 nm. Finally, the Flav7 is a true NIR-II/SWIR fluorophore with emission at 1061 nm, $\Phi_F$ of 0.53%, and an impressive SWIR QE of 1,200 M⁻¹ cm⁻¹.

TABLE 1

Photophysical characterization of 1, 3-6.

| | absorption (DCM) | | emission (DCM) | | QE, $\varepsilon\Phi_F$ |
|---|---|---|---|---|---|
| | $\lambda_{max}$ (nm) | ε (M⁻¹cm⁻¹)[a] | $\lambda_{max}$ (nm) | $\Phi_F{}^a$ | (M⁻¹cm⁻¹) |
| 1 | 510 | 17 000 | 587 | — | — |
| 6 | 650 | 16 000 | 684 | 0.7% | 100 |
| 5 | 746 | 220 000 | 766 | 2.9% | 6 600 |
| 4 | 862 | 240 000 | 908 | 5% | 10 000 |
| 3 | 1026 | 236 000 | 1045 | 0.53% | 1 200 |

[a]see SI for ε and $\Phi_F$ errors

TABLE 2

Photobleaching rates of 3-6.

| | raw rate, k (s⁻¹ × 10⁻³) | ε at 532 nm (M⁻¹cm⁻¹ × 10⁴) | relative rate, $k_{rel}$ (s⁻¹ × 10⁻³) |
|---|---|---|---|
| 6 | 0.43 ± 0.01 | 0.23 ± 0.08 | 4 ± 1 |
| 5 | 1.00 ± 0.06 | 2.0 ± 0.1 | 1.00 ± .06 |
| 4 | 2.6 ± 0.2 | 1.29 ± 0.08 | 4.0 ± 0.2 |
| 3 | 28. ± 3. | 1.4 ± 0.2 | 40. ± 6. |

Figure 12:
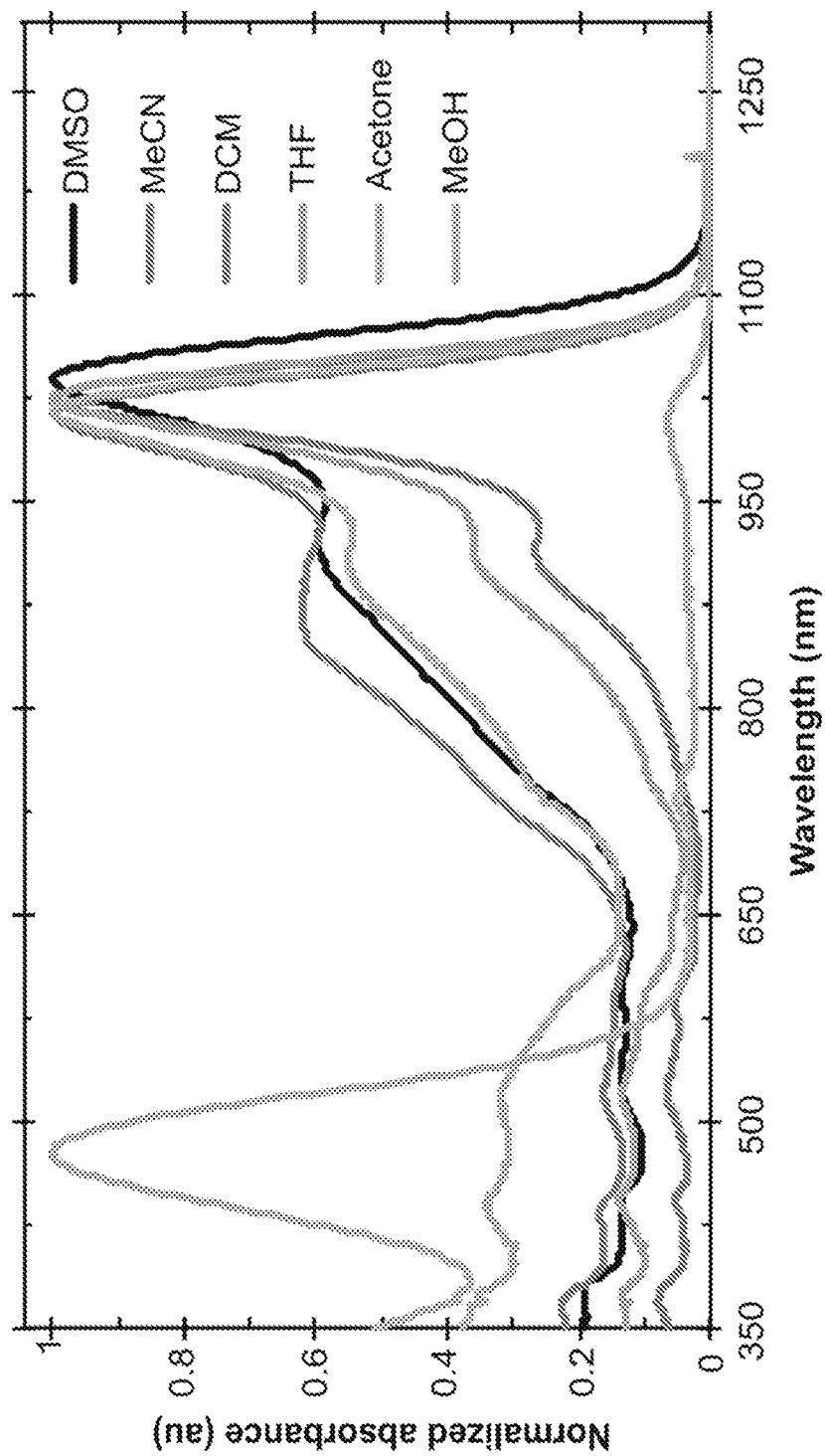
Figure 13:
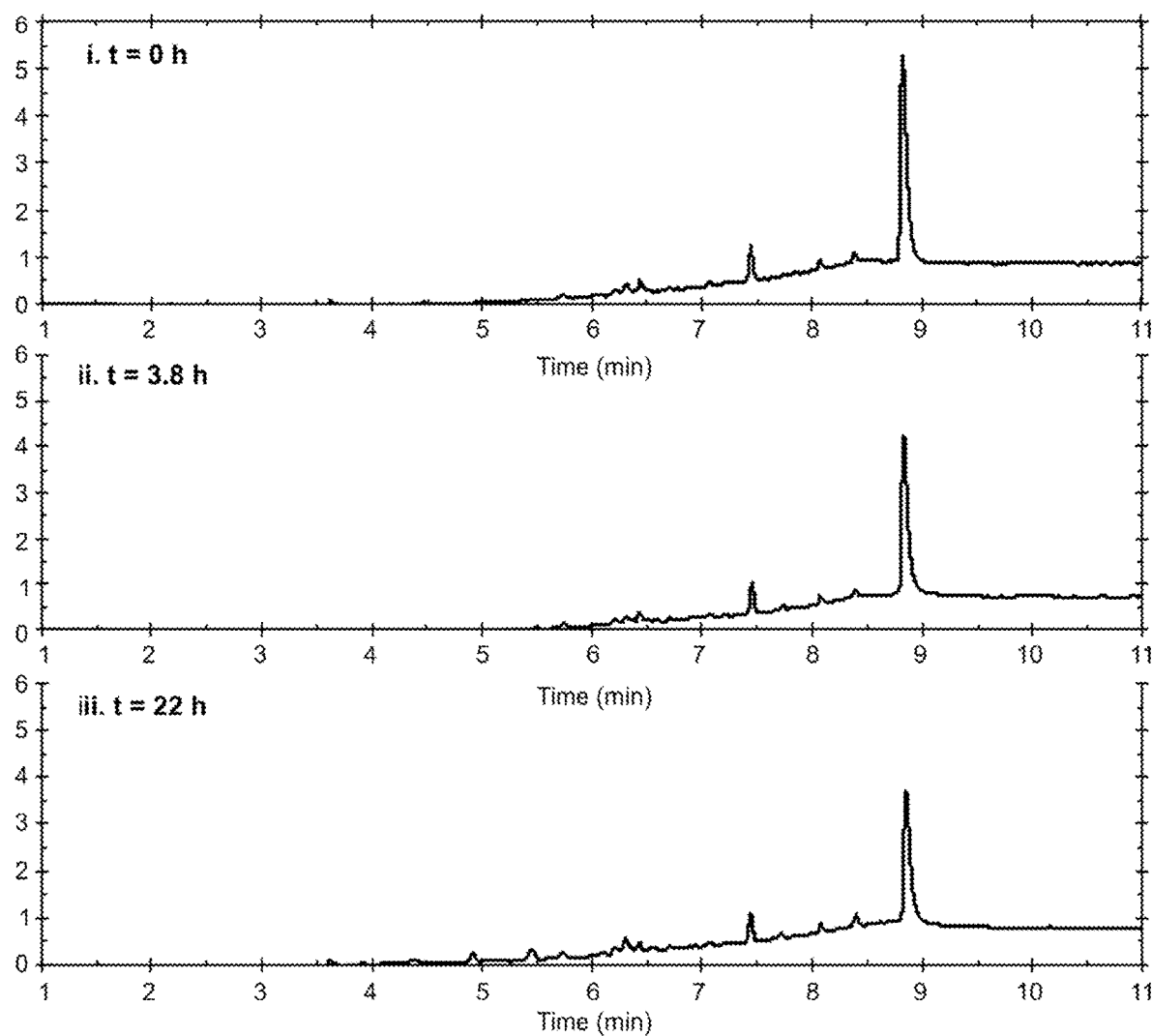

As highlighted above, this new family of flavylium dyes has photophysical qualities that are complementary to commonly used cyanine dyes. However, the premier dye in the series is the Flav7 (3) as few emissive polymethine dyes exist in this region. Thus, its stability was thoroughly investigated. First, the solvatochromism of Flav7 was explored. The $\lambda_{max,abs}$ in dichloromethane, dimethyl sulfoxide, acetonitrile, tetrahydrofuran, acetone exhibited minimal variation (Table 3, FIG. 12 depicting normalized absorption spectra of Flav7 (3) in several solvents. The concentrations used were 2-10×10⁻⁵ M.). However, in polar solvents, spectral broadening and accentuation of a high-energy shoulder were observed. This behavior is consistent with SWIR polymethine dyes that experience ground state symmetry breaking due to stabilization of an asymmetric electronic structure.[14] In methanol, an immediate color change is observed, suggestive of covalent modification of the polymethine; however, a major decomposition product could not be identified (FIG. 13 depicting chromatograms of solutions of Flav7 in 1% methanol/99% water monitored over time at 254 nm).

Figure 14:
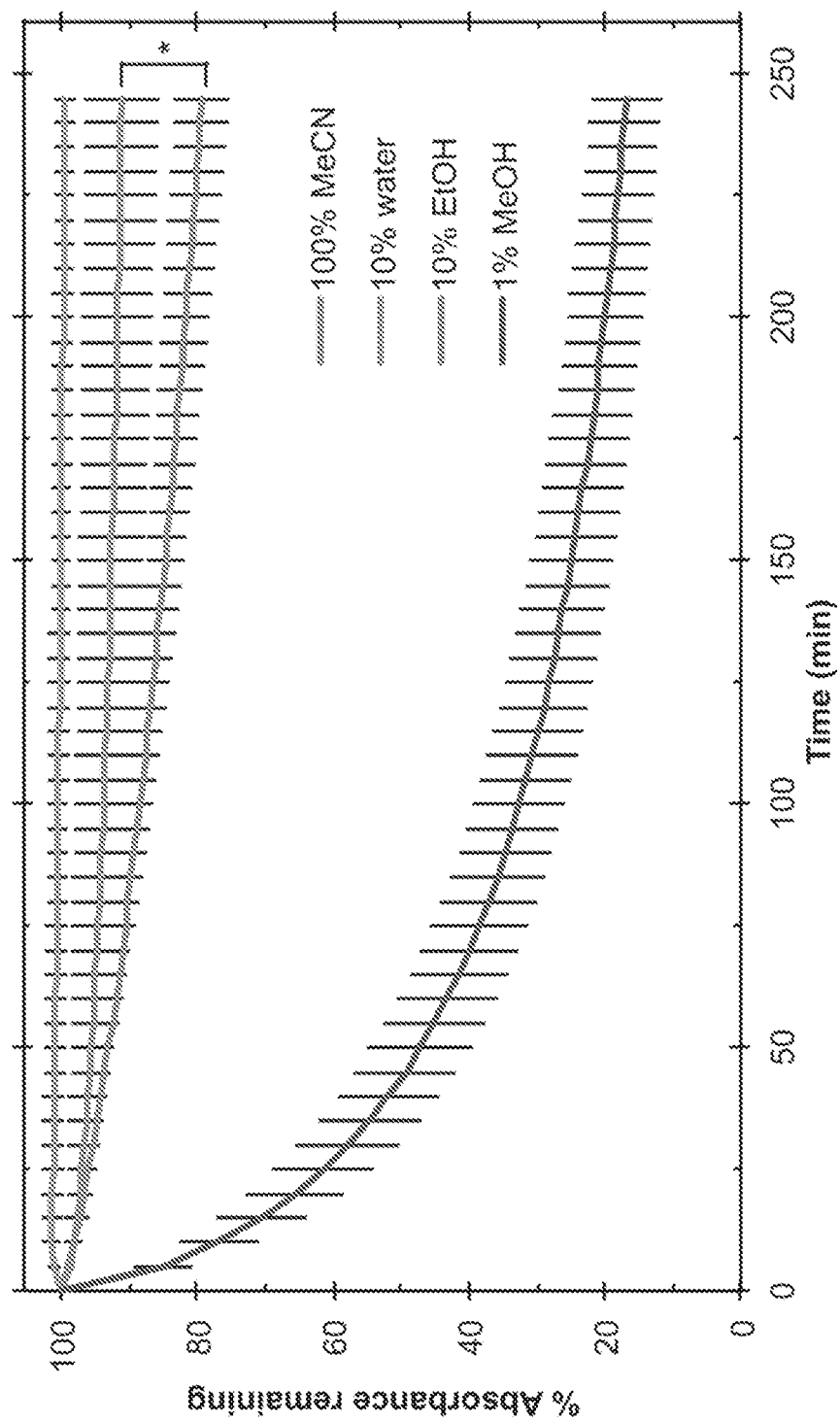
Figure 15:
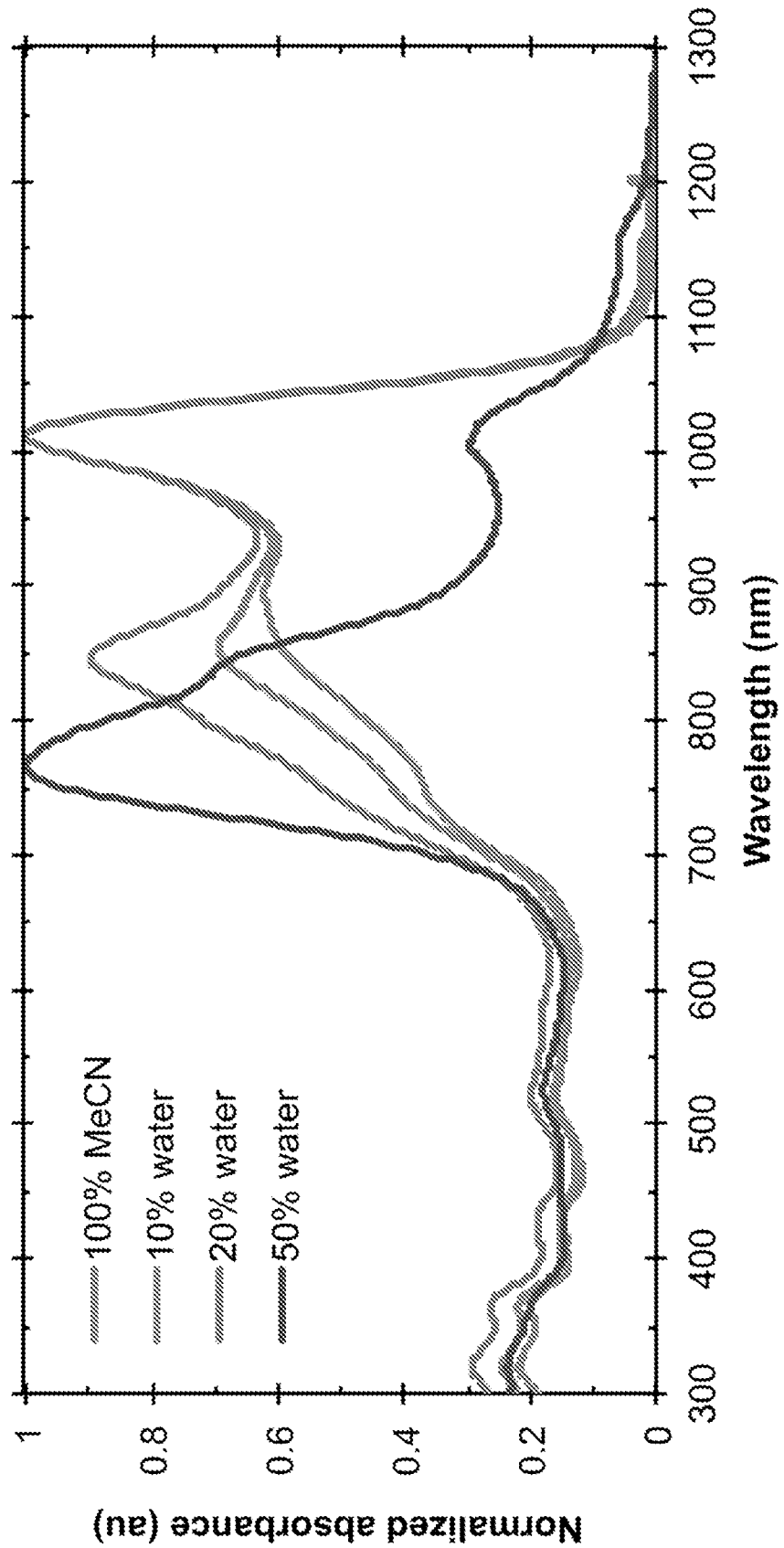
Figure 16:
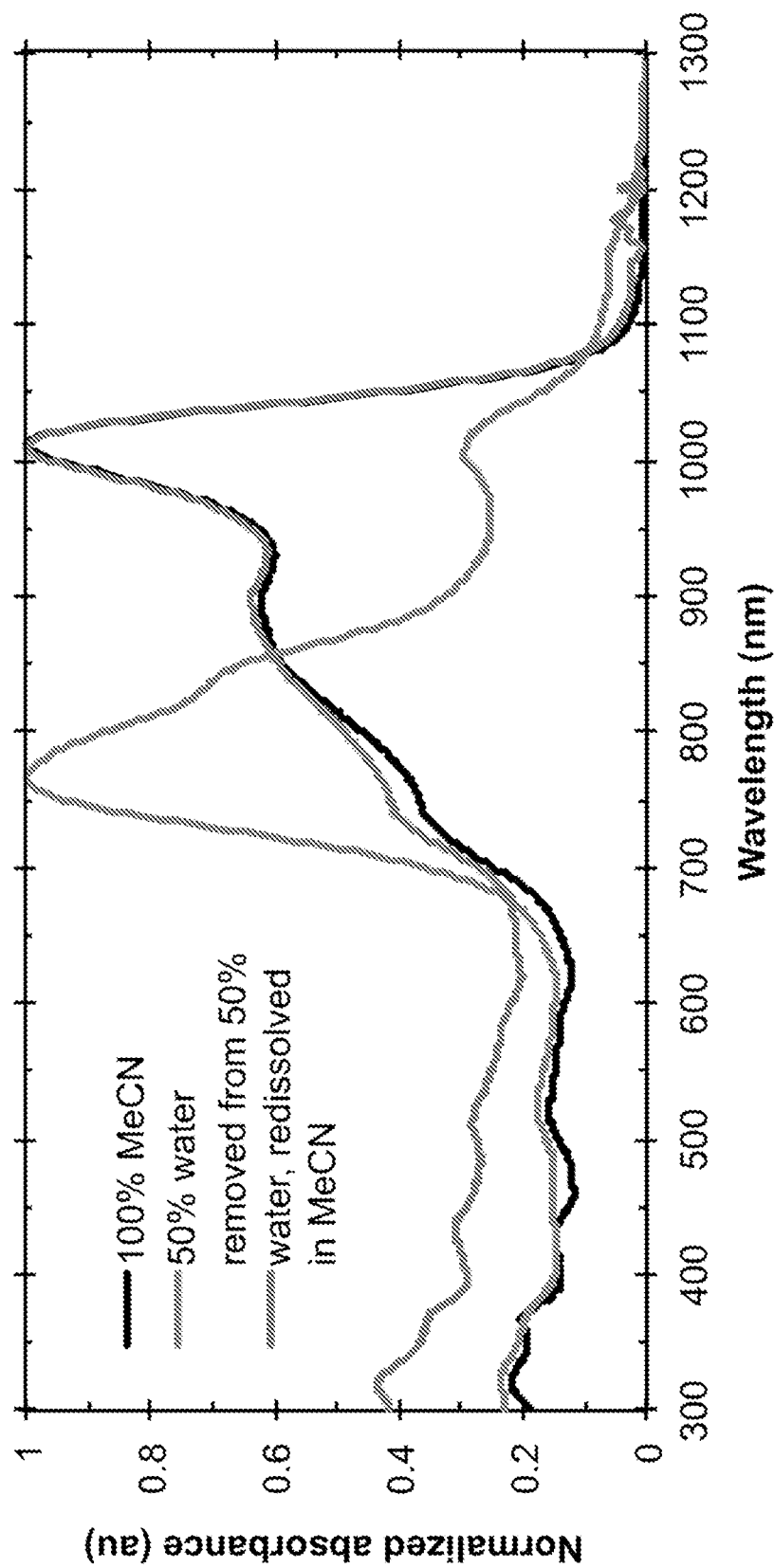
Figure 17:
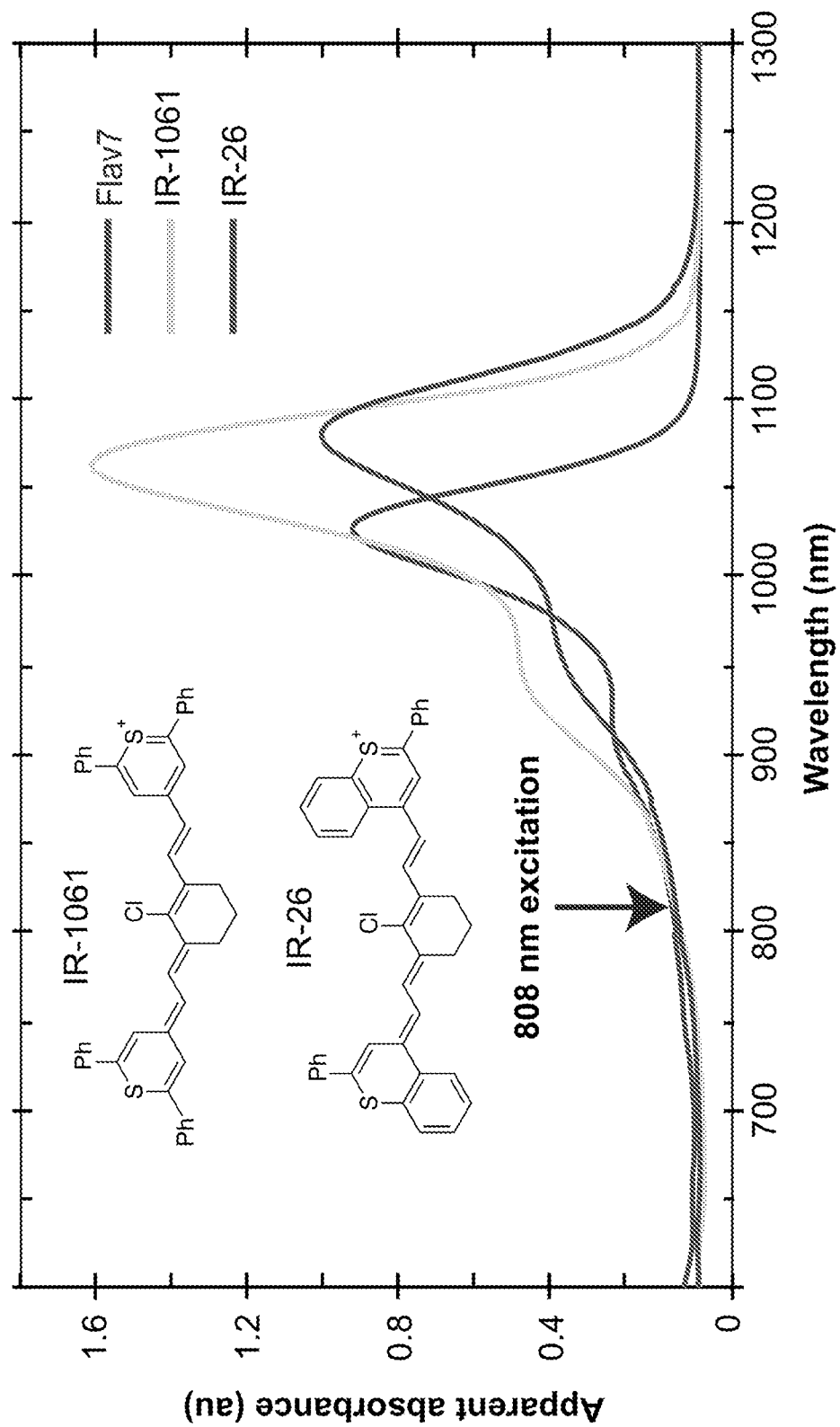

Concerned about the structure's susceptibility to nucleophilic attack, the stability of Flav7 in the presence of methanol, ethanol, and water was investigated. 3 was dissolved in acetonitrile, introduced 1-50% water, ethanol, or methanol, and monitored changes in absorption spectra over time. Consistent with the solvatochromism study, even 1% methanol resulted in the rapid loss of $\lambda_{max,abs}$ at 1013 nm. In contrast, adding 10% ethanol or water resulted in slight loss and no significant change, respectively, over 4 hours (FIG. 14 depicting stability of Flav 7 (3) in 100% MeCN (blue), and MeCN with 10% water (red), 10% EtOH (green), and 1% MeOH (purple), as measured by loss of absorbance at 1026 nm. Error represents standard deviation. * denotes p≤0.015), indicating that Flav7's reactivity with methanol is unique. Further evidence that 3 is stable to water include UV/Vis monitoring of the dose-dependent addition of water to 3 in acetonitrile followed by water removal. Upon water addition, a loss of $\lambda_{max,abs}$ at 1013 nm with concomitant appearance of a peak from 750-850 nm is observed (FIG. 15 depicting normalized absorption of Flav7 (3) in acetonitrile (blue) and acetonitrile containing 10-50% water (red, green, purple)), but absorbance at 1013 nm is restored upon water removal (FIG. 16 depicting normalized absorbance of Flav7 (3) in 100% acetonitrile (black). The sample was then diluted by the addition of water to reach 50% water in acetonitrile (blue). After 1.5 hours, the solvent mixture was evaporated and the sample, re-dissolved in 100% acetonitrile (green), exhibited recovery of the $\lambda_{max,abs}$ at 1013 nm). Additionally, monitoring a solution of 0.1 mg/mL 3 in acetonitrile with 10% water over time by LCMS showed no appreciable degradation. Collectively, these data suggest that Flav7 undergoes aggregation, not covalent modification, in water. Finally, the photoluminescence of Flav7 was examined compared to the prominent SWIR polymethine dyes, IR-26 and IR-1061. IR-26 has been widely-employed as a standard for this region, while IR-1061 has recently been the active component of nanomaterials for NIR-II in vivo imaging. See, for example, Chen, J.; Kong, Y; Feng, S.; Chen, C.; Wo, Y; Wang, W.; Dong, Y; Wu, Z.; Li, Y; Chen, S. *ACS Sustain. Chem. Eng.* 2016, 4, 2932-2938, Murphy, J. E.; Beard, M. C.; Norman, A. G.; Ahrenkiel, S. P.; Johnson, J. C.; Yu, P.; Mićić, O. I.; Ellingson, R. J.; Nozik, A. J. *J. Am. Chem. Soc.* 2006, 128, 3241-3247, Dang, X.; Gu, L.; Qi, J.; Correa, S.; Zhang, G.; Belcher, A. M.; Hammond, P. T. *Proc. Natl. Acad. Sci.* 2016, 113, 1-6; and Tao, Z.; Hong, G.; Shinji, C.; Chen, C.; Diao, S.; Antaris, A. L.; Zhang, B.; Zou, Y; Dai, H. *Angew. Chem. Int. Ed.* 2013, 52, 13002-13006. Despite numerous studies which rely on these dyes, the reported $\Phi_F$ for IR-26 have been inconsistent, and the $\Phi_F$ of IR-1061 has yet to be thoroughly characterized. See, Hatami, S.; Würth, C.; Kaiser, M.; Leubner, S.; Gabriel, S.; Bahrig, L.; Lesnyak, V.; Pauli, J.; Gaponik, N.; Eychmüller, A.; Resch-Genger, U. *Nanoscale* 2015, 7, 133-143, Semonin, O. E.; Johnson, J. C.; Luther, J. M.; Midgett, A. G.; Nozik, A. J.; Beard, M. C. *J. Phys. Chem. Lett.* 2010, 1, 2445-2450, Penzkofer, A.; Lammel, O.; Tsuboi, T. *Opt. Commun.* 2002, 214, 305-313. (c) Kranitzky, W.; Kopainsky, B.; Kaiser, W.; Drexhage, K. H.; Reynolds, G. A. *Opt. Commun.* 1981, 36, 149-152, Tao, Z.; Hong, G.; Shinji, C.; Chen, C.; Diao, S.; Antaris, A. L.; Zhang, B.; Zou, Y; Dai, H. *Angew. Chem. Int. Ed.* 2013, 52, 13002-13006, and Casalboni, M.; De Matteis, F.; Prosposito, P.; Quatela, A.; Sarcinelli, F. *Chem. Phys. Lett.* 2003, 373, 372-378, each of which is incorporated by reference in its entirety. Consequently, to establish that Flav7 is more emissive than existing SWIR polymethine dyes, each dye's emission was directly compared using a SWIR camera. Solutions of 3, IR-26, and IR-1061 were prepared in dichloromethane with identical absorbance at 808 nm (FIG. 17 depicting absorbance spectra of the solutions employed in FIG. 3A. Note that their absorbance was matched at 808 nm), excited with a diffuse 808 nm laser, and imaged their emission over 1000-1500 nm (FIG. 3A). The average intensity was quantified for each cuvette in the same position within the field of view (FIG. 3B) and clearly indicates that Flav7 is the brightest of the three dyes. These data correlate well with absolute $\Phi_F$ determined using an integrating sphere (FIG. 3C). The $\Phi_F$ measurements of IR-26 are consistent with recent reports and contrast the prior accepted value. See, Hu, H.; Przhonska, O. V; Terenziani, F.; Painelli, A.; Fishman, D.; Ensley, T. R.; Reichert, M.; Webster, S.; Bricks, J. L.; Kachkovski, A. D.; Hagan, D. J.; Van Stryland, E. W. *Phys. Chem. Chem. Phys.* 2013, 15, 7666-7678 and Casalboni, M.; De Matteis, F.; Prosposito, P.; Quatela, A.; Sarcinelli, F. *Chem. Phys. Lett.* 2003, 373, 372-378, each of which is incorporated by reference in its entirety. The originally published $\Phi_F$ of IR-26 and IR-1061 was concluded to be overestimated, and the $\Phi_F$ of IR-26, IR-1061, and Flav7 are 0.046±0.03%, 0.32±0.04%, and 0.53±0.3%, respectively. These data suggest that Flav7 or commercially available IR-1061 are better comparative sources for SWIR measurements. Furthermore, direct comparative imaging experiments were deemed as the most reliable method to evaluate the brightness of fluorophores in the SWIR.

Here, a new class of polymethine dyes with dimethylamino flavylium heterocycles were designed. These dyes are notably red-shifted compared to prevalent cyanine dyes, and expand the opportunities for imaging and detection in the NIR and SWIR. Typically, the stability and emission of fluorophores decrease as their absorption moves to lower energies, highlighting the challenge of achieving stable, bright fluorophores, particularly in the SWIR. The three NIR polymethine dyes reported display excellent photostabilities with varying quantum yields. The hallmark fluorophore of this series is the heptamethine (Flav7) which is 13-times brighter than IR-26, the current SWIR benchmark. Flav7 was determined to be the superior SWIR fluorophore using a comparative imaging experiment and absolute $\Phi_F$. Concurrent to this work, benzobisthiadiazole-thiophene fluorophores with shielding units have been developed for NIR-II imaging. See, for example, Yang, Q.; Ma, Z.; Wang, H.; Zhou, B.; Zhu, S.; Zhong, Y; Wang, J.; Wan, H.; Antaris, A.; Ma, R.; Zhang, X.; Yang, J.; Zhang, X.; Sun, H.; Liu, W.; Liang, Y; Dai, H. *Adv. Mater.* 2017, DOI: 10.1002/adma.201605497, and Zhu, S.; Yang, Q.; Antaris, A. L.; Yue, J.; Ma, Z.; Wang, H.; Huang, W.; Wan, H.; Wang, J.; Diao, S.; Zhang, B.; Li, X.; Zhong, Y; Yu, K.; Hong, G.; Luo, J.; Liang, Y; Dai, H. *Proc. Natl. Acad. Sci. U.S.A.* 2017, DOI: 10.1073/pnas.1617990114, each of which is incorporated by reference in its entirety. While this scaffold affords impressive $\Phi_F$, the high e of polymethine dyes results in larger quantum efficiencies for the dimethylamino flavylium NIR/SWIR emitters. Polymethine fluorophores have other distinctive properties including narrow absorption and emission bands and the ability to be chemically fine-tuned, which poise them to be a promising fluorophore scaffold for new technologies in these underdeveloped regions of the EM spectrum.

In one aspect, a compound can be a flavylium polymethine dye wherein the polymethine includes a methine chain from 1 to 7 carbons and having a fluorescence emission from 680 to 1045 nm.

In certain embodiments, the flavylium polymethine dye can include a dialkylamino flavylium moiety.

In certain embodiments, the dialkylamino flavylium moiety can be a dimethylamino flavylium moiety or a diethylamino flavylium moiety.

In certain embodiments, the polymethine can be a monomethine dye, a tri-methine dye, a penta-methine dye or a hepta-methine dye.

In another aspect, the compound can be of formula (I):

wherein n is 1, 2, or 3,

X⁻ is Cl⁻, ClO₄⁻, BF₄⁻, Br⁻, I⁻, tosylate, triflate, trifluoroacetate, acetate, bromide, or tetraalkylborate, at least one Het is a flavylium and the other Het is heteroaryl, and and the methine is substituted or unsubstituted.

In certain embodiments, the at least one Het can be a flavylium and the other Het can be flavyl, flavylium, indolyl, or cyanyl.

In certain embodiments, the compound can be a flavylium polymethine.

In certain embodiments, the compound can be

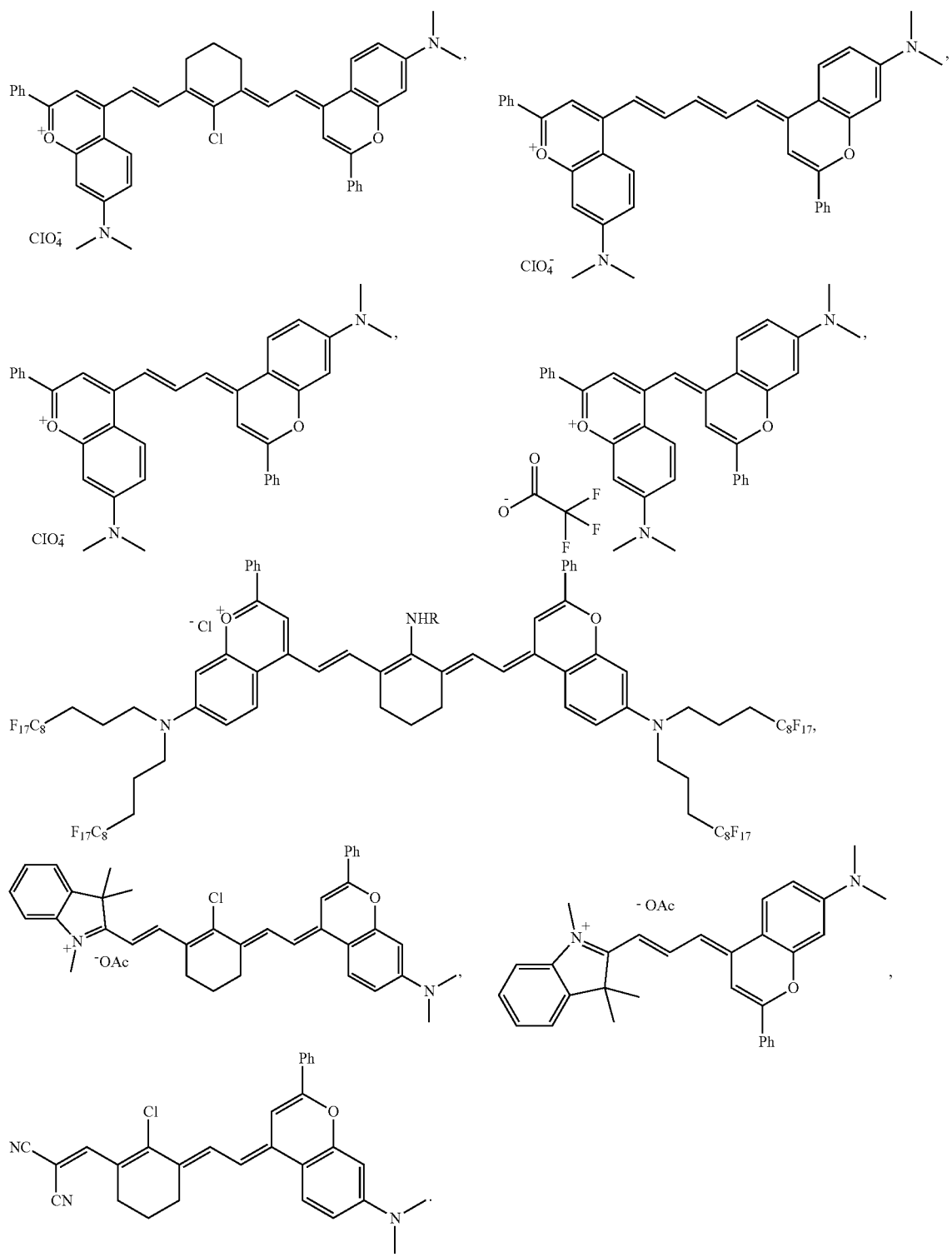

The term "heteroaryl," as used herein, alone or in combination, refers to a 3 to 15 membered unsaturated hetero-monocyclic ring, or a fused monocyclic, or bicyclic ring system in which at least one of the fused rings is aromatic, which contains at least one atom chosen from O, S, and N. Additionally, a heteroaryl may contain one or two C(O), C(S), or $CS(O)_3$ groups as ring members. In certain embodiments, said heteroaryl will comprise from 5 to 10 atoms. In certain embodiments, said heteroaryl will comprise from 5 to 7 atoms. In certain embodiments, said heteroaryl will comprise from 1 to 4 heteroatoms as ring members. In further embodiments, said heteroaryl will comprise from 1 to 2 heteroatoms as ring members. The term also embraces fused polycyclic groups wherein heterocyclic rings are fused with aryl rings, wherein heteroaryl rings are fused with other heteroaryl rings, wherein heteroaryl rings are fused with heterocycloalkyl rings, or wherein heteroaryl rings are fused with cycloalkyl rings. Examples of heteroaryl groups include flavylium, flavyl, pyrrolyl, pyrrolinyl, pyrazolyl, pyridyl, pyrimidinyl, pyrazinyl, pyridazinyl, imidazolyl, triazinyl, triazolyl, tetrazolyl, pyranyl, furyl, thienyl, oxazolyl, isoxazolyl, oxadiazolyl, thiazolyl, thiadiazolyl, isothiazolyl, indolyl, isoindolyl, indolizinyl, benzimidazolyl, quinolyl, isoquinolyl, quinoxalinyl, quinazolinyl, indazolyl, benzotriazolyl, benzodioxolyl, benzopyranyl, benzoxazolyl, benzoxadiazolyl, benzothiazolyl, benzothiadiazolyl, benzofuryl, benzothienyl, chromonyl, coumarinyl, benzopyranyl, tetrahydroquinolinyl, tetrazolopyridazinyl, tetrahydroisoquinolinyl, thienopyridinyl, furopyridinyl, pyrrolopyridinyl and the like. Preferred heteroaryl compounds include nitrogen or oxygen heteroatoms. The preferred compounds do not include sulfur heteroatoms.

Preferably, the dyes contain an amino group, particularly, an alkyl or dialkyl amino group. The term "amino," as used herein, alone or in combination, refers to —NRR', wherein R and R' are independently chosen from hydrogen, alkyl, acyl, heteroalkyl, any of which may themselves be optionally substituted.

General Experimental Procedures

Chemical reagents were purchased from Sigma-Aldrich or Acros Organics and used without purification unless noted otherwise. Anhydrous DMSO was obtained from a Sure-Seal™ bottle (Aldrich). Anhydrous and deoxygenated solvents DCM, MeCN, MeOH, THF were dispensed from a Grubb's-type Phoenix Solvent Drying System. Anhydrous but oxygenated DCM and EtOH were prepared by drying over 4 Å molecular sieves for at least 3 days. Thin layer chromatography was performed using Silica Gel 60 $F_{254}$ (EMD Millipore) plates. Flash chromatography was performed with technical grade silica gel with 60 Å pores and 40-63 µm mesh particle size (Sorbtech Technologies). High performance liquid chromatography was performed using a semi-prep reverse phase ($C_{18}$) column with a Waters HPLC system equipped with a UV-Vis detector set at 254 nm. Solvent was removed under reduced pressure with a Büchi Rotovapor with a Welch self-cleaning dry vacuum pump and further dried with a Welch DuoSeal pump. Nuclear magnetic resonance ($^1$H NMR, $^{13}$C NMR, and $^{19}$F NMR) spectra were taken on Bruker Avance 500 ($^1$H NMR and $^{13}$C NMR) or AV-300 ($^{19}$F NMR) instruments and processed with MestReNova software. All $^1$H NMR and $^{13}$C NMR peaks are reported in reference to DMSO-$d_6$ at 2.50 ppm and 39.52 ppm, respectively. $^{19}$F NMR is in respect to α,α,α-trifluorotoluene at −63.90 ppm as an external standard. (see, Bexrud, J. A.; Eisenberger, P.; Leitch, D. C.; Payne, P. R. *J. Am. Chem. Soc.* 2009, 131, 2116, which is incorporated by reference in its entirety) HRMS data were obtained from the MIT Department of Chemistry Instrument Facility. Absorbance spectra were collected on a JASCO V-770 UV-Visible/NIR spectrophotometer with a 4000 nm/min scan rate after blanking with the appropriate solvent or on a Cary 5000 UV-VIS-NIR spectrometer. Photoluminescence spectra were obtained on a Horiba Instruments PTI QuantaMaster Series fluorometer or a Fluoromax-3 spectrofluorometer or home-built InGaAs array detector (Princeton Instruments). Quartz cuvettes (1 cm) were used for absorbance and photoluminescence measurements. Extinction coefficients were calculated with serial dilutions in dichloromethane in volumetric glassware. Error was taken as the standard deviation of the triplicate measurement. Absolute quantum yields were determined in DCM with an integrating sphere as described in FIG. 3C experimental procedure. Analysis by X-ray photoelectron spectroscopy (XPS) was performed on a Kratos Axis Ultra DLD spectrometer with a monochromatic (Al—$K_α$) radiation source. For assessment of the statistical significance of differences, a one-tailed Student's t-test assuming unequal sample variance was employed. Results were considered significantly different if p<0.05.

Table Experimental Procedures

TABLE 1

The $λ_{max, abs}$ values were obtained in DCM on a JASCO V-770 UV-Visible/NIR spectrophotometer with a 2000 nm/min scan rate. Extinction coefficient values were obtained from serial dilutions using 10 mL and 5 mL volumetric flasks and 1 mL Hamilton glass syringes.

All masses were determined on a Sartorius MSE6.6S-000-DM Cubis Micro Balance. Error reported in the SI reflects the standard deviation of the triplicate measurement. $λ_{max, em}$ values were obtained as described in the FIG. 2 experimental procedure, below. The quantum yield values were collected as described in the FIG. 3C experimental procedure, below.

TABLE 2

The raw photobleaching rate, k, was obtained by treating the reaction as pseudo first order[1] and taking the - slope of the linear region ($R^2$ > 0.95) (see, (a) Toutchkine, A.; Nguyen, D. V.; Hahn, K. M. *Org. Lett.* 2007, 9, 2775-2777. (b) Song, B.; Zhang, Q.; Ma, W. H.; Peng, X. J.; Fu, X. M.; Wang, B. S. *Dye. Pigment.* 2009, 82, 396-400. (c) Chen, X.; Peng, X.; Cui, A.; Wang, B.; Wang, L.; Zhang, R. *J. Photochem. Photobiol. A Chem.* 2006, 181, 79-85). To incorporate the respective extinction coefficients at 532 nm, the relative rate, $k_{rel}$, was calculated by dividing k by the relative extinction coefficient compared to Flav3. These data were compared to Flav3 as it has the highest extinction coefficient at that wavelength. All error reported represents the propagated error from standard deviation of three replicates.

TABLE 4

In a similar fashion to the normalization of photobleaching rate for the number of incident 532 nm photons absorbed (Table 2), photobleaching rates for Flav3 and HITCI at 730 nm excitation must be corrected before direct comparison. The raw values for the rates are displayed in Table 4. However, the 730 nm LED source (Thor Labs) is non-monochromatic, with a Gaussian profile and FWHM bandwidth of 55 nm. The absorption extinction coefficients for the two dye molecules change appreciably over this range. A slightly altered procedure must be used because of the non-monochromatic source and absorption. The convolution of the excitation source and the wavelength dependent cross-sections are calculated for each dye, and these areas are used as the scalar factor correction to normalize the rates by the actual number of photons absorbed. The magnitude of this correction only altered the relative photobleaching rates by about 14% in favor of a faster decay for Flav3. With this correction, Flav3 decays at a rate 4x slower than HITCI. The error reported represents propagated error from standard deviation of three replicates.

Figure Experimental Procedures

FIG. 2

Absorbance spectra were obtained in DCM on a JASCO V-770 UV-Visible/NIR spectrophotometer with a 4000 nm/min scan rate. Plotted are the baseline corrected and normalized data. Emission spectra were taken in DCM on either a Horiba Instruments PTI QuantaMaster Series fluorometer (6), a Fluoromax-3 spectrofluorometer (1, 3-5), or home-built InGaAs array detector (Princeton Instruments). For 6 the following parameters were used: ex. 610 nm, emission collected from 620-900 nm, slits 5 nm, step size 1 nm, integration time 1 s. Plotted is the DCM corrected, baseline corrected, normalized data. For 1, and 3-5, the following parameters were used: slits 5 nm, step size 1 nm, integration time, 0.25 s. Excitation values and emission collection were as follows: 1 (ex. 460, collection 470-800 nm), 5 (ex. 675 nm, collection 685-950 nm), 4 (ex. 840 nm, emission 850-1100 nm), 3 (ex. 730 nm, emission 950-1400). Plotted are the baseline corrected, normalized data.

FIG. 3A/B

Flav 7 3, IR-26, and IR-1061 were diluted in DCM until matching absorbance was achieved at 808 nm (FIG. 15). Spatially dispersed 808 nm illumination was used to image 1 ml samples in 2.5 mL cuvettes of the SWIR dyes alongside a DCM blank. Each dye was compared at the same position to ensure consistent camera illumination. SWIR images were collected on an InGaAs camera (Princeton Instruments, NIRvana 640) with a 1000 nm long-pass filter. The camera was cooled to −80° C., the analog to digital (AD) conversion rate set to 2 MHz, the gain set to high, and different exposure times used to achieve sufficient signal and/or frame rates. All images were background- and blemish-corrected within the LightField imaging software. All analysis was performed using ImageJ and Matlab (Mathworks). Bar graph intensities were taken as the average camera intensity for 10 frames, background corrected to the DCM blank, with the error corresponding to standard deviation.

FIG. 3C

IR-26 and IR-1061 (Exciton) were diluted in DCM to 0.5 maximum absorbance for quantum yield measurements. Absorption spectra were measured using Cary 5000 UV-VIS-NIR spectrometer, and emission spectra were recorded using a Fluoromax-3 spectrofluorometer, or a home-built InGaAs array detector (Princeton Instruments). Quantum yield was performed using a Labsphere integrating sphere and a 5 mW 405/780 nm laser, with optical chopping at 210 Hz. The output was collected using either a calibrated silicon or InGAs detector connected to a Lock-In amplifier (Stanford Research Instruments). Colored Glass Filters were used to spectrally separate the fluorescence, and the final quantum yield was corrected for reflectance and leakage of the filter.

Calculating Quantum Yield

The photoluminescent quantum yield of a dye or material is defined as follows $$QY = P_E/P_A \tag{1}$$

Where $P_{E,A}$ are the number of photons absorbed and emitted respectively. To determine absolute quantum yield, either a known standard (relative method), or measure the number of photons absorbed and emitted independently (absolute method) was used. Due to the lack of a bright consistent standard in the SWIR range (1000-2000 nm), the absolute method is preferable. Here, the procedure for measuring quantum yields in the shortwave infrared was described, and compared several SWIR emissive dyes.

1. Absolute Measures of Quantum Yield

Figure 19:
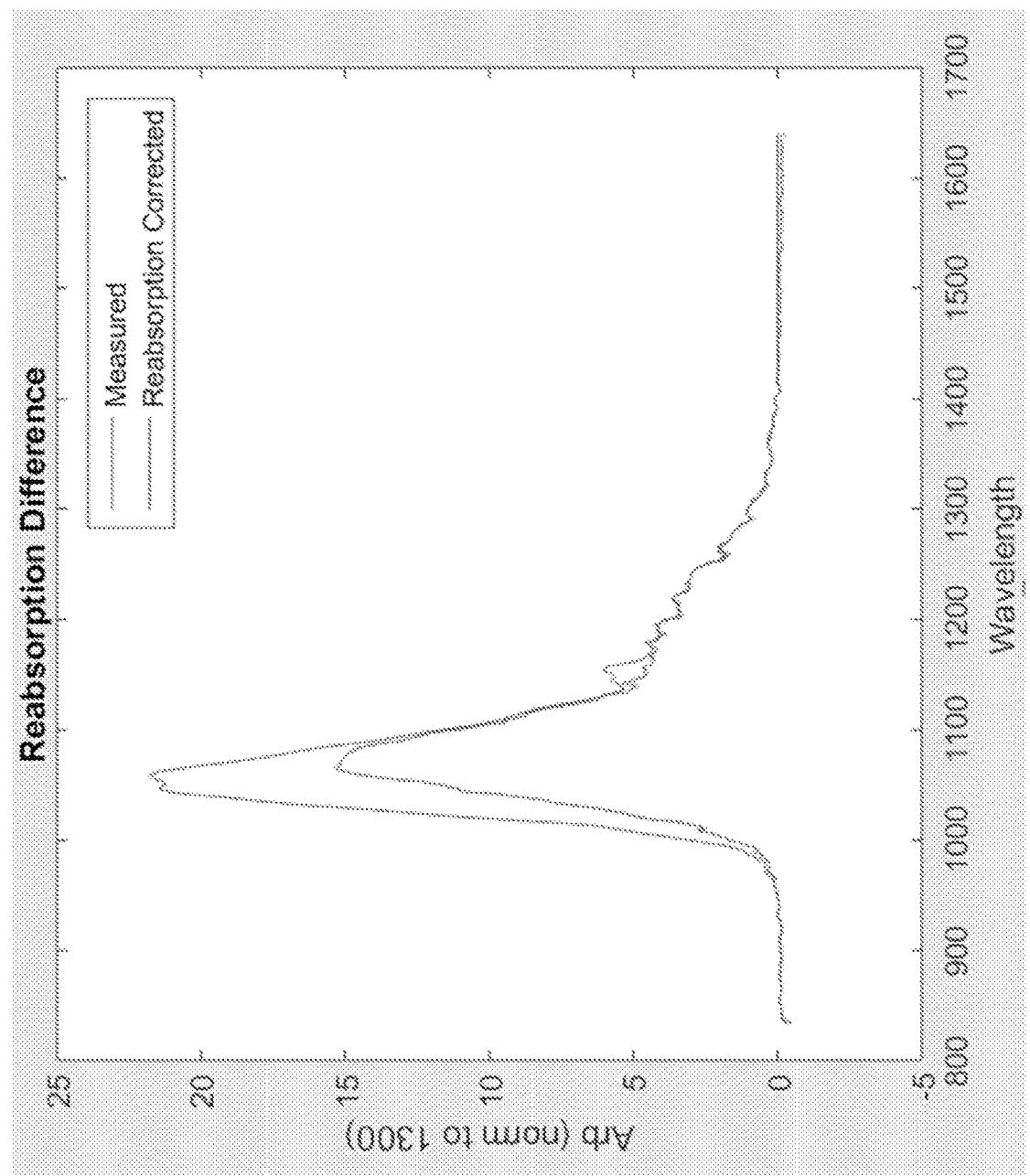
Figure 20:
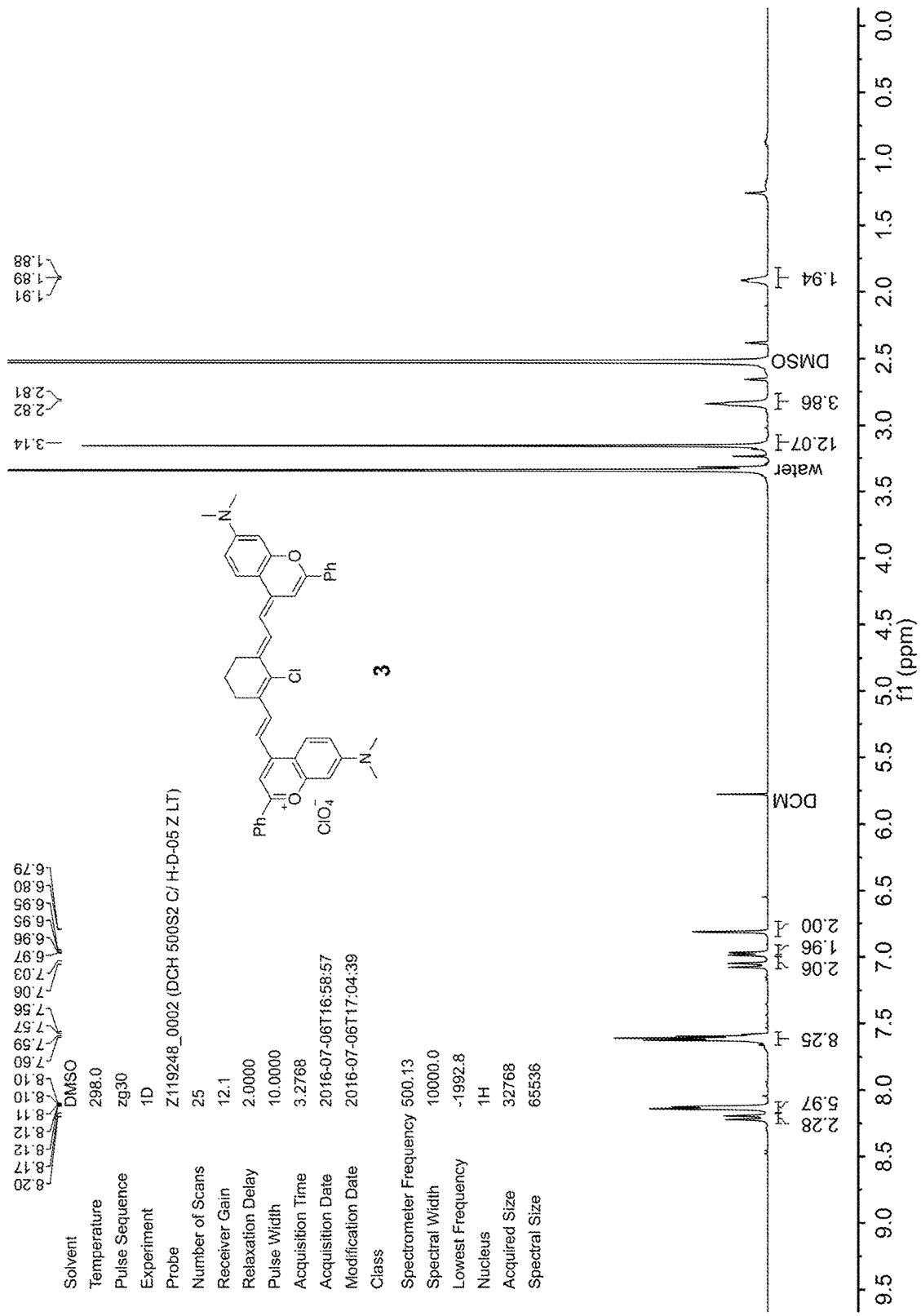
Figure 21:
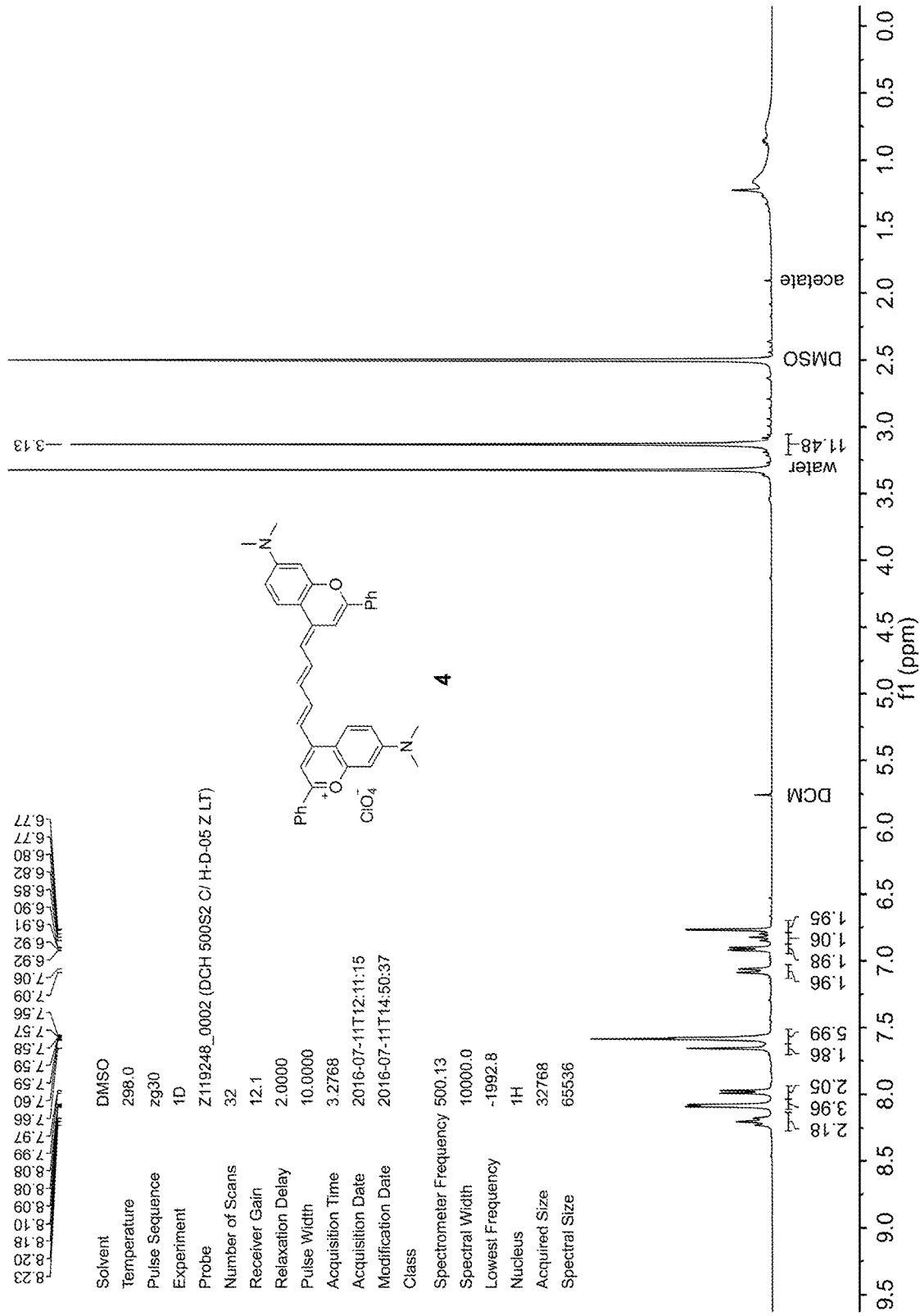
Figure 22:
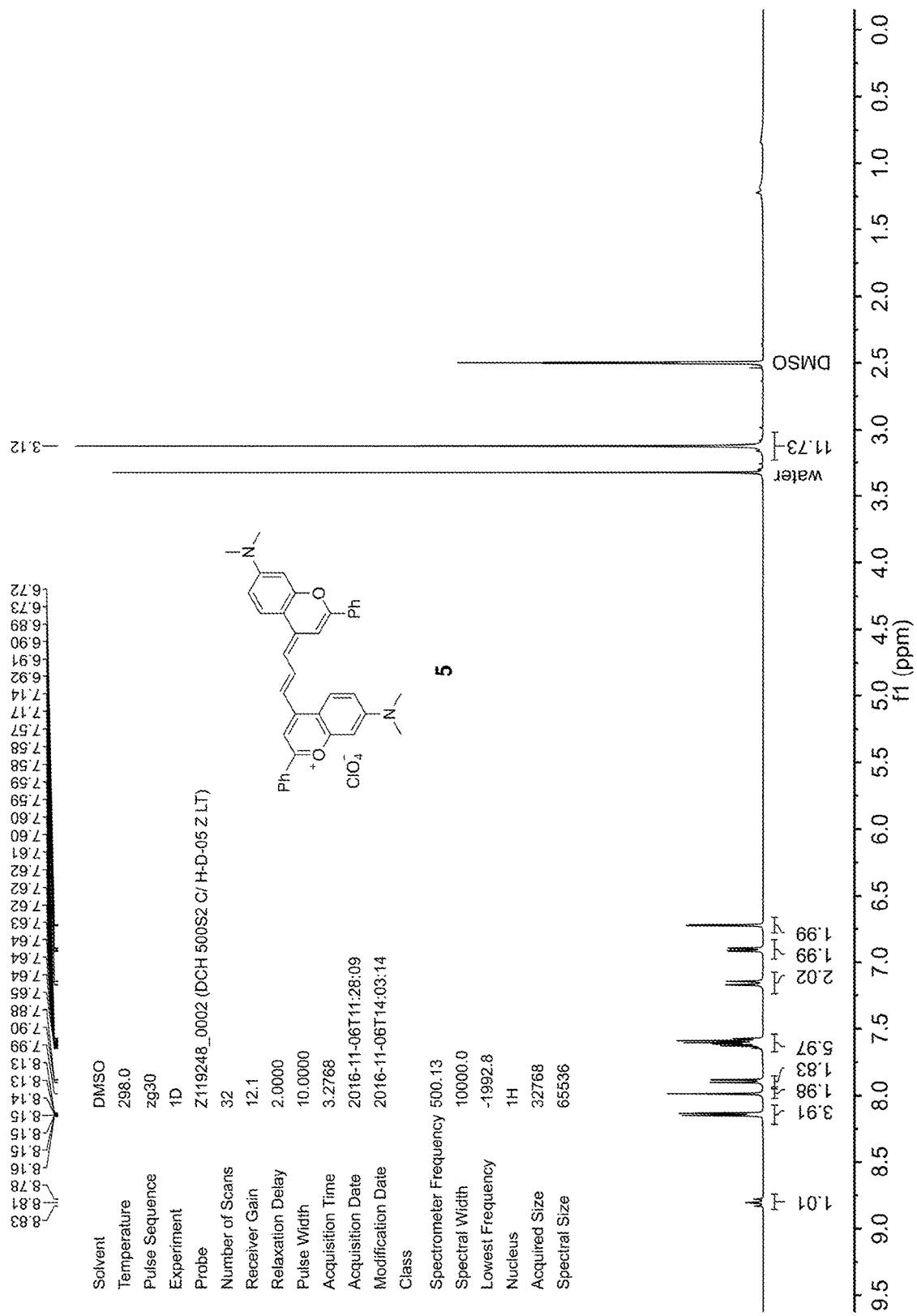
Figure 23:
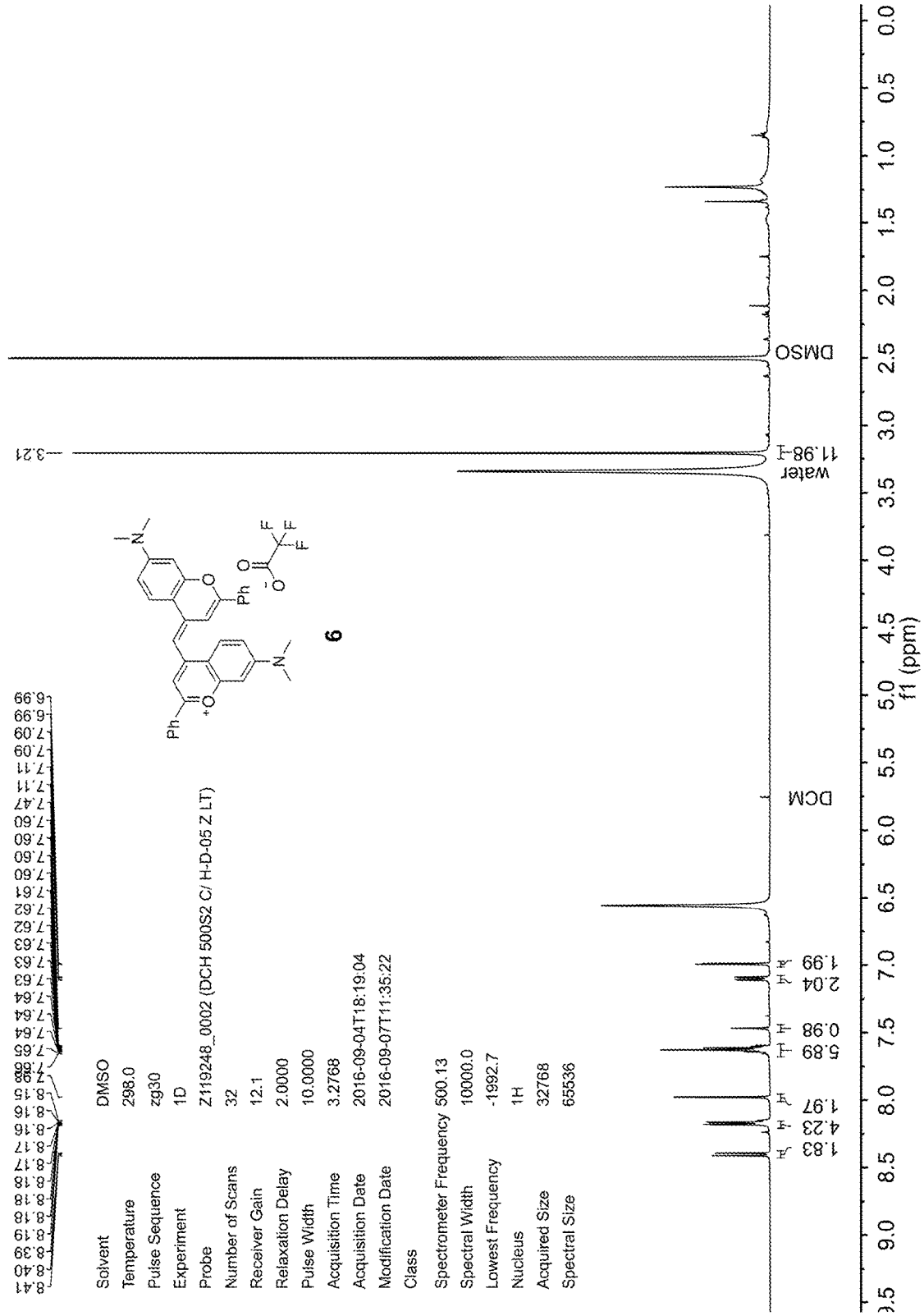
Figure 24:
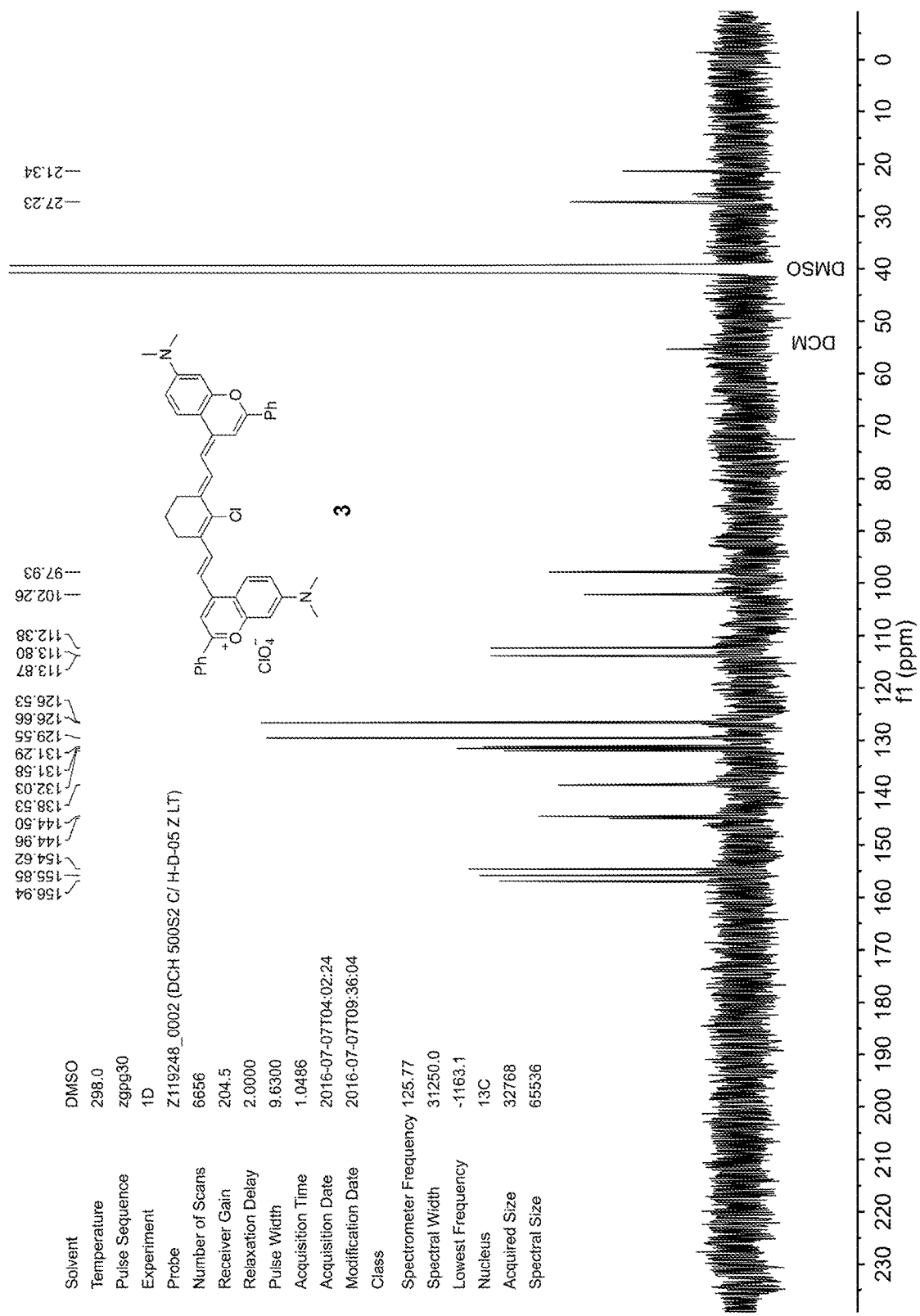
Figure 25:
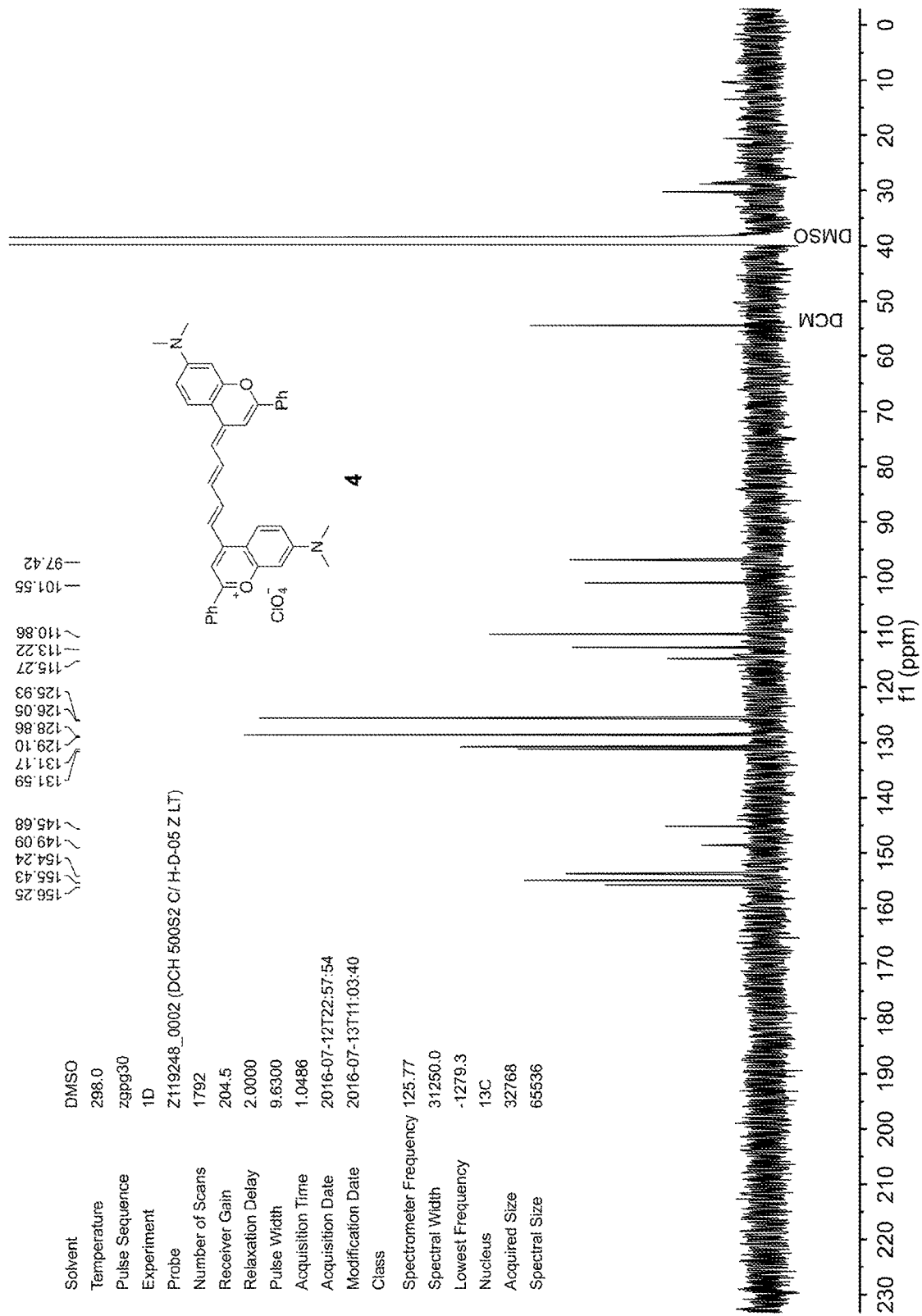
Figure 26:
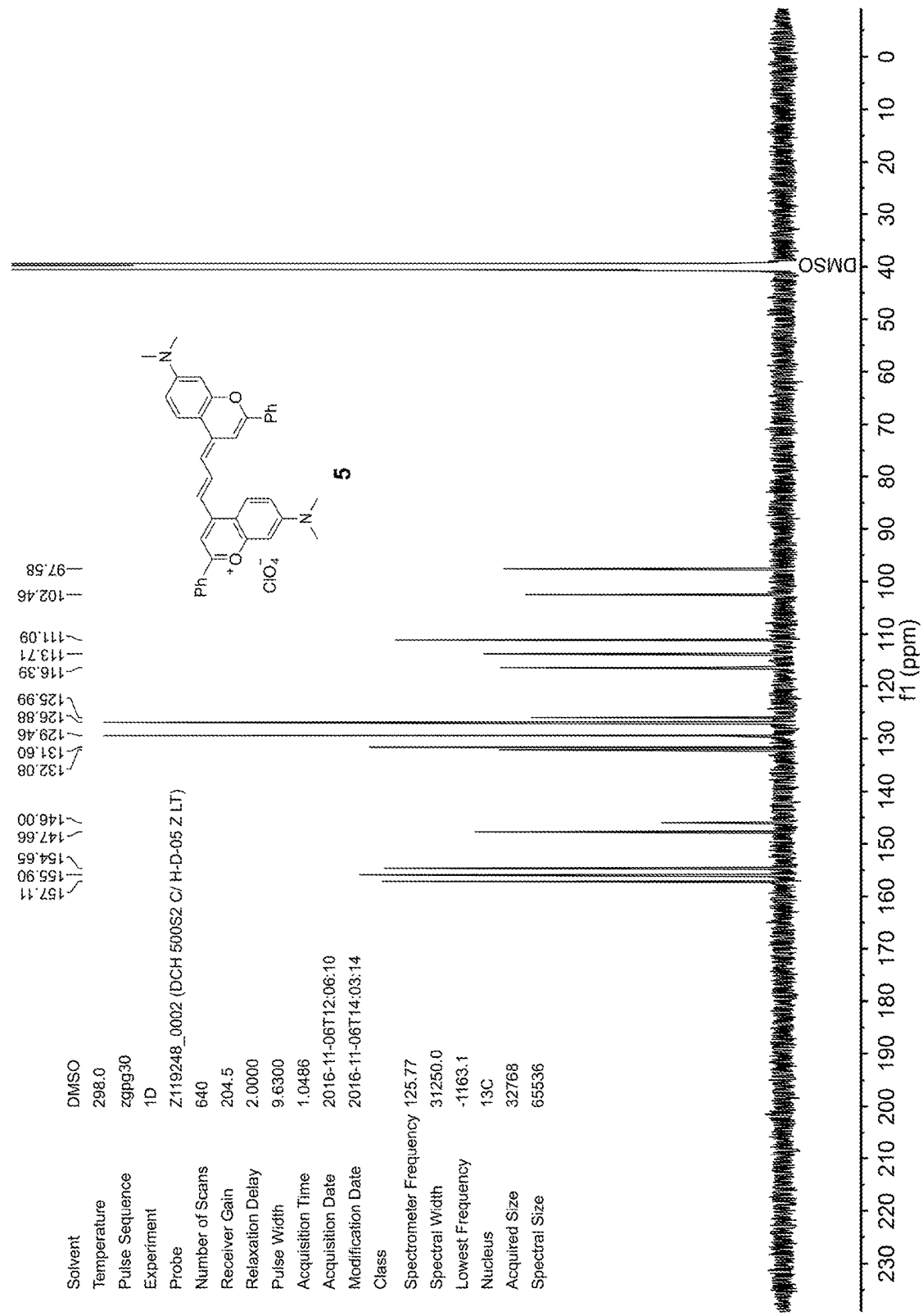
Figure 27:
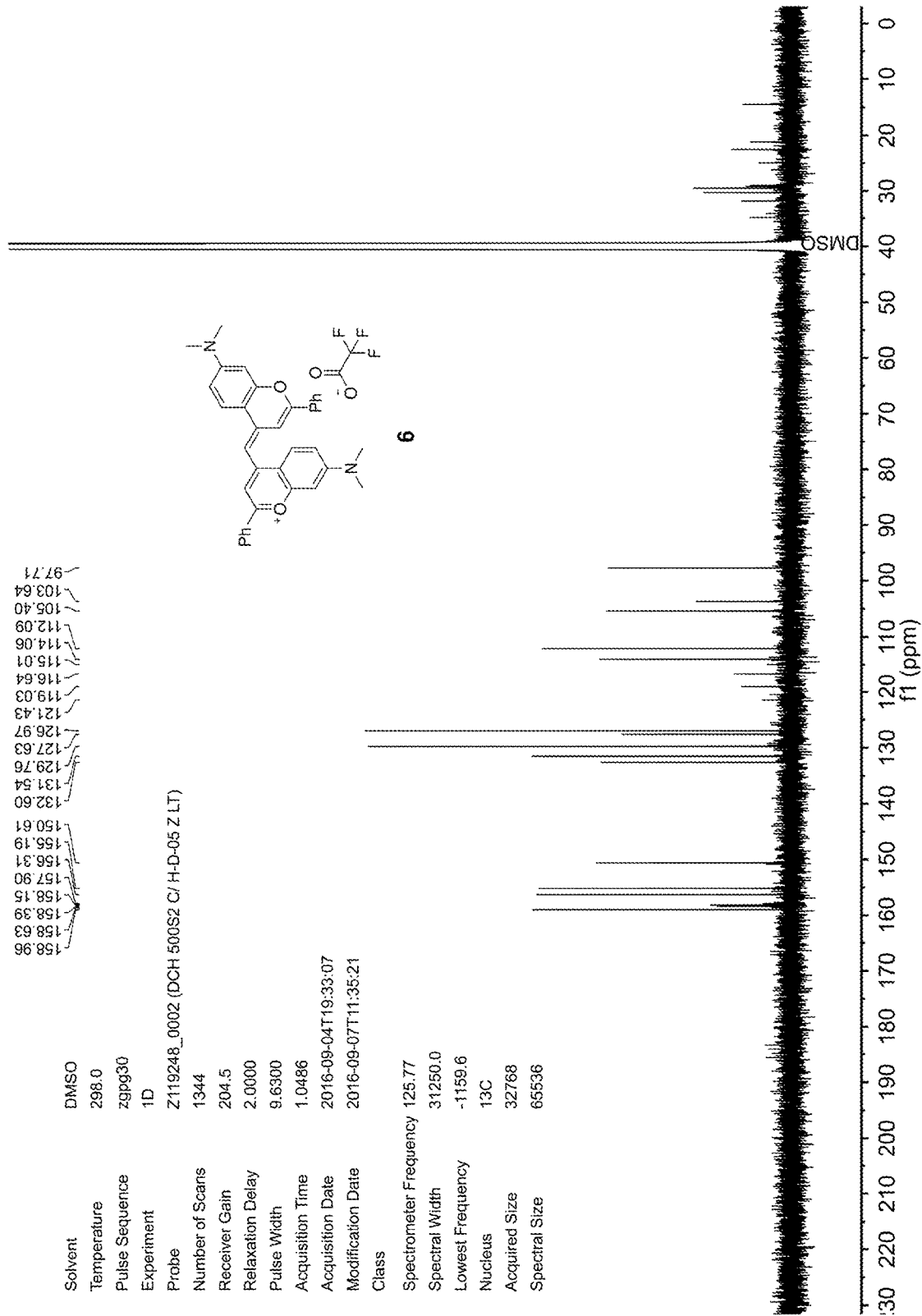
Figure 28:
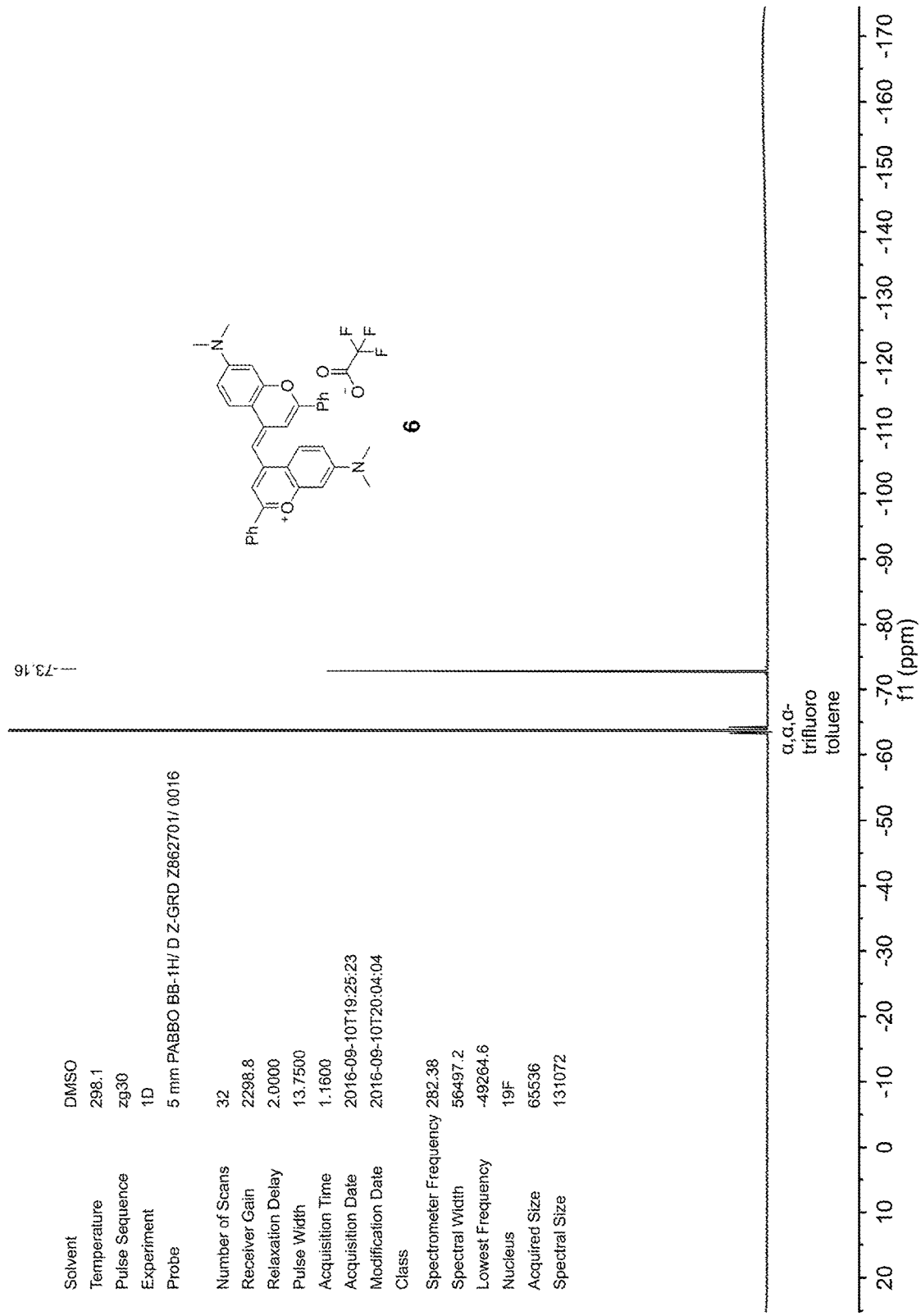
Figure 29:
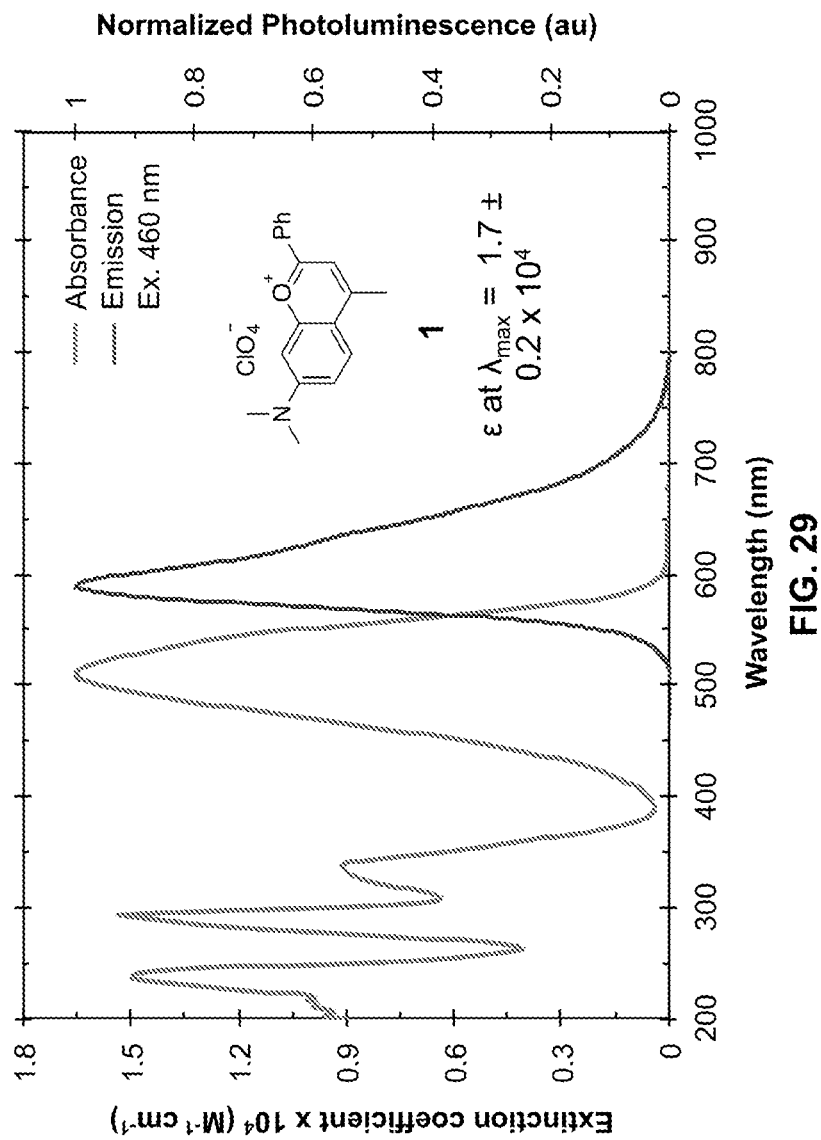
Figure 30:
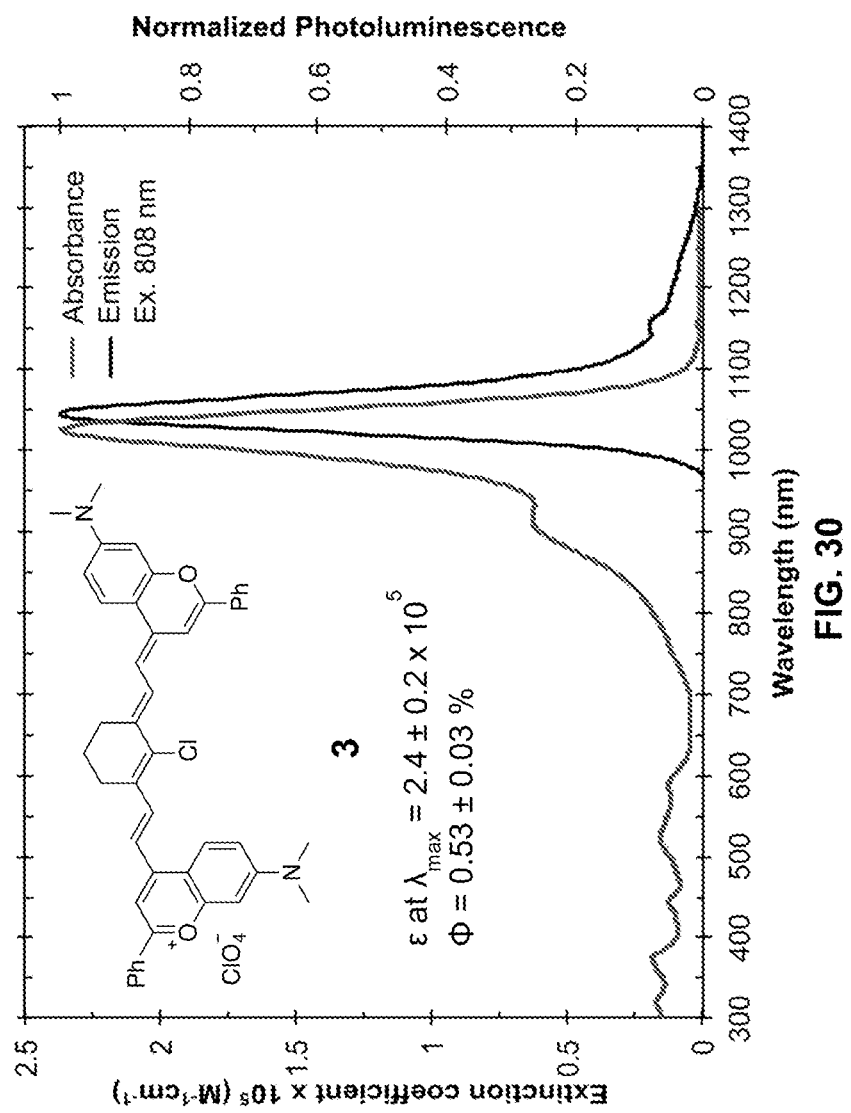
Figure 31:
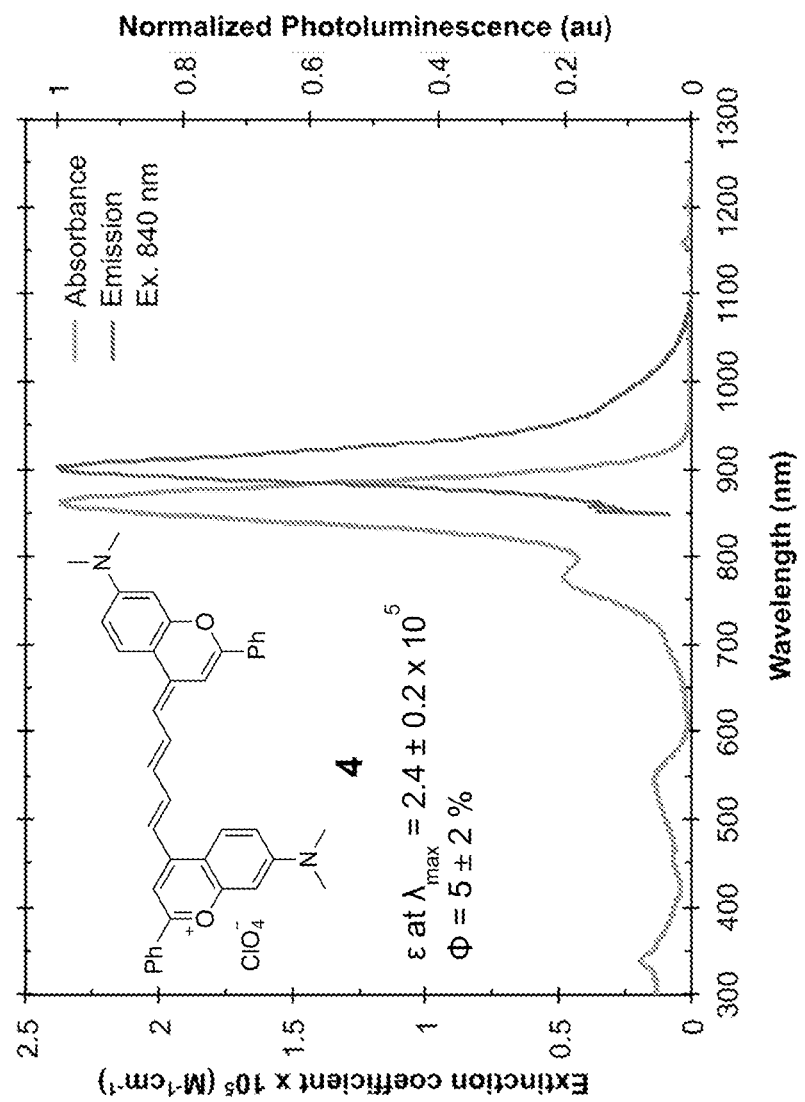
Figure 32:
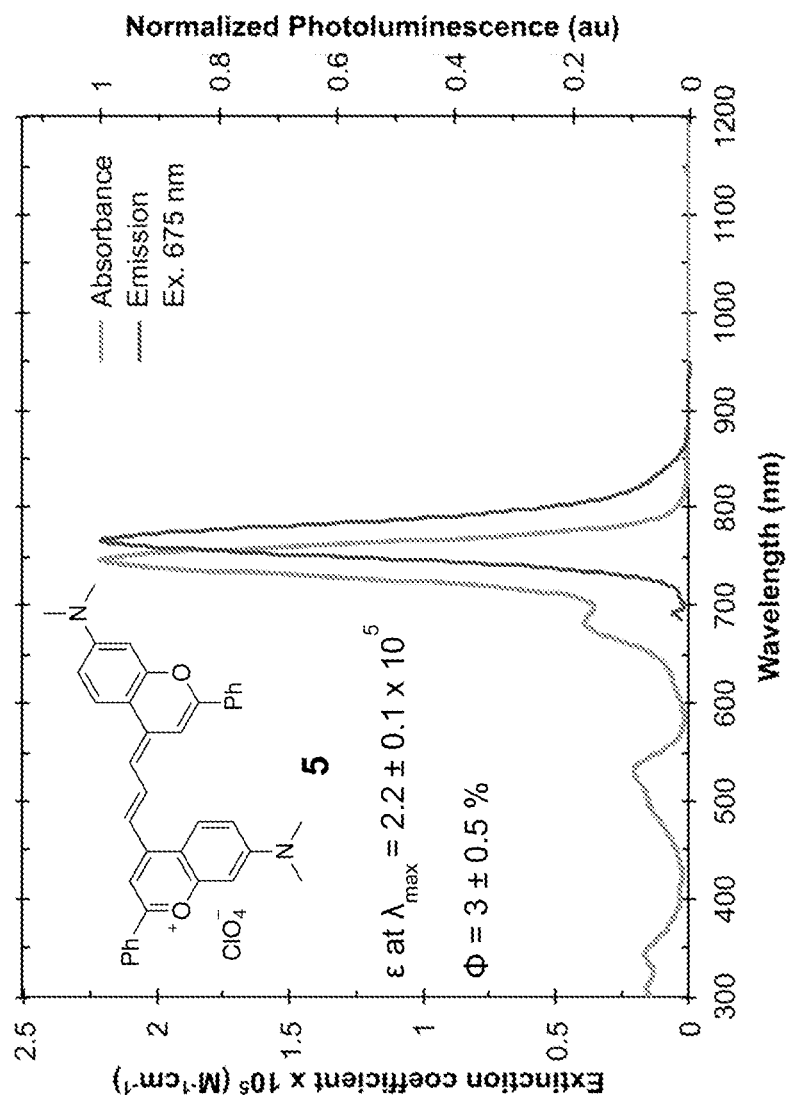
Figure 33:
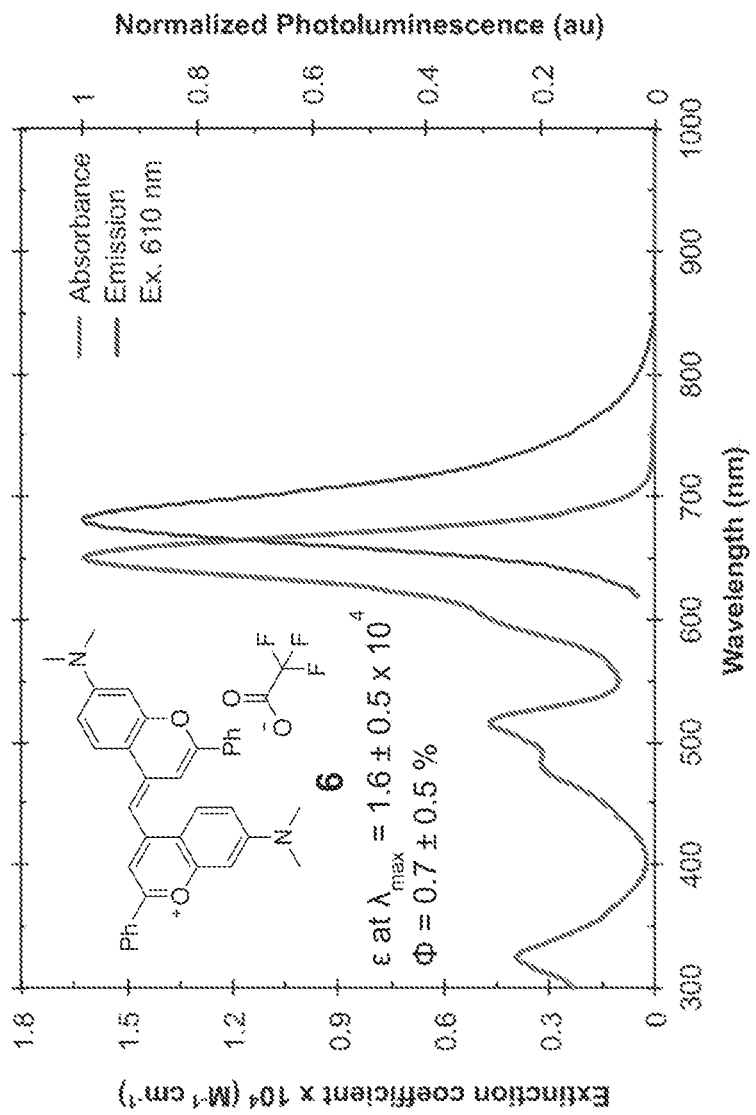

To perform an absolute quantum yield measurement, an integrating sphere was used, where a standard cuvette is illuminated on all sides by scattering a laser against white Teflon. The direct scatter is obfuscated by a baffle, and a side port is used with a large-area detector (E.G. 818VIS/IR from Newport). The laser was modulated using an optical chopper, and the photogenerated current is measured on a lock-in amplifier. In this way, pA signals can be measured against large constant backgrounds. The current at the chopping frequency was recorded using both a solvent filled blank, and the fluorophore. A filter is placed in front of the detector that only allows the fluorescence to pass through, and the procedure is repeated. The simplest calculation of quantum yield is therefore, $$\frac{P_E}{P_A} = \frac{I_{SF} - I_{NSF}}{I_{NSNF} - I_{SNF}}, \tag{2}$$

Where (N)S(N)F denotes (no) sample and (no) filter respectively. This approach neglects the impact of detector quantum efficiency at the wavelength of excitation, and the emitted wavelength. In FIG. 19 (depicting reabsorption corrected spectroscopy) the relative external quantum efficiency (EQE=$\eta$=$I_{rel}/P_A$) of the detector was plotted (Newport, 818IR Germanium). The average response over the emitted wavelength range was calculated as follows, $$\eta_{em} = \frac{\int_{\lambda_{min}}^{\lambda_{max}} d\lambda \eta(\lambda) S(\lambda)}{\int_{\lambda_{min}}^{\lambda_{max}} d\lambda S(\lambda)}, \tag{3}$$

where $S(\lambda)$ is the measured PL spectrum. For excitation, the EQE at $\lambda_{exc}$ was evaluated. These correction terms go into equation 2.

$$\frac{P_E}{P_A} = \frac{(I_{SF} - I_{NSF})/\eta_{em}}{(I_{NSNF} - I_{SNF})/\eta_{exc}} \quad (4)$$

For excitation at 780, and emission in the 1100-1200 range, η can range over a factor of 2, making this correction crucial to accurate QY determination. To further refine the estimate, the light emitted by the sample (the fluorescence) and detected in $I_{SNF}$ was considered. Equation 5 by subtracting the emitted photons from the denominator was adjusted.

$$\frac{P_E}{P_A} = \frac{(I_{SF} - I_{NSF})/\eta_{em}}{(I_{NSNF} - I_{SNF})/\eta_{exc} - (I_{SF} - I_{NSF})/\eta_{em}} \quad (5)$$

Figure 18:
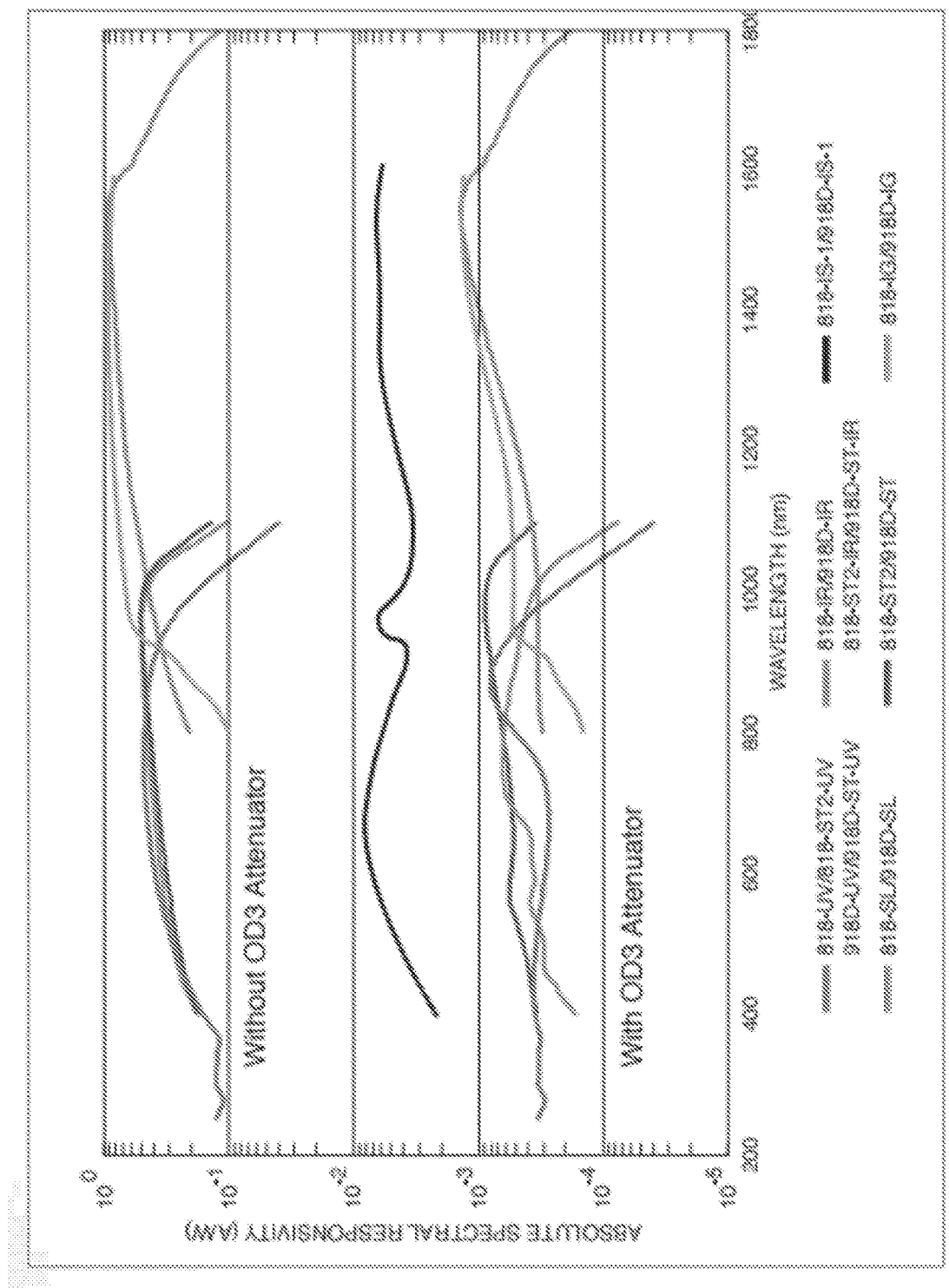

This tends to lower the observed quantum yield. The last step is considering reflection and loss due to the filter. Filter transmission can be measured and divided to give the final estimate=$\Phi_{F(eq.5)}/T_f$. See, for example, FIG. 18, depicting Detector response taken from Newport instruments. The 818IR calibrated photodiode (germanium) was used.

2. Reabsorption Correction

Including sample/solvent reabsorption is typically done using a dilution series. However, in the case of IR dyes, there are significant solvent absorption in the spectra. Therefore, and alternative approach is necessary.

As a first step, the absorption and emission spectrum collected at the same angle (0 or 180 degrees) was used. This geometry was used to calculate the effect of absorption on the emission. The effect of sample penetration and reabsorption on the "real emission spectrum" $f(\lambda)$ was calculated. A correction factor $R(\lambda)$, such that $R(\lambda)f^*(\lambda)=f(\lambda)$ was derived, the measured experimental emission spectrum.

$$R(\lambda) = \frac{1}{L}\int_0^L dx\, 10^{-x/L(A_{exc}+A(\lambda))} = \frac{1 - 10^{-(A_{exc}+A(\lambda))}}{(A_{exc} + A(\lambda))\ln(10)} \quad (6)$$

The results are shown in FIG. 19. Using this, a correction factor associated with reabsorption in the integrating sphere was derived. For simplicity, normalize the spectrum at 1300 nm was assumed, where no reabsorption occurs, and integrate the ratio of the "real spectra" to the reabsorption corrected measure. The final quantum yield is multiplied by this correction factor.

3. Comments on Overall Approach

Our approach enables the rapid determination and comparison of quantum yield, and allows us to obtain results comparable to those described in the literature for IR26 (0.05% from Beard and Nozick, 0.09% from Rensch Genger in DCE). Unlike prior methods, this approach does not spectrally resolve emission, and can be completed in under 1 minute, enabling rapid quantification and comparison among different samples. The use of single detector also enables lock-in detection, decreasing background. However, the approach does not allow us to fully consider reabsorption, as the geometry of emission and reabsorption within the integrating sphere was not accounted for. While equation 6 partially accounts for reabsorption (and is consistent with the approach provided in Beard and Nozick), it may account for the ~2 difference between the measurement and the measurement of Rensch-Genger. Reabsorption is particularly important in the SWIR, as overtone solvent vibrational modes contribute to absorption (and cannot be eliminated using conventional dilution.

In Table 5, a list of SWIR dyes whose QY have been estimated using these methods was provided.

TABLE 5

$\Phi_F$ values for SWIR fluorophores, analyzed as describe above.

| Dye | Eq. (2) | Eq. (4) | Eq. (5) | $\Phi_F$ | Error (±) |
|---|---|---|---|---|---|
| Flav7 | 0.79 | 0.4 | 0.39 | 0.53 | 0.03 |
| IR1061 | 0.51 | 0.26 | 0.26 | 0.32 | 0.04 |
| IR26 | 0.06 | 0.028 | 0.028 | 0.046 | 0.03 |

All QY are corrected for filter transmission. The values in Eq. 2 are derived from equation 2, Eq. 4 from equation 4, and Eq. 5 from equation 5. The final, reabsorption corrected quantum yield values are $\Phi_F$, as described in the text. Error is propagated from uncertainty in photodiode current, and repeat measurements with different sample concentrations.

Supporting Figure Procedures

FIGS. 5A-5B

Flavylium 1 at 2.5 mM in EtOH, with excess sodium acetate was reacted at 85° C. after (A) no removal of oxygen and (B) freeze-pump-thaw ×3. Aliquots were taken via syringe and further diluted in DCM for analysis by UV-Vis-IR (Cary 4000 UV/Vis spectrophotometer, Agilent Technologies) with a scan rate of 2000 nm/min.

FIG. 8 and FIG. 9

Samples were prepared by dissolving in DCM, drop-casting repeatedly onto a copper sample holder, and drying in vacuo. Survey and high-resolution scans were acquired at 160 and 20 eV pass energy respectively, with step sizes of 1 and 0.1 eV. As the samples were not conductive, the charge neutralizer filament was used. Data analysis and quantification was performed with Casa-XPS software. The atomic relative sensitivity factors used were from the Kratos library within the Casa software.

FIG. 10

Each dye was dissolved in DCM (anhydrous, not degassed), until Abs ~1. Solution (1.4 mL) was then transferred to a 1.5 mL cuvette with a sealed screw-top lid to minimize evaporation. The cuvette was irradiated with a 532 nm laser at 0.53±0.05 Wcm$^{-2}$ fluence. The fluence was taken as the average over 1/e of the Gaussian profile (FieldMate Laser Power Meter). The absorbance was monitored at distinct time points (JASCO V-770 UV-Visible/NIR spectrophotometer or a PerkinElmer Lambda25 spectrophotometer). From baseline corrected data, the percent absorbance at $\lambda_{max,abs}$ was plotted. The error represents standard deviation of the triplicate measurement.

FIG. 11

Solutions of dye in dichloromethane (1.4 mL, Abs ~1) were irradiated with a 1050 nm LED (Thor Labs mounted LED and collimation adaptor) and monitored by UV-Vis-IR spectroscopy. The power density (4.6 mWcm$^{-2}$±0.2 mWcm$^{-2}$) was measured with a FieldMate Laser Power Meter. Percent absorbance remaining was taken with respect to $\lambda_{max,abs}$ at t=0 min.

FIG. 12

Flav7 (3) was dissolved in anhydrous solvents DMSO, MeCN, DCM, THF, MeOH, and Acetone (not anhydrous). All samples were sonicated before taking an absorbance spectrum (see general experimental procedure for instrument and settings), with a baseline in the appropriate solvent. The concentrations were as follows: $2\times10^{-6}$ M for acetone, tetrahydrofuran, and methanol, $5\times10^{-5}$ M for dichloromethane and $1\times10^{-5}$ M for dimethyl sulfoxide and acetonitrile. These data were baseline corrected to 1300 nm and normalized.

FIG. 13

Flav7 (0.1 mg) was dissolved in 1 mL of 1% methanol/99% acetonitrile and monitored over time by LCMS (Agilent 1200 infinity series LC, 6100 series quadruple LCMS). The compounds were eluted on a C-18 column with a water/acetonitrile/water with 0.1% TFA solvent mixture using a gradient of 5-95% acetonitrile with 5% of 0.1% TFA in water over 7 min, followed by holding at 95% acetonitrile, 5% of 0.1% TFA in water for 3 min.

FIG. 14

Solutions of 3 were prepared in dicholormethane with an Abs ~2.3, aliquots of 2.5-3 mL were evaporated, dissolved in MeCN, sonicated for ~1 min, and additive solvent was added (if applicable) to reach the appropriate volume. Absorbance was monitored over time by UV-Vis-IR spectroscopy, and absorbance remaining was taken with respect to $\lambda_{max,abs}$ at t=0 min.

FIG. 15

A stock solution of Flav7 (3) in acetonitrile was prepared with Abs ~1.4. Aliquots were diluted to 2× the volume to achieve 0%, 10%, 20% and 50% water in acetonitrile. Plotted are the baseline corrected and normalized data.

FIG. 16

A stock solution of Flav7 (3) in acetonitrile was prepared with Abs ~1.4. An aliquot (1 mL) was diluted with 1 mL water and the absorbance was measured. After 1.5 h, solvent was evaporated, 3 was re-dissolved in 2 mL acetonitrile, sonicated, and absorbance was measured. Plotted are the baseline corrected and normalized data.

FIG. 17

Flav 7, IR-26 and IR-1061 were dissolved in DCM and their concentrations were adjusted until matched absorbances were reached at 808 nm, as observed by UV-Vis-IR spectroscopy (Cary 5000 UV-VIS-NIR spectrometer).

Scheme Experimental Procedures

7-Dimethylamino Flavyliym Heptamethine Dye (3, Flav7)

4-((E)-2-((E)-2-chloro-3-(2-((E)-7-(dimethylamino)-2-phenyl-4H-chromen-4-ylidene)ethylidene)cyclohex-1-en-1-yl)vinyl)-7-(dimethylamino)-2-phenylchromenylium perchlorate 7-N,N-dimethylamino-4-methyl-flavylium perchlorate[2] (1) (Chen, J.-R.; Wong, J.-B.; Kuo, P.-Y; Yang, D.-Y. Org. Lett. 2008, 10, 4823) (31.1 mg, 0.0855 mmol, 2.1 equiv), N-[(3-(anilinomethylene)-2-chloro-1-cyclohexen-1-yl)methylene]aniline 6 (13.0 mg, 0.040 mmol, 1.0 equiv.) and anhydrous sodium acetate (9 mg, 0.1 mmol, 2.5 equiv.) were dissolved in EtOH (0.78 mL, anhydrous) and heated to 90° C. for 6 hours. The solution was cooled to rt and evaporated onto silica gel. Dye 3 was purified via silica gel chromatography, eluting with a DCM/MeOH solvent gradient of 200:1, 150:1, 100:1, 80:1, 67:1 and 50:1. This procedure gave pure 3 (11.1 mg, 0.0145 mmol, 36%). $^1$H NMR (500 MHz, DMSO-$d_6$): δ 8.21 (d, J=10 Hz, 2H), 8.14-8.10 (m, 6H), 7.70-7.53 (m, 8H), 7.06 (d, J=15 Hz, 2H), 6.96 (dd, J=10 Hz, 2.5 Hz, 2H), 6.81 (d, J=2.5 Hz, 2H), 3.14 (s, 12H), 2.87-2.81 (m, 4H), 1.91 (t, J=6.3 Hz, 2H). $^{13}$C NMR (126 MHz, DMSO-$d_6$): δ 156.9, 155.9, 154.6, 145.0, 144.5, 138.5, 132.0, 131.6, 131.3, 129.6, 126.7, 126.5, 113.9, 113.8, 112.4, 102.3, 97.9, 27.2, 21.3, {peak at 38.9-40.1 beneath DMSO-$d_6$ solvent peak}. HRMS (ESI$^+$): Calculated for $C_{44}H_{40}ClN_2O_2^+$ [M]$^+$: 663.2773; found: 663.2784. Absorbance (DCM): 522 nm ($\varepsilon$=1.5±0.2×10$^4$ M$^{-1}$ cm$^{-1}$), 916 nm ($\varepsilon$=6.3±0.1×10$^4$ M$^{-1}$ cm$^{-1}$), 1026 nm ($\varepsilon$=2.4±0.2×10$^5$ M$^{-1}$ cm$^{-1}$). Emission (DCM, Ex. 730 nm): 1045 nm, $\Phi_F$=0.53±0.03%.

7-Dimethylamino Flavyliym Pentamethine Dye (4, Flav5)

7-(dimethylamino)-4-((1E,3E)-5-((E)-7-(dimethylamino)-2-phenyl-4H-chromen-4-ylidene)penta-1,3-dien-1-yl)-2-phenylchromenylium perchlorate 7-N,N-dimethylamino-4-methyl-flavylium perchlorate[2] (1) (29.8 mg, 0.0819 mmol, 2.1 equiv), malonaldehyde bis(phenylimine) (10.2 mg, 0.0394 mmol, 1.0 equiv.), and anhydrous sodium acetate (9 mg, 0.1 mmol, 2.7 equiv.) were combined in acetic anhydride (0.66 mL). The solution was freeze-pump-thawed ×3 and subsequently heated at 110° C. for 2.5 h. The solution was let cool to rt and evaporated onto silica gel. Dye 4 was purified via silica gel chromatography, eluting with a DCM/MeOH solvent gradient of 200:1, 167:1, 143:1, 125:1, 111:1, 100:1, 67:1. The procedure yielded pure 4 (13.1 mg, 0.0198 mmol, 50%). $^1$H NMR (500 MHz, DMSO-$d_6$): δ 8.2 (t, J=12.8 Hz, 2H), 8.11-8.03 (m, 4H), 7.98 (d, J=9.4 Hz, 2H), 7.66 (s, 2H), 7.61-7.52 (m, 6H), 7.07 (d, J=13.2 Hz, 2H), 6.94-6.86 (dd, J=9.2, 1.5 Hz, 2H), 6.82 (t, J=12.3 Hz, 1H), 6.77 (s, 2H), 3.13 (s, 12H). $^{13}$C NMR (126 MHz, DMSO-$d_6$): δ 156.3, 155.4, 154.2, 149.1, 145.7, 131.6, 131.2, 129.1, 126.1, 125.9, 115.3, 113.2, 110.9, 101.6, 97.4, {peak at 38.9-40.1 beneath DMSO-$d_6$ solvent peak}. HRMS (ESI$^+$): Calculated for $C_{39}H_{35}N_2O_2^+$ [M]$^+$: 563.2693; found: 563.2702. Absorbance (DCM): 546 nm ($\varepsilon$=1.4±0.1×10$^4$ M$^{-1}$ cm$^{-1}$), 776 nm ($\varepsilon$=4.8±0.4×10$^4$ M$^{-1}$ cm$^{-1}$), 862 nm ($\varepsilon$=2.4±0.2×10$^5$ M$^{-1}$ cm$^{-1}$). Emission (DCM, Ex. 840 nm): 908 nm, $\Phi_F$=5±2%.

7-Dimethylamino Flavyliym Monomethine Dye (5, Flav3)

7-(dimethylamino)-4-((E)-3-((E)-7-(dimethylamino)-2-phenyl-4H-chromen-4-ylidene)prop-1-en-1-yl)-2-phenylchromenylium perchlorate 7-N,N-dimethylamino-4-methyl-flavylium perchlorate[2] (1) (49.8 mg, 0.137 mmol, 1.5 equiv.), paraformaldehyde (2.7 mg, 0.090 mmol, 1.0 equiv.), and anhydrous sodium acetate (15 mg, 0.18 mmol, 2.0 equiv) were combined in acetic anhydride (1.0 mL). The solution was freeze-pump-thawed ×3 and heated at 70° C. for 30 m. The solution was cooled to rt and evaporated onto silica gel. Dye 5 was purified via silica gel chromatography, eluting with a DCM/EtOH solvent gradient of 200:1, 167:1, 143:1, 125:1, 111:1, 100:1. The most pure fractions, as determined by UV-Vis/IR spectroscopy were loaded onto a second silica gel column and run as before. The impure fractions from both columns were combined and run on another silica gel column with the same solvent system and gradient. This procedure yielded pure 5 (15.5 mg, 0.0243 mmol, 27%). $^1$H NMR (500 MHz, DMSO-$d_6$): δ 8.81 (t, J=12.9 Hz, 1H), 8.18-8.10 (m, 4H), 7.99 (s, 2H), 7.89 (d, J=9.6 Hz, 2H), 7.67-7.57 (m, 6H), 7.16 (d, J=13.0 Hz, 2H), 6.91 (dd, J=9.3, 2.5 Hz, 2H), 6.72 (d, J=2.5 Hz, 2H), 3.12 (s, 12H). $^{13}$C NMR (126 MHz, DMSO-$d_6$) δ 156.7, 155.4, 154.2, 147.2, 145.5, 131.6, 131.1, 129.0, 126.4, 125.5, 115.9, 113.2, 110.6, 102.0, 97.1, {peak at 38.9-40.1 beneath DMSO-$d_6$ solvent peak}. HRMS (ESI$^+$): Calculated for $C_{37}H_{33}N_2O_2^+$ [M]$^+$: 537.2537; found: 537.2525. Absorbance (DCM): 530 nm ($\varepsilon$=2.0±0.1×10$^4$ M$^{-1}$ cm$^{-1}$), 682 nm ($\varepsilon$=3.9±0.2×10$^4$ M$^{-1}$ cm-1), 746 nm ($\varepsilon$=2.2±0.1×10$^5$ M$^{-1}$ cm$^{-1}$). Emission (DCM, Ex. 675 nm): 766 nm, $\Phi_F$=2.9±0.5%.

7-Dimethylamino Flavyliym Trimethine Dye (6, Flav1)

(E)-7-(dimethylamino)-4-((7-(dimethylamino)-2-phenyl-4H-chromen-4-ylidene)methyl)-2-phenylchromenylium 2,2,2-trifluoroacetate (6) 7-N,N-dimethylamino-4-methyl-flavylium perchlorate[2] (1) (49.7 mg, 0.137 mmol, 1 equiv.) and anhydrous sodium acetate (25 mg, 0.31 mmol, 2.2 equiv) were dissolved in 10 mL EtOH and refluxed at 90° C.

under air for 3.3 h. The mixture was cooled to rt and evaporated onto silica gel. Dye 6 was purified via silica gel chromatography and reverse-phase HPLC. Via silica gel chromatography, dye 6 was eluted with a DCM/MeOH solvent gradient of 400:1, 200:1, 167:1, 143:1, 125:1, 111:1, 67:1, and 33:1. The most pure fractions were further purified in aliquots by HPLC in a water/MeCN with 0.1% TFA solvent mixture. The method used is as follows: 70:30 for 2 m, gradient to 30:70 over 60 m, gradient to 5:90 over 20 m, followed by a hold for 5 m and subsequent re-equilibration to 70:30 for 10 m. The procedure yielded pure 6 (9.5 mg, 0.016, 11%). $^1$H NMR (500 MHz, DMSO-d$_6$): δ 8.40 (d, J=10.5 Hz, 2H), 8.17 (dd, J=8.0, 1.7 Hz, 4H), 7.98 (s, 2H), 7.66-7.59 (m, 6H), 7.47 (s, 1H), 7.10 (dd, J=9.4, 2.6 Hz, 2H), 6.99 (d, J=2.6 Hz, 2H), 3.21 (s, 12H). $^{13}$C NMR (126 MHz, DMSO-d$_6$) δ 158.96, 158.63, 158.39, 158.15, 157.90, 156.31, 155.19, 150.61, 132.60, 131.54, 129.76, 127.63, 126.97, 121.43, 119.03, 116.64, 115.01, 114.06, 112.09, 105.40, 103.64, 97.71 {peak at 38.9-40.1 beneath DMSO-d$_6$ solvent peak}. $^{19}$F NMR (282 MHz, DMSO-d$_6$) δ−73.16. HRMS (ESI$^+$): Calculated for $C_{35}H_{31}N_2O_2^+$ [M]$^+$: 511.2380; found: 511.2366. Absorbance (DCM): 324 nm (ε=3.±1.×10$^3$ M$^{-1}$ cm$^{-1}$), 484 nm (ε=3.±1.×10$^3$ M$^{-1}$ cm$^{-1}$), 514 nm (ε=4.±1.×10$^3$ M$^{-1}$ cm$^{-1}$), 650 nm (ε=1.6±0.5×10$^4$ M$^{-1}$ cm$^{-1}$). Emission (DCM, Ex. 610 nm): 684 nm, $Φ_F$=0.7±0.5%.

TABLE 6

Photophysical characterization of 1, 3-6 (with errors)

| dye | absorption (DCM) | | emission (DCM) | | |
|---|---|---|---|---|---|
| | $λ_{max}$ (nm) | ε (M$^{-1}$cm$^{-1}$) × 10$^5$ | $λ_{max}$ (nm) | $Φ_F$ | QE/ε$Φ_F$ (M$^{-1}$cm$^{-1}$) |
| 1 | 510 | 0.17 ± 0.02 | 587 | — | — |
| 6 | 650 | 0.16 ± 0.05 | 684 | 0.7 ± 0.5% | 100 ± 90 |
| 5 | 746 | 2.2 ± 0.1 | 766 | 3 ± 0.5% | 6 600 ± 500 |
| 4 | 862 | 2.4 ± 0.2 | 908 | 5 ± 2% | 10 000 ± 3 000 |
| 3 | 1026 | 2.36 ± 0.02 | 1045 | 0.53 ± 0.03% | 1 200 ± 100 |

TABLE 3

$λ_{max, abs}$ (nm) in organic solvents

| compound | THF | DCM | Acetone | MeCN | DMSO | MeOH |
|---|---|---|---|---|---|---|
| Flav7 (3) | 1026 | 1026 | 1016 | 1013 | 1039 | 476 |
| Flav5 (4) | 848 | 862 | 854 | 848 | 868 | 845 |

TABLE 4

Photobleaching rates of Flav3 and HITCI with a 730 nm LED at 4.6 mWcm$^{-2}$ fluence

| compound | raw rate, k (×10$^4$) | relative rate, $k_{rel}$ (×10$^4$) |
|---|---|---|
| Flav3 | 6.9 ± 0.3 | 7.9 ± 0.6 |
| HITCI | 34 ± 2 | 34 ± 2 |

The following references are each hereby incorporated by reference in their entirety.
(1) Giepmans, B. N. G.; Adams, S. R.; Ellisman, M. H.; Tsien, R. Y. *Science* 2006, 312, 217-224.
(2) Lavis, L. D.; Raines, R. T. *ACS Chem. Biol.* 2014, 9, 855-866.
(3) Sun, W.; Guo, S.; Hu, C.; Fan, J.; Peng, X. *Chem. Rev.* 2016, 116, 7768-7817.
(4) (a) Mustroph, H.; Stollenwerk, M.; Bressau, V. *Angew. Chem., Int. Ed.* 2006, 45, 2016-2035. (b) Saccone, D.; Galliano, S.; Barbero, N.; Quagliotto, P.; Viscardi, G.; Barolo, C. *European J. Org. Chem.* 2016, 2244-2259. (c) Hales, J. M.; Barlow, S.; Kim, H.; Mukhopadhyay, S.; Bredas, J. L.; Perry, J. W.; Marder, S. R. *Chem. Mater.* 2014, 26, 549-560. (d) Alander, J. T.; Kaartinen, I.; Laakso, A.; Pätilä, T.; Spillmann, T.; Tuchin, V. V.; Venermo, M.; Välisuo, P. *Int. J. Biomed. Imaging* 2012, 2012, 940585.
(5) Gorka, A. P.; Nani, R. R.; Schnermann, M. J. *Org. Biomol. Chem.* 2015, 13, 7584-7598.
(6) (a) Hong, G.; Antaris, A. L.; Dai, H. *Nat. Biomed. Eng.* 2017, 1, 10. (b) Hong, G.; Diao, S.; Chang, J.; Antaris, A. L.; Chen, C.; Zhang, B.; Zhao, S.; Atochin, D. N.; Huang, P. L.; Andreasson, K. I.; Kuo, C. J.; Dai, H. *Nat. Photonics* 2014, 8, 723-730.
(7) (a) Woo, Y. a; Ahn, J. W.; Chun, I. K.; Kim, H. J. *Anal. Chem.* 2001, 73, 4964-4971. (b) Kershaw, S. V.; Harrison, M.; Rogach, A. L.; Kornowski, A. *IEEE J. Sel. Topics Quantum Electron.* 2000, 6, 534-543. (c) Marschall, S.; Sander, B.; Mogensen, M.; Jørgensen, T. M.; Andersen, P. E. *Anal. Bioanal. Chem.* 2011, 400, 2699-2720. (d) Onat, B. M.; Huang, W.; Masaun, N.; Lange, M.; Ettenberg, M. H.; Dries, C. *Proc. SPIE* 2007, 6542, 65420L.
(8) (a) Bricks, J. L.; Kachkovskii, A. D.; Slominskii, Y. L.; Gerasov, A. O.; Popov, S. V. *Dye. Pigment.* 2015, 121, 238-255. (b) *Near-Infrared Dyes for High Technology Applications*; Daehne, S., Resch-Genger, U., Wolfbeis, O. S., Eds.; NATO ASI Series; Kluwer Academic Publishers: Norwell, MA, 1998. (c) Ishchenko, A. A. *Russ. Chem. Rev.* 1991, 60, 1708-1743. (d) Bouit, P. A.; Aronica, C.; Toupet, L.; Guennic, B. Le; Andraud, C.; Maury, O. *J. Am. Chem. Soc.* 2010, 132, 4328-4335.
(9) Narayanan, N.; Patonay, G. *J. Org. Chem.* 1995, 60, 2391-2395.
(10) (a) Detty, M. R.; Murray, B. J. *J. Org. Chem.* 1982, 47, 5235-5239. (b) Detty, M. R.; Merkel, P. B. *J. Am. Chem. Soc.* 1990, 112, 3845-3855.
(11) (a) Reynolds, G. A.; Drexhage, K. H. 1977, 445, 5-8. (b) Kopainsky, B.; Qiu, P.; Kaiser, W.; Sens, B.; Drexhage, K. H. *Appl. Phys. B Photophysics Laser Chem.* 1982, 29, 15-18.
(12) Chen, J.-R.; Wong, J.-B.; Kuo, P.-Y.; Yang, D.-Y. *Org. Lett.* 2008, 10, 4823-4826.
(13) Hatami, S.; Würth, C.; Kaiser, M.; Leubner, S.; Gabriel, S.; Bahrig, L.; Lesnyak, V.; Pauli, J.; Gaponik, N.; Eychmüller, A.; Resch-Genger, U. *Nanoscale* 2015, 7, 133-143.
(14) Hu, H.; Przhonska, O. V.; Terenziani, F.; Painelli, A.; Fishman, D.; Ensley, T. R.; Reichert, M.; Webster, S.; Bricks, J. L.; Kachkovski, A. D.; Hagan, D. J.; Van Stryland, E. W. *Phys. Chem. Chem. Phys.* 2013, 15, 7666-7678.
(15) (a) Chen, J.; Kong, Y.; Feng, S.; Chen, C.; Wo, Y.; Wang, W.; Dong, Y.; Wu, Z.; Li, Y.; Chen, S. *ACS Sustain. Chem. Eng.* 2016, 4, 2932-2938. (b) Murphy, J. E.; Beard, M. C.; Norman, A. G.; Ahrenkiel, S. P.; Johnson, J. C.; Yu, P.; Mićić, O. I.; Ellingson, R. J.; Nozik, A. J. *J. Am. Chem. Soc.* 2006, 128, 3241-3247.
(16) (a) Dang, X.; Gu, L.; Qi, J.; Correa, S.; Zhang, G.; Belcher, A. M.; Hammond, P. T. *Proc. Natl. Acad. Sci.* 2016, 113, 1-6. (b) Tao, Z.; Hong, G.; Shinji, C.; Chen, C.; Diao, S.; Antaris, A. L.; Zhang, B.; Zou, Y.; Dai, H. *Angew. Chem. Int. Ed.* 2013, 52, 13002-13006.
(17) (a) Semonin, O. E.; Johnson, J. C.; Luther, J. M.; Midgett, A. G.; Nozik, A. J.; Beard, M. C. *J. Phys. Chem.*

Lett. 2010, 1, 2445-2450. (b) Penzkofer, A.; Lammel, O.; Tsuboi, T. *Opt. Commun.* 2002, 214, 305-313. (c) Kranitzky, W.; Kopainsky, B.; Kaiser, W.; Drexhage, K. H.; Reynolds, G. A. *Opt. Commun.* 1981, 36, 149-152.

(18) Casalboni, M.; De Matteis, F.; Prosposito, P.; Quatela, A.; Sarcinelli, F. *Chem. Phys. Lett.* 2003, 373, 372-378.

(19) (a) Yang, Q.; Ma, Z.; Wang, H.; Zhou, B.; Zhu, S.; Zhong, Y.; Wang, J.; Wan, H.; Antaris, A.; Ma, R.; Zhang, X.; Yang, J.; Zhang, X.; Sun, H.; Liu, W.; Liang, Y.; Dai, H. *Adv. Mater.* 2017, DOI: 10.1002/adma.201605497. (b) Zhu, S.; Yang, Q.; Antaris, A. L.; Yue, J.; Ma, Z.; Wang, H.; Huang, W.; Wan, H.; Wang, J.; Diao, S.; Zhang, B.; Li, X.; Zhong, Y.; Yu, K.; Hong, G.; Luo, J.; Liang, Y.; Dai, H. *Proc. Natl. Acad. Sci. U.S.A.* 2017, DOI: 10.1073/pnas.1617990114.

Other embodiments are within the scope of the following claims.

What is claimed is:

1. A flavylium polymethine dye selected from:

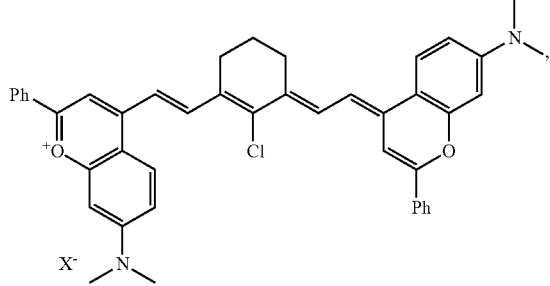 [SMILES: "ClO4-" ; CN(C)c1ccc2c(c1)OC(c1ccccc1)=C/C2=C\C=C1/CCCC(/C=C/c2cc(-c3ccccc3)[o+]c3cc(N(C)C)ccc23)=C1Cl]

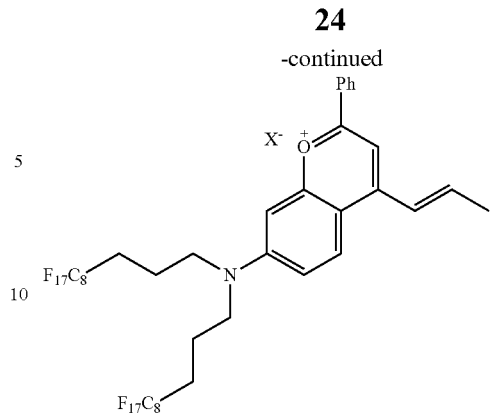

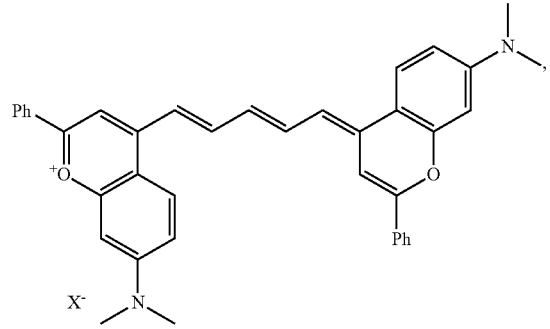 [SMILES: "ClO4-" ; CN(C)c1ccc2c(c1)OC(c1ccccc1)=C\C2=C/C=C/C=C/c1cc(-c2ccccc2)[o+]c2cc(N(C)C)ccc12]

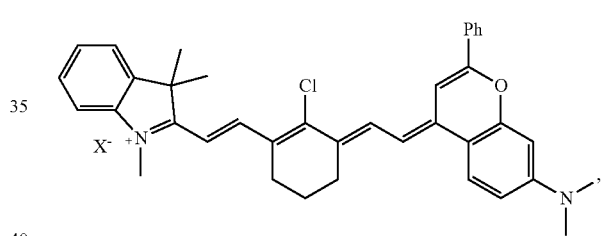

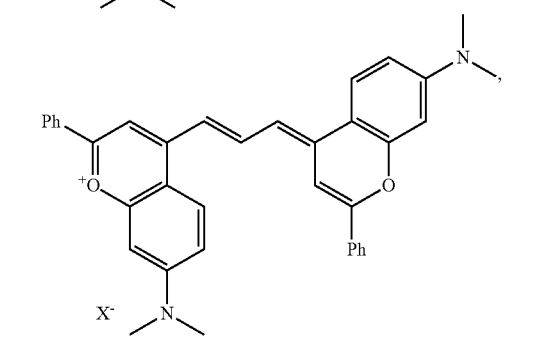

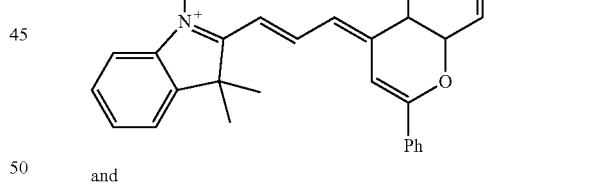

and

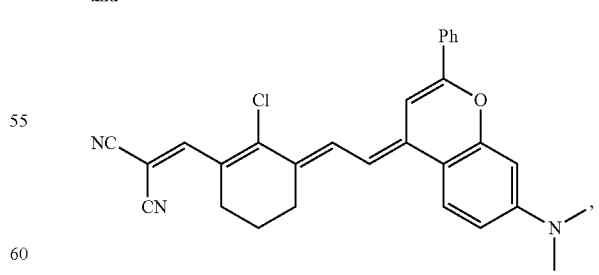

wherein

X⁻ is $Cl^-$, $ClO_4^-$, $BF_4^-$, $Br^-$, $I^-$, tosylate, triflate, trifluoroacetate, acetate, bromide, or tetraalkylborate, and R is hydrogen, alkyl, acyl or heteroalkyl.

2. The flavylium polymethine dye of claim 1, wherein the flavylium polymethine dye is 4. The flavylium polymethine dye of claim 1, wherein the flavylium polymethine dye is

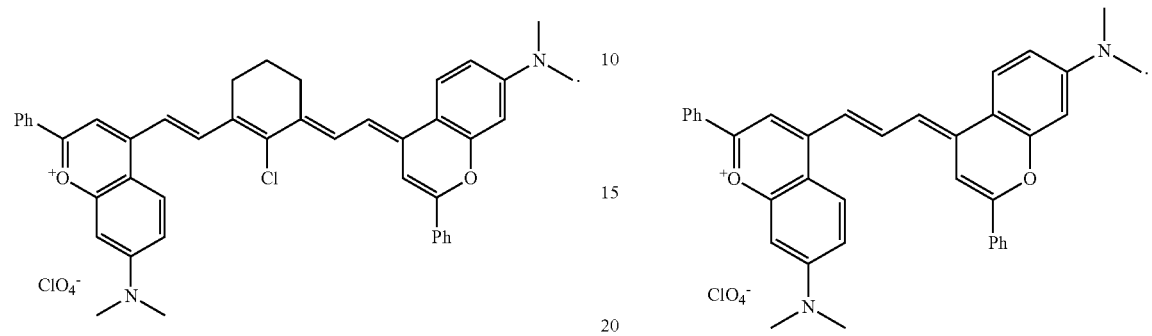

3. The flavylium polymethine dye of claim 1, wherein the flavylium polymethine dye is 5. The flavylium polymethine dye of claim 1, wherein the flavylium polymethine dye is

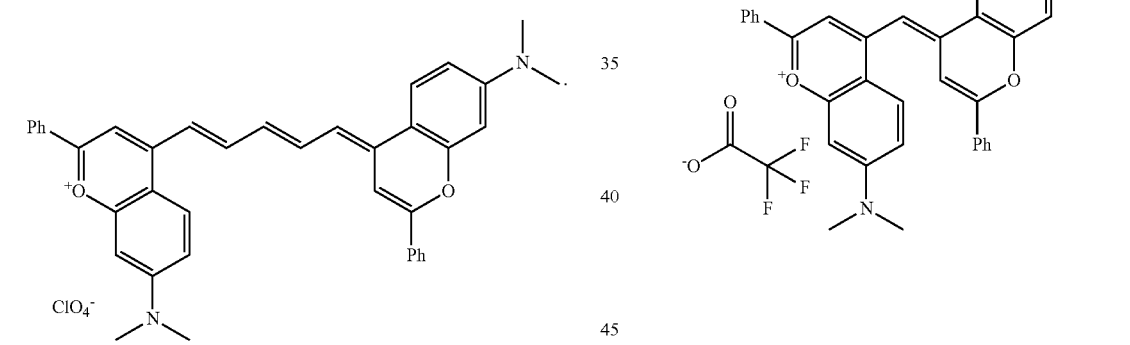

6. The flavylium polymethine dye of claim 1, wherein the flavylium polymethine dye is

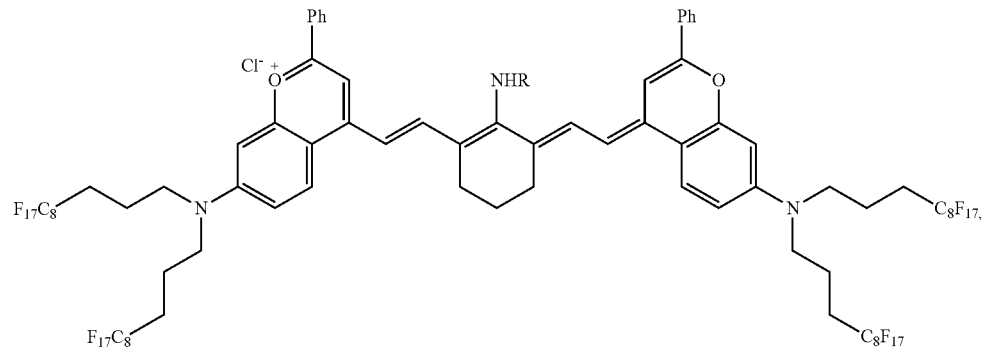

wherein
R is hydrogen, alkyl, acyl or heteroalkyl.

7. The flavylium polymethine dye of claim 1, wherein the flavylium polymethine dye is
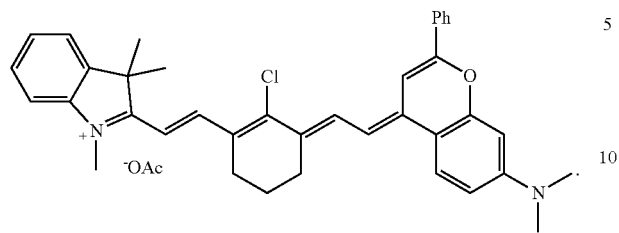
8. The flavylium polymethine dye of claim 1, wherein the flavylium polymethine dye is
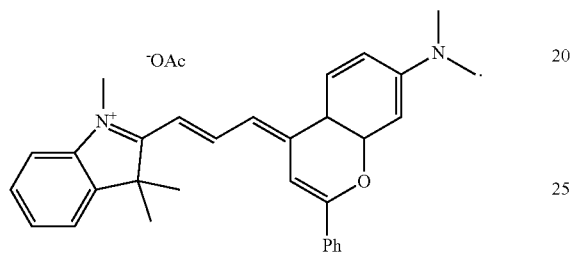
9. The flavylium polymethine dye of claim 1, wherein the flavylium polymethine dye is
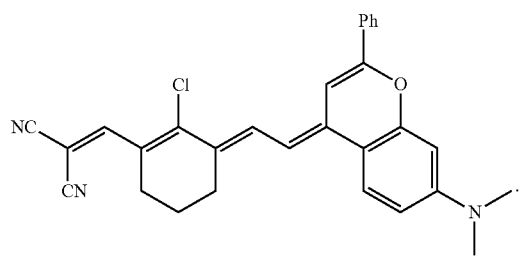 [SMILES: CN(C)c1ccc2c(c1)OC(c1ccccc1)=C/C2=C\C=C1/CCCC(C=C(C#N)C#N)=C1Cl]
* * * * *